US012778968B2

(12) United States Patent
Hayardeny-Nissimoiv et al.

(10) Patent No.: US 12,778,968 B2
(45) **Date of Patent: *Nov. 3, 2026**

(54) TREATMENT FOR FIBROSIS AND INHIBITION OF FIBROSIS

(71) Applicant: GALMED RESEARCH AND DEVELOPMENT LTD, Tel Aviv (IL)

(72) Inventors: Liat Hayardeny-Nissimoiv, Tel Aviv (IL); Tali Gorfine, Tel Aviv (IL); Allen Baharaff, Tel Aviv (IL); Jose M. Mato De La Paz, Getxo (ES)

(73) Assignee: Galmed Research and Development Ltd, Tel Aviv (IL)

( * ) Notice: Subject to any disclaimer, the term of this patent is extended or adjusted under 35 U.S.C. 154(b) by 900 days.

This patent is subject to a terminal disclaimer.

(21) Appl. No.: 17/863,472

(22) Filed: Jul. 13, 2022

(65) Prior Publication Data

US 2022/0362263 A1 Nov. 17, 2022

Related U.S. Application Data

(63) Continuation-in-part of application No. 16/182,767, filed on Nov. 7, 2018, now abandoned, which is a continuation-in-part of application No. PCT/IB2017/001535, filed on Nov. 10, 2017, and a continuation-in-part of application No. PCT/IB2017/001521, filed on Nov. 10, 2017, and a continuation-in-part of application No. 15/789,564, filed on Oct. 20, 2017, now Pat. No. 11,197,870.

(60) Provisional application No. 62/475,129, filed on Mar. 22, 2017, provisional application No. 62/475,132, filed on Mar. 22, 2017, provisional application No. 62/420,012, filed on Nov. 10, 2016, provisional application No. 62/420,017, filed on Nov. 10, 2016, provisional application No. 62/420,009, filed on Nov. 10, 2016.

(51) Int. Cl.

| | |
|---|---|
| ***A61K 31/575*** | (2006.01) |
| ***A61K 31/202*** | (2006.01) |
| ***A61K 45/06*** | (2006.01) |
| ***A61P 1/16*** | (2006.01) |

(52) U.S. Cl.

CPC .......... *A61K 31/575* (2013.01); *A61K 31/202* (2013.01); *A61K 45/06* (2013.01); *A61P 1/16* (2018.01)

(58) Field of Classification Search

CPC .... A61K 31/575; A61K 31/202; A61K 45/06; A61K 31/4178; A61P 1/16; A61P 19/04

See application file for complete search history.

(56) References Cited

U.S. PATENT DOCUMENTS

| | | | | |
|---|---|---|---|---|
| 2,252,863 | A | 8/1941 | Raymond | |
| 4,022,806 | A | 5/1977 | Frost | |
| 5,512,558 | A | 4/1996 | Enhsen | |
| 6,384,024 | B1 | 5/2002 | Gilat | |
| 6,395,722 | B1 | 5/2002 | Gilat | |
| 6,589,946 | B2 | 7/2003 | Gilat | |
| 6,642,268 | B2 | 11/2003 | Keller | |
| 7,501,403 | B2 | 3/2009 | Gilat | |
| 8,110,564 | B2 | 2/2012 | Gilat | |
| 8,975,246 | B2 | 3/2015 | Gilat | |
| 9,498,484 | B2 | 11/2016 | Fiorucci | |
| 10,266,560 | B2 | 4/2019 | Or | |
| 10,849,911 | B2 | 12/2020 | Baharaff | |
| 11,166,964 | B2 * | 11/2021 | Halpern | A61K 31/575 |
| 11,197,870 | B2 * | 12/2021 | Hayardeny-Nissimov | A61P 1/16 |
| 2008/0064888 | A1 | 3/2008 | Allegrini | |
| 2009/0149537 | A1 | 6/2009 | Gilat | |
| 2011/0014126 | A1 | 1/2011 | Evans | |
| 2012/0157419 | A1 | 6/2012 | Gilat | |
| 2012/0214872 | A1 | 8/2012 | Gilat | |
| 2012/0264824 | A1 | 10/2012 | Mizuguchi | |
| 2012/0277448 | A1 | 11/2012 | Jiang | |
| 2016/0023983 | A1 | 1/2016 | Gagnon | |
| 2016/0175223 | A1 | 6/2016 | Dayan | |
| 2016/0175324 | A1 | 6/2016 | Dayan | |
| 2016/0304553 | A1 | 10/2016 | Baharaff | |
| 2017/0196891 | A1 | 7/2017 | Halpern | |
| 2017/0362211 | A1 | 12/2017 | Lairson | |
| 2018/0125862 | A1 | 5/2018 | Hayardeny-Nissimov | |
| 2019/0175619 | A1 | 6/2019 | Hayardeny-Nissimov | |

FOREIGN PATENT DOCUMENTS

| | | | |
|---|---|---|---|
| CA | 3025671 | A1 | 12/2017 |
| JP | 2002511482 | A | 4/2002 |
| JP | 2003516317 | A | 5/2003 |
| JP | 2007534757 | A | 11/2007 |

(Continued)

OTHER PUBLICATIONS

Rieder, Florian. "The Gut Microbiome in Intestinal Fibrosis: Environmental Protector or Provocateur?" Science Translational Medicine, vol. 5, No. 190, Jun. 2013. DOI.org (Crossref), https://doi.org/10.1126/scitranslmed.3004731. (Year: 2013).*

Npl—Devkota et al; (2013). Bile acids as modulators of gut microbiota linking dietary habits and inflammatory bowel disease: a potentially dangerous liaison. Gastroenterology, 144(4), 844-846.

NPL—Wynn, T. A., & Ramalingam, T. R. (2012). Mechanisms of fibrosis: therapeutic translation for fibrotic disease. Nature medicine, 18(7), 1028-1040.

"Non-alcoholic fatty liver disease", Wikipedia; downloaded on Feb. 22, 2018.

(Continued)

*Primary Examiner* — Clinton A Brooks
*Assistant Examiner* — Kyle Nottingham
(74) *Attorney, Agent, or Firm* — Mark S. Cohen; PEARL COHEN LLP

(57) ABSTRACT

The present invention relates to unit dosage forms of 3D-arachidylamido-7α,12α-dihydroxy-5β-cholan-24-oic acid (Aramchol™) and use thereof in the treatment and/or inhibition of fibrosis.

6 Claims, 29 Drawing Sheets

(56) References Cited

FOREIGN PATENT DOCUMENTS

| | | | | |
|---|---|---|---|---|
| JP | 2019502724 | A | 1/2019 | |
| KR | 20030092063 | A | 12/2003 | |
| KR | 20100031771 | A | 3/2010 | |
| KR | 20120123691 | A | 11/2012 | |
| KR | 20130124524 | A | 11/2013 | |
| WO | WO-99/52932 | A1 | 10/1999 | |
| WO | WO-02/083147 | A1 | 10/2002 | |
| WO | WO-2009/060452 | A2 | 5/2009 | |
| WO | WO-2010/086864 | A1 | 8/2010 | |
| WO | WO-2011/074607 | A1 | 6/2011 | |
| WO | WO-2014/093711 | A1 | 6/2014 | |
| WO | WO-2015/019358 | A1 | 2/2015 | |
| WO | WO-2015/019359 | A1 | 2/2015 | |
| WO | WO-2015/083164 | A1 | 6/2015 | |
| WO | WO-2015/186126 | A1 | 12/2015 | |
| WO | WO-2016/112305 | A1 | 7/2016 | |
| WO | WO-2016/199137 | A1 | 12/2016 | |
| WO | WO-2017/017677 | A1 | 2/2017 | |
| WO | WO-2017048322 | A1 * | 3/2017 | ............ A61K 31/18 |
| WO | WO-2017/125929 | A1 | 7/2017 | |
| WO | WO-2017/210526 | A1 | 12/2017 | |
| WO | WO-2018/087599 | A1 | 5/2018 | |

OTHER PUBLICATIONS

Aitipamula et al. (Cryst. Growth Des. 2012, 12, 2•147-2152).

Anumah et aL (20.17). Liver Fibrosis: Mechanisms of Development, Experimental Models and Treatment Strategies. Research Journal of Pharmaceutical Biological and Chemical Sciences, 8(2), 682-695.

Aramchol Demonstrates Significant Anti-Fibrotic Effect in a Pre-Cincal Model of Fatty Liver Disease on Line: Galmed Pharmaceuticals ltd: Mar. 30, 2016.

Aramchol demonstrates significant anti-fibrotic effect in a pre-clinical model of fatty liver disease, on line, Mar. 30, 2016, https://galmed pharma.investorroom.com/2016-03-30-Aramchol-Demonstrates-Significant-Anti-Fibrotic-Effect-in-a-Pre-clinical-Model-of-Fatty-Liver-Disease.

Ayesha Jacob et al; (DOI: 10.1039/C2CE26706C (PAPER} CrystEngcomm, 2013, 15, 931-939}.

Ayesha Jacobs et al (28th European Crystallographic Meeting, ECM 28, UK, 2013 Acta Cryst. (2013). A69, s645; Aug. 2013; Acta Crystallographica Section A Foundations of Crystallography 69{a1):s645-s645, 001:10.1107/SO 10876731309435X, Salts of {+)-deoxycholic acid with amines: structure and chiral resolution}.

Brodosi et al: (2017). Nash: A glance at the landscape of pharmacological treatment. Annals of hepatology, 15(5), 673-681.

Brodosi et al; Nash: A glance at the landscape of pharmacological treatment, Annals of Hepatology Sep. 2016, 15(5), 673-681.

Clinical trial of Aramchol and Food Effect in Healthy Volunteers National Library of Medicine NCT02374437; Feb. 26, 2015.

Clinical trials.gov: "a Phase 1 Single and Multiple-Dose Study of Aramchol in Healthy Male Volunteers" National Library of Medicine NCT00776841; Nov. 2, 2010.

Clinicaltrials.gov [Internet] "A Clinical Trial to Evaluate the Efficacy and Safety of Two Aramchol Doses Versus Placebo in Patient with NASH", National Library of Medicine NCT02279524, updated Nov. 2, 2015, available online at: https://clinicaltrials.gov/archive/NC002279524/2015 11 02.

Clinicaltrials.gov [Internet] "A Clinical Trial to Evaluate the Efficacy and Safety of Two Aramchol Doses Versus Placebo in Patient with NASH", National Library of Medicine NCT02279524, updated Oct. 30, 2014, available online at: https://clinicaltrials.gov/archive/NCT02279524/2014_10_30.

Clinicaltrials.gov: A Phase 1, Open-Label Study to Evaluate the Safety, Tolerability, and Pharmacokinetics of Aramchol in Subjects With Hepatic Impairment. NCT04480827 on Jul. 21, 2020.

Clinicaltrials.gov: A phase llb double blind randomized controlled clinical trialto evaluate the efficacy and safety of two aramchol doses versus placebo in patients with non-alcoholic steatohepatitis (NASH)—Aramchol 005 Study. NCT02279524 on Oct. 30, 2014.

ClinicalTrials.gov: Study of Aramchol in Patients with Fatty Liver Disease or Nonalcoholic Steathepatitis{Aramchol003}, Jan. 30, 2012; National Institute of Health.

Corsetti, G. et al. {2011). Essential amino acid supplementation decreases liver damage induced by chronic ethanol consumption in rats. International journal of immunopathology and pharmacology, 24{3}, 611-619.

De Ouveira Da Silva, et ai. (2017). Molecular interplays in hepatic steilate cells: apoptosis, senescence, and phenotype reversion as ceilular connections that modulate livP.r fihrnc::i!';. f":,=,/1 hinfnrw int,=,rn;-:itjnn;:il41fCi\ 5=14fi-CiJ:;Q.

Eisenblaetter, T. et al (2018). Dose Linearity and Proportionality. In Drug discovery and Evalution: Methods in Clinical Pharmacology, Springer, Cham. P. Feb. 1-20, 2018.

Expert opinion on emerging drugs, Aug. 26, 2016, vol. 21, No. 3, p. 343-357.

Friedman et al (2018). A randomized, placebo-controlled trial of cenicriviroc for treatment of nonalcoholic steatohepatitis with fibrosis. Hepatology, 67(5), 1754-1767.

Grouix et al (2018). PB!-4050 reduces stellate cell activation and liver fibrosis through modulation of intracellular ATP levels and the liver kinase B1/AMP-•activated protein kinase/mammalian target of rapamycin pathway. Journal of Pharmacology and Experimental Therapeutics, 367(1), 71-81.

Helton, W. S. et al. (1990). Glutamine prevents pancreatic atrophy and fatty liver during elemental feeding. Journal of Surgical Research, 48{4}, 297-303.

International Preliminary Report on Patentability, mailed Jun. 7, 2016 in connection with PCT International Application No. PCT/IL2014/051052.

International Search Report, mailed Mar. 4, 2015 in connection with PCT International Application No. PCT/IL2014/051052.

International Search Report, mailed Sep. 25, 2016 in connection with PCT International Application No. PCT/IL2016/0505955.

IPRP in respect of PCT/IL2019/051121 dated May 20, 2021.

Iruarrizaga-Lejarreta et al (2017). Role of aramchol in steatohepatitis and fibrosis in mice. Hepatology communications, 1(9), 911-927.

Kol Symposium & Pipeline Update, Galmed Pharmaceuticals Ltd. Jan. 26, 2021.

Kurikawa, Nobuya, et al. "A novel inhibitor of stearoyl-CoA desaturase-1 attenuates hepatic lipid accumulation, liver injury and inflammation in model of nonalcoholic steatohepatitis." Biological and Pharmaceutical Bulletin 36.2 (2013): 259-267.

Lange et al. (Journal of Pharmaceutical Sciences. Soluble Steroids, vol. 51, No. 11. pp 1i02-1106, Nov. 1962).

Leikin-Frenkel et al (2010). Fatty acid bile acid conjugate inhibits hepatic stearoyl coenzyme A desaturase and is non-atherogenic. Archives of medical research, 41(6), 397-404.

Leikin-Frenkel et al., Treatment of preestablished diet-induced fatty liver by oral fatty acid-bile acid conjugates in rode, European Journal of Gastroenterology & Hepatology, (2008), 20(12), pp. 1205-1213.

Loomba, et al (2018). The ASK1 inhibitor seionsertib in patients with nonalcoholic steatohepatitis: a randomized, phase 2 trial. Hepatofogv, 67(2), 549-559.

Neuschwander-Tetri,et al (2015). Farnesoid X nuclear receptor iigand obetichoiic acid for non-cirrhotic, non-alcoholic steatohepatitis (FUNT): a multicentre, randomised, lolacebo-controlled triai. The Lancet, 385(9972), 956-965.

Non-alcoholic fatty liver disease Wikipedia 2018.

Noureddin et al, Review article: emerging anti-fibrotic therapies in the treatment of non-alcoholic steatohepatitis,Aliment Pharmacol Ther, Jun. 2016, 43(11), 1109-1123.

Noureddin et al. (2016). Promising therapies for treatment of nonalcoholic steatohepatitis. Expert opinion on emerging drugs, 21(3), 343-357.

Powell, D. A. (2014). An overview of patented small molecule stearoyl coenzyme—A desaturase inhibitors (2009-2013). Expert opinion on therapeutic patents, 24(2), i 55-175.

(56) References Cited

OTHER PUBLICATIONS

Pritchard et al; Identifying Novel Targets for Treatment of Liver Fibrosis: What Can We Learn from Injured Tissues which Heal Without a Scar? Bentham Science Publishers Curr Drug Targets. 2015; 16(12): 1332-1346.
Ratziu et al (2016). Elafibranor, an agonist of the peroxisome proliferator-activated receptor-a and- c, induces resolution of nonalcoholic steatohepatitis without fibrosis worsening. Gastroenterology, 150(5), 1•147-1159.
Ratziu, Vlad, et al. "One-year results of the global phase 2b randomized placebo-controlled arrest trial of Aramchol, a stearoyl CoA desaturase inhibitor, in patients with NASH." Hepatology. vol. 68. No. 1. p. 1448A-1449A, Oct. 2018.
Renshaw; Preparation of Choline and some of its salts; pg i 28 Organic and Biological 892: 1910.
Ruchi Bansal et al (2016). Clinical advancements in the targeted therapies against liver fibrosis. Mediators of inflammation, 2016.
Sachan, D. S. et al. {1984). Ameliorating effects of carnitine and its precursors on alcohol-induced fatty liver. The American journal of clinical nutrition, 39{5), 738-744.
Safadi et al (2014). The fatty acid-bile acid conjugate aramchol reduces liver fat content in patients with nonalcoholic fatty liver disease. Clinical Gastroenterology and Hepatoloav, 12(12), 2085-2091.
Safadi Rifaat et al; One year results of the global phase 2b Randomized placebo-controlled Arrest Trial of Aramchol, a Stearoyl CoA Desaturase Inhibitor, in patients with Nash; Hepatology, vol. 68 No. 1 Oct. 2018 p. 1447-1448.
Safadi, Rifaat, et al. "The Fatty Acid-Bile Acid Conjugate Aramchol Reduces Liver Fat Content in Patients With Nonalcoholic Fatty Liver Disease." Clinical Gastroenterology and Hepatology 12.12 (2014): 2085-2091.
Sanyal et ai (2010). Piogiitazone, vitamin E, or placebo for nonalcoholic steatohepatitis. New England Journal of Medicine, 362(18), 1675-1685.
Singh et al (2015). Fibrosis progression in nonalcoholic fatty liver vs nonalcoholic steatohepatitis: a systematic review and meta-analysis of paired-biopsy studies. Clinical Gastroenteroloav and Hepatoloav, 13(4), 643-654.
Singh et al; Fibrosis progression in nonalcoholic fatty liver vs nonalcoholic steatohepatitis: a systematic review and meta-analysis of paired-biopsy studies Clinical Gastronenterology and Hepatology Apr. 1, 2015;13(4):643-54.
Stahl, "Preparation of Water-soluble Compounds Through Salt Formation" The practice of medicinal chemistry, Chapter 35, second edition, p. 601-615, ISBN 0-12-744481-5, XP002566271.
Study of Armachol in Patients with Fatty Liver Disease or Nonalcoholic Steathepatitis (Aramchol003), Jan. 30, 2012: National Institute ot Health. Clinical Trials.gov.
Trovato et al (2014). 4Ps medicine of the fatty liver: the research model of predictive, preventive, personalized and participatory medicine-recommendations for facing obesity, fatty liver and fibrosis epidemics. EPMA Journal, 5(1), 21.
Written Opinion of the International Searching Authority, mailed Mar. 4, 2015 in connection with PCT International Aoolication No. PCT/IL2014/051052.
Written Opinion of the International Searching Authority, mailed Sep. 25, 2016 in connection with PCT International Application No. PCT/IL2016/050595.
Zhang Yaowu, Medicinal Basic Chemistry Peoples Military Medical Press pp. 293-294 Chemical properties of carboxylic acids {in chinese only).

* cited by examiner

| Parameter | Ka | V/F | Cl/F | Tlag |
|---|---|---|---|---|
| Estimate | 0.187581 | 0.532041 | 0.009159 | 2.12531 |
| CV% | 22.3 | 17.1 | 14.2 | 15.4 |

| Parameter | Ka | V/F | Cl/F | Tlag |
|---|---|---|---|---|
| **Value** | 0.187581 | 0.532041 | 0.009159 | 2.12531 |

| Parameter | Ka | V/F | Cl/F | Tlag |
|---|---|---|---|---|
| Value | 0.187581 | 0.709388 | 0.012213 | 2.12531 |

Fibrosis Improvement (≥1 stage)
Without Worsening of NASH

Progression to Cirrhosis*

TREATMENT FOR FIBROSIS AND INHIBITION OF FIBROSIS

This application is a continuation in part of U.S. application Ser. No. 16/182,767, filed Nov. 7, 2018, which is a continuation in part of International Application No. PCT/IB2017/001535, filed Nov. 10, 2017, which claims the benefit of U.S. Provisional Application No. 62/475,132, filed Mar. 22, 2017, and U.S. Provisional Application No. 62/420,009, filed Nov. 10, 2016; a continuation in part of International Application No. PCT/IB2017/001521, filed Nov. 10, 2017, which claims the benefit of U.S. Provisional Application No. 62/475,129, filed Mar. 22, 2017, U.S. Provisional Application No. 62/420,017, filed Nov. 10, 2016, U.S. Provisional Application No. 62/420,012, filed Nov. 10, 2016, and U.S. Provisional Application No. 62/420,009, filed Nov. 10, 2016; and a continuation in part of U.S. application Ser. No. 15/789,564, filed Oct. 20, 2017, which claims the benefit of U.S. Provisional Application No. 62/475,129, filed Mar. 22, 2017, U.S. Provisional Application No. 62/420,017, filed Nov. 10, 2016, and U.S. Provisional Application No. 62/420,009, filed Nov. 10, 2016, the contents of each of which are hereby incorporated by reference.

Throughout this application various publications are referenced. The disclosures of these publications in their entireties are hereby incorporated by reference into this application in order to more fully describe the state of the art to which this invention pertains.

FIELD OF THE INVENTION

The present invention relates to unit dosage forms of 3β-arachidylamido-7α,12α-dihydroxy-5β-cholan-24-oic acid (Aramchol™) and use thereof in the treatment and/or inhibition of fibrosis.

BACKGROUND OF THE INVENTION

Aramchol™ is an amide conjugate of arachidic acid and 3-aminocholic acid, effective in reducing liver fat content as well as improving metabolic parameters associated with fatty liver disease. It is an oral, liver-targeted, fatty acid-bile acid conjugate that down-regulates stearoyl CoA type 1 desaturase. It belongs to a family of synthetic Fatty-Acid/Bile-Acid Conjugates (FABACs) and is being developed as a potentially disease modifying treatment for fatty liver disease and Non Alcoholic SteatoHepatitis (NASH).

Aramchol™ is chemically named 3β-arachidylamido-7α,12α-dihydroxy-5β-cholan-24-oic acid (or (4R)-4-((3S,5S,7R,10S,12S,13R,17R)-7,12-dihydroxy-3-icosanamido-10,13-dimethylhexadecahydro-1H-cyclopenta[a]phenanthren-17-yl)pentanoic acid, (IUPAC name)), and is represented by the following chemical structure:

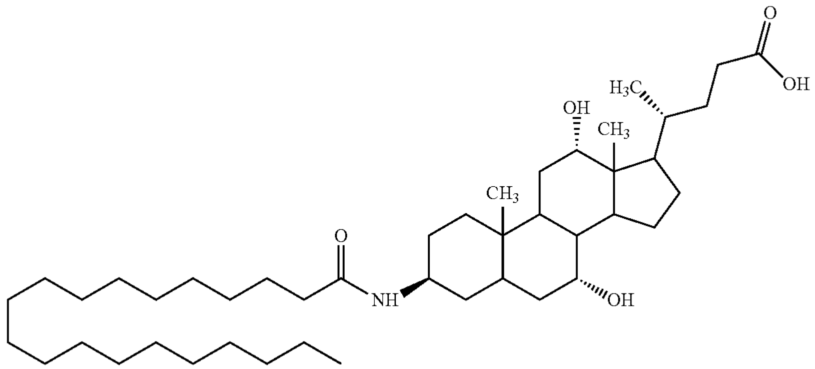 [SMILES: CCCCCCCCCCCCCCCCCCCC(=O)N[C@H]1CCC2(C)C(C1)C[C@@H](O)C1C2C[C@H](O)C2(C)C1CCC2[C@H](C)CCC(=O)O]

Aramchol™, processes for its preparation, and use thereof are disclosed in U.S. Pat. Nos. 6,384,024; 6,395,722; 6,589,946; 7,501,403; 8,110,564; U.S. 2012/0214872; and WO 2009/060452.

Fibrosis

The formation of fibrous connective tissue is part of the normal healing process following tissue damage due to injury or inflammation. During this process, activated immune cells including macrophages stimulate the proliferation and activation of fibroblasts, which in turn deposit connective tissue. However, abnormal or excessive production of connective tissue may lead to accumulation of fibrous material such that it interferes with the normal function of the tissue. Fibrotic growth can proliferate and invade healthy surrounding tissue, even after the original injury heals. Such abnormal formation of excessive connective tissue, occurring in a reparative or reactive process, is referred to as fibrosis.

Physiologically, fibrosis acts to deposit connective tissue, which can obliterate the architecture and function of the underlying organ or tissue. Defined by the pathological accumulation of extracellular matrix (ECM) proteins, fibrosis results in scarring and thickening of the affected tissue, which interferes with normal organ function. In various conditions, the formation of fibrotic tissue is characterized by the deposition of abnormally large amounts of collagen. The synthesis of collagen is also involved in a number of other pathological conditions. For example, clinical conditions and disorders associated with primary or secondary fibrosis, such as systemic sclerosis, graft-versus host disease (GVHD), pulmonary fibrosis and autoimmune disorders, are distinguished by excessive production of connective tissue, which results in the destruction of normal tissue architecture and function. These diseases can best be interpreted in terms of perturbations in cellular functions, a major manifestation of which is excessive collagen synthesis and deposition. The role of collagen in fibrosis has prompted attempts to develop drugs that inhibit its accumulation.

Hepatic Fibrosis

Fibrosis of the liver, also referred to herein as hepatic fibrosis, may be caused by various types of chronic liver injury, especially if an inflammatory component is involved. Self-limited, acute liver injury (e.g., acute viral hepatitis A), even when fulminant, does not necessarily distort the scaffolding architecture and hence does not typically cause fibrosis, despite loss of hepatocytes. However, factors such as chronic alcoholism, malnutrition, hemochromatosis, and exposure to poisons, toxins or drugs, may lead to chronic liver injury and hepatic fibrosis due to exposure to hepatotoxic chemical substances. Hepatic scarring, caused by surgery or other forms of injury associated with mechanical biliary obstruction, may also result in liver fibrosis.

Fibrosis itself is not necessarily symptomatic, however it can lead to the development of portal hypertension, in which scarring distorts blood flow through the liver, or cirrhosis, in which scarring results in disruption of normal hepatic architecture and liver dysfunction. The extent of each of these pathologies determines the clinical manifestation of hepatofibrotic disorders. For example, congenital hepatic fibrosis affects portal vein branches, largely sparing the parenchyma. The result is portal hypertension with sparing ofhepatocellular function.

Treatment

Attempts to develop anti-fibrotic agents for the treatment of various disorders have been reported. However, treatment of established fibrosis, formed after months or years of chronic or repeated injury, remains a challenge. In its initial stages, hepatic fibrosis may regress if the cause is reversible (e.g. with viral clearance). Thus, the majority of available treatment options are designed to remove the basis of the liver injury, such as by eliminating hepatitis B virus or hepatitis C virus in chronic viral hepatitis, abstaining from alcohol in alcoholic liver disease, removing heavy metals such as iron in hemochromatosis or copper in Wilson disease, and decompressing bile ducts in biliary obstruction.

Treatments aimed at reversing the fibrosis are usually too toxic for long-term use (e.g. corticosteroids, penicillamine) or have no proven efficacy (e.g. colchicine). Silymarin, present in milk thistle, is a popular alternative medicine used to treat hepatic fibrosis, appears to be safe but to lack efficacy.

Potential Therapeutic Agents

Attempts to develop specific anti-fibrotic agents for the treatment of liver diseases have been reported. For example, U.S. Pat. No. 8,729,046 relates to methods for treating fibrosis of a tissue, including fibrosis of the liver, using combinations of nucleic acids or nucleic acid analogs. Specifically, the nucleic acids or analogs thereof are targeted to microRNAs of the miR23b cluster. U.S. Pat. No. 6,562,829 discloses compositions for treating hepatic fibrosis and methods of using and manufacturing the composition, the composition comprising a quinazolinone derivative, preferably Halofuginone. U.S. Pat. No. 8,858,954 is directed to pharmaceutical composition for preventing and treating liver fibrosis or nonalcoholic fatty liver disease, comprising 50 to 90% by weight of *Cordyceps sinensis* mycelium powder, and 10 to 50% by weight of condensed astragalus powder.

U.S. Pub. No. 2015/359805 relates to Farnesoid X receptor (FXR) modulators which can be used for the treatment of cholestatic disorders, in particular to bile acid derivatives wherein the C6 contains an ethyl and the C24 carboxy group is transformed into a sulphate group. Among the disorders suggested to be treated are alcoholic liver disease, living donor transplant liver regeneration, congenital hepatic fibrosis, choledocholithiasis, and granulomatous liver disease. U.S. 2014/187633 is directed to methods of treating and/or preventing non-alcoholic seatohepatitis (NASH) and/or primary biliary cirrhosis comprising administering to a subject in need thereof a pharmaceutical composition comprising eicosapentaenoic acid or a derivative thereof. The FXR agonist, obeticholic acid, which is a modified bile acid, is in phase III clinical trials for primary biliary cirrhosis. Use of this drug has been reported to be commonly associated with side effects such as pruritus.

Ursodeoxycholic acid (UDCA, Ursodiol) is the most frequently used treatment for primary biliary cirrhosis. It is one of the secondary bile acids, which are metabolic byproducts of intestinal bacteria. The drug is considered to assist in reducing the cholestasis and improves blood test results (liver function tests). However it has a minimal effect on symptoms and whether it improves prognosis is controversial. To relieve itching caused by bile acids in circulation, which would normally be removed by the liver, cholestyramine (a bile acid sequestrant) may be prescribed to primary biliary cirrhosis patients. The agent may assist in absorbing bile acids in the gut to be eliminated, rather than re-enter the blood stream. Alternative agents include stanozolol, naltrexone and rifampicin.

Obeticholic acid (OCA, Ocaliva) is a semi-synthetic bile acid analogue undergoing development in phase 2 and 3 studies for specific liver and gastrointestinal conditions. The FDA granted accelerated approval to Ocaliva on 27 May 2016 for the treatment of primary biliary cholangitis (PBC) in combination with ursodeoxycholic acid (UDCA) in adults with an inadequate response to UDCA, or as a single therapy in adults unable to tolerate UDCA. In addition, a phase 2 trial in NASH patients showed that administration of OCA reduced markers of liver inflammation and fibrosis and increased insulin sensitivity.

WO 2014/197738 and WO 2016/094570 relate to small molecule compounds, disclosed to be inhibitors of myofibroblast trans-differentiation and activation. Drugs and combinations suggested for the treatment of inter alia fatty liver were disclosed, for example, in WO 2016/112305 and EP2632925 (acetyl-CoA carboxylase inhibitors) as well as WO 2016/154258 (dual PPAR delta/gamma agonists). Some of the disclosed compounds were suggested to be used in combination with various other drugs.

Many patients do not respond to available treatments for fibrotic disorders, and long-term treatment is limited by toxicity and side effects. Therefore, a need remains for developing therapeutic modalities aimed at reducing fibrosis, especially hepatic fibrosis. The development of safe and effective treatments for established cirrhosis and portal hypertension and for attenuating fibrosis would be highly beneficial.

SUMMARY OF THE INVENTION

Fatty Acid Bile Acid Conjugates

Fatty acid bile salt conjugates, referred to also as Fatty Acid Bile Acid Conjugates (FABACs), are a family of synthetic molecules that may be used to improve conditions related to bile acids or cholesterol metabolism. FABACs are believed to lower blood cholesterol concentration, reduce liver fat levels and dissolve gallstones (Gilat et al., *Hepatology* 2003; 38: 436-442; and Gilat et al., *Hepatology* 2002; 35: 597-600). FABAC include 3β-arachidylamido-7α,12α-dihydroxy-5β-cholan-24-oic acid, also known as Aramchol™.

U.S. Pat. Nos. 6,384,024, 6,395,722, 6,589,946 disclose certain FABACs and their use in dissolving cholesterol gallstones in bile and treating arteriosclerosis. These and additional FABACs were disclosed in U.S. Pat. Nos. 7,501,403, 8,975,246 and 8,110,564 for use in treating fatty liver, in reducing blood cholesterol levels and in treating hyperglycemia, diabetes, insulin resistance and obesity. Further therapeutic uses of FABACs are disclosed in Safadi et al. (Clin Gastroenterol Hepatol. 2014 December; 12(12):2085-91) and in WO 2015/019358 and WO 2015/019359. Amine salts of certain FABACs are disclosed in WO 2015/083164.

The invention relates to the treatment, inhibition and reduction of fibrosis, including hepatic fibrosis. More specifically, embodiments of the invention provide compositions and methods useful for the treatment and inhibition of fibrotic disorders, hepato-fibrotic conditions associated with Non-Alcoholic Fatty Liver Disease (NAFLD) and Non-Alcoholic Steatohepatitis (NASH), employing the use of 3β-arachidylamido-7α,12α-dihydroxy-5β-cholan-24-oic acid (Aramchol™) or a pharmaceutically acceptable salt thereof. In other embodiments, the treatment and inhibition of hepato-fibrotic conditions caused by contact with hepatotoxic chemical substances or by mechanical obstruction is contemplated. In one embodiment, this invention provides a method for treating hepatic fibrosis in a human subject afflicted with hepatic fibrosis comprising administering to the subject a daily dose of between 400 mg and 900 mg of 3β-arachidylamido-7α, 12α-dihydroxy-5β-cholan-24-oic acid (Aramchol™), or a pharmaceutically acceptable salt thereof, said dose is administered in a dose regimen of at least twice a day, thereby treating hepatic fibrosis in said subject. In another embodiment, the daily dose amount is 600 mg or 800 mg. In another embodiment, each administered dose is 300 mg or 400 mg. In another embodiment, the Aramchol™ daily dose is 600 mg and it is administered twice a day wherein each administered dose is 300 mg. In another embodiment, 300 mg of Aramchol™ is administered to the subject every 12 hours. In another embodiment, the human subject is afflicted with Non-Alcoholic Fatty Liver Disease (NAFLD). In another embodiment, the human subject has a ballooning score of at least 1. In another embodiment, the human subject has an inflammation score of at least 1. In another embodiment, the human subject has a steatosis score of at least 1. In another embodiment, the human subject has a ballooning score of at least 1, an inflammation score of at least land a steatosis score of at least 1. In another embodiment, the human subject is afflicted with Diabetes Mellitus type II or pre-diabetes. In another embodiment, the human subject is afflicted with Non-Alcoholic Steatohepatitis (NASH). In another embodiment, the human subject is not afflicted with Non-Alcoholic Steatohepatitis (NASH).

In another embodiment, the method further comprises lack of worsening of the subject's NAFLD as defined by Activity (NAS) score. In another embodiment, the method further comprises lack of worsening of the subject's Steatosis, Activity, and Fibrosis (SAF) Activity score. In another embodiment, the method further comprises reduction of liver fat in said subject. In another embodiment, the method further comprises improvement in subject's Steatosis. In another embodiment, the method further comprises improvement in subject's ballooning. In another embodiment, the method further comprises NAFLD resolution. In another embodiment, the method further comprises NAFLD resolution without worsening of fibrosis. In another embodiment, the method further comprises reduction of fibrosis without NAFLD worsening. In another embodiment, the method further comprises reduction of ALT levels in said subject. In another embodiment, the method further comprises reduction of AST levels in said subject. In another embodiment, the method further comprises reduction of HbA1c levels in said subject. In another embodiment, the method further comprises lack of subject's progression to Cirrhosis. In another embodiment, the method further comprises inhibiting progression of Non-Alcoholic Fatty Liver Disease (NAFLD) and/or Non-Alcoholic Steatohepatitis (NASH). In another embodiment, the human subject is afflicted with Non-Alcoholic Steatohepatitis (NASH) and the method further comprises inhibiting the progression of NASH in said subject. In another embodiment, the human subject is afflicted with Non-Alcoholic Steatohepatitis (NASH) and the method further comprises NASH resolution in the subject.

In one embodiment, this invention provides a method for inhibiting the development of hepatic fibrosis in a human subject afflicted with Non-Alcoholic Fatty Liver Disease and having a fibrosis score of zero comprising administering to the subject a daily dose of between 400 mg and 900 mg of 3β-arachidylamido-7α, 12α-dihydroxy-5β-cholan-24-oic acid (Aramchol™), or a pharmaceutically acceptable salt thereof, said dose is administered in a dose regimen of at least twice a day, thereby inhibiting the development of hepatic fibrosis in said subject. In another embodiment, the daily dose amount is 600 mg or 800 mg. In another embodiment, each administered dose is 300 mg or 400 mg. In another embodiment, the Aramchol™ daily dose is 600 mg and it is administered twice a day wherein each administered dose is 300 mg. in another embodiment, 300 mg of Aramchol™ is administered to the subject every 12 hours. In another embodiment, the human subject has a NAFLD Activity (NAS) Score of at least 4, at least 5, at least 6, or at least 7. In another embodiment, the human subject has a ballooning score of at least 1. In another embodiment, the human subject has an inflammation score of at least 1. In another embodiment, the human subject has a steatosis score of at least 1. In another embodiment, the human subject has a ballooning score of at least 1, an inflammation score of at least 1, and a steatosis score of at least 1. In another embodiment, the human subject is afflicted with Diabetes Mellitus type II or pre-diabetes. In another embodiment, the human subject is afflicted with Non-Alcoholic Steatohepatitis (NASH). In another embodiment, the human subject is not afflicted with Non-Alcoholic Steatohepatitis (NASH).

In another embodiment, the method further comprises lack of worsening of the subject's NAFLD as defined by Activity (NAS) score. In another embodiment, the method further comprises lack of worsening of the subject's Steatosis, Activity, and Fibrosis (SAF) Activity score. In another embodiment, the method further comprises reduction of liver fat in said subject. In another embodiment, the method further comprises improvement in subject's Steatosis. In another embodiment, the method further comprises improvement in subject's ballooning. In another embodiment, the method further comprises NAFLD resolution. In another embodiment, the method further comprises NAFLD resolution without worsening of fibrosis. In another embodiment, the method further comprises reduction of fibrosis without NAFLD worsening. In another embodiment, the method further comprises reduction of ALT levels in said subject. In another embodiment, the method further comprises reduction of AST levels in said subject. In another embodiment, the method further comprises reduction of HbA1c levels in said subject. In another embodiment, the method further comprises lack of subject's progression to Cirrhosis. In another embodiment, the method further comprises inhibiting progression of Non-Alcoholic Fatty Liver Disease (NAFLD) and/or Non-Alcoholic Steatohepatitis (NASH). In another embodiment, the human subject is afflicted with Non-Alcoholic Steatohepatitis (NASH) and the method further comprise inhibiting the progression of NASH in said subject. In another embodiment, the human subject is afflicted with Non-Alcoholic Steatohepatitis (NASH) and the method further comprises NASH resolution in the subject.

In one embodiment, this invention provides a method for treating fibrosis other than hepatic fibrosis in a human subject afflicted with fibrosis comprising administering to the subject a daily dose of between 400 mg and 900 mg of 3β-arachidylamido-7α, 12α-dihydroxy-5β-cholan-24-oic acid (Aramchol™), or a pharmaceutically acceptable salt thereof, said dose is administered in a dose regimen of at least twice a day, thereby treating fibrosis in said subject, wherein said fibrosis is being caused by a factor selected from the group consisting of pulmonary fibrosis, heart fibrosis, kidney fibrosis, dermal fibrosis, ocular fibrosis, mucosal fibrosis, fibrosis of the central nervous system, fibrosis in bone or bone marrow, fibrosis in an endocrine organ, fibrosis in the gastro-intestinal system, mediastinal fibrosis, postfibrinous fibrosis, proliferative fibrosis, retroperitoneal fibrosis, pancreatic fibrosis, or fibrosis associated with an autoimmune disease.

In another embodiment, the methods according to this invention further comprise administering a therapeutically effect amount of a pharmaceutical composition comprising at least one compound selected from the group consisting of:

a) ethyl eicosapentanoate (EPA-E), eicosapentaenoic acid (EPA) and its pharmaceutically acceptable amides, salts, esters and phospholipids;

b) an an inhibitor of Acetyl-CoA carboxylase (ACC) alone, or in combination with one or more additional therapeutic agents;

c) pioglitazone hydrochloride or an enantiopure deuterium-enriched pioglitazone; d) a peroxisome proliferator activated receptor (PPAR) delta and gamma dual agonists; and e) angiotensin II receptor antagonists, angiotensin converting enzyme (ACE) inhibitors, caspase inhibitors, cathepsin B inhibitors, CCR2 chemokine antagonists, CCR5 chemokine antagonists, chloride channel stimulators, cholesterol solubilizers, diacylglycerol O-acyltransferase 1 (DGATI) inhibitors, dipeptidyl peptidase IV (DPPIV) inhibitors, farnesoid X receptor (FXR) agonists such as obeticholic acid and Px-104, FXR/TGR5 dual agonists, galectin-3 inhibitors such as LIPC-1010 and GR-MD-02, glucagon-like peptide (GLPI) agonists, glutathione precursors, hepatitis C virus NS3 protease inhibitors, HMG CoA reductase inhibitors, II~-hydroxysteroid dehydrogenase (II~-HSD I) inhibitors, IL-I~ antagonists, IL-6 antagonists, IL-I 0 agonists, IL-I 7 antagonists, ileal sodium bile acid cotransporter inhibitors, leptin analogs, 5-lipoxygenase inhibitors, LPL gene stimulators, lysyl oxidase homolog 2 (LOXL2) inhibitors, PDE3 inhibitors, PDE4 inhibitors, phospholipase C (PLC) inhibitors, PPARa agonists, PPAR gamma agonists such as rosiglitazone and pioglitazone, metformin, pentoxyfylline, vitamin E, selenium, omega-3 fatty acids and betaine, PPAR8 agonists, Rho associated protein kinase 2 (ROCK2) inhibitors, sodium glucose transporter-2 (SGLT2) inhibitors, stearoyl CoA desaturaseI inhibitors, thyroid hormone receptor-agonists, tumor necrosis factor a (TNFa) ligand inhibitors, transglutaminase inhibitors, transglutaminase inhibitor precursors, PTPib inhibitors, ASKI inhibitors, and vascular adhesion protein-1 inhibitors such as PXS4728A, metformin, GR-MD-02, cysteamine bitartrate, simtuzumab, emricasan, GFT-505, CER-002, KD3010, KD3020, MBX8025, LUM002, RP-103, and cenicriviroc.

BRIEF DESCRIPTION OF THE DRAWINGS

FIG. 1A—saline control; FIG. 1B—treatment with TAA (20 mg/100 gr body weight) twice per week during 10 weeks; FIG. 1C—treatment with TAA and Aramchol™ 1 mg/kg; FIG. 1D—treatment with TAA and Aramchol™ 5 mg/kg.

FIG. 2A—averaged fibrotic score (TAA—black, Aramchol™—white, OCA—gray); FIG. 2B—representative samples (TAA only—left; TAA and Aramchol™ 1 mg/kg—middle; TAA and Aramchol™ 5 mg/kg—right).

FIG. 6A—histology staining using Sudan III; FIG. 6B—quantification of Sudan III stained cells.

FIG. 7A—histology staining—F4/80 and CD64; FIG. 7B—quantification of CD64 positive cells and FIG. 7C quantification of F4/80 positive cells.

FIG. 8A—histology staining using sirius red; FIG. 8B—quantification of sirius red stained cells.

FIG. 10A—quantification of metabolites in liver of control (grey) and Aramchol™-treated (black) 0.1 MCD mice; FIG. 10B—schematic of relevant liver biochemical pathway.

FIG. 16A is the mean absolute change from baseline in liver fat; FIG. 16B is the MRI Responders Analysis: Reduction ≥5% absolute change from baseline. Liver function was significantly reduced vs. placebo, Reduction of ≥5% absolute change displays a dose response pattern.

FIG. 17A is the Ballooning Improvement (≥1 point); and FIG. 17B is the Ballooning 0 at end of study. A statistically significant effect on ballooning was demonstrated with Aramchol™ 600 mg.

FIG. 18A is NASH Resolution without Worsening of Fibrosis; and FIG. 18B is the NASH Resolution. Significantly more patients treated with Aramchol™ 600 mg showed NASH resolution without worsening of fibrosis with a dose response pattern.

FIG. 19A depicts the fibrosis improvement (≥1 stage) without worsening of NASH; and FIG. 19B depicts the progression to Cirrhosis. More patients showed fibrosis improvement without worsening of NASH with a dose response pattern. Less patients progressed to cirrhosis with Aramchol™ 600 mg.

FIG. 20A depicts the change from baseline in ALT levels (U/L); and FIG. 20B depicts the change from baseline in AST levels (U/L). Both 400 mg, and 600 mg doses significantly reduced ALT, AST levels in subjects vs. placebo in a dose response manner.

FIG. 22A and FIG. 22B depict the Western Blot and the densitometry respectively of downregulated SCD-1 protein in HSCs treated with Aramchol™ for 24 or 48 hrs. (N=3) *$p<0.05$, $p<0.01$, *$p<0.001$.

DETAILED DESCRIPTION OF THE INVENTION

Aramchol™

Figure 1A:
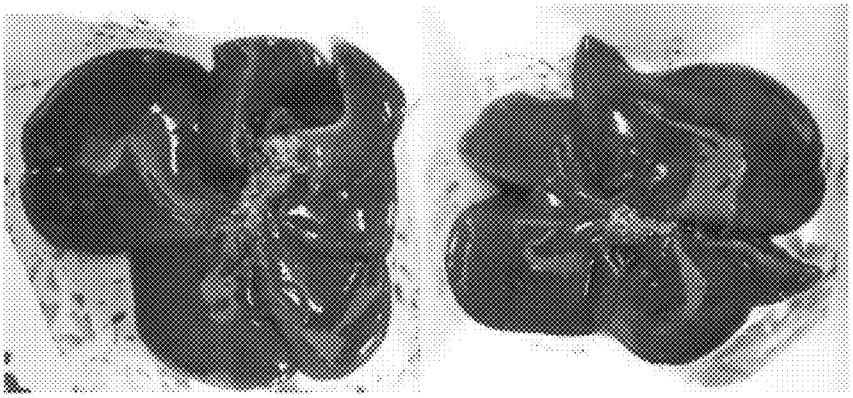
FIGS. 1A-1D demonstrate the effect of Aramchol™ on liver cirrhosis by macroscopic evaluation.
Figure 1B:
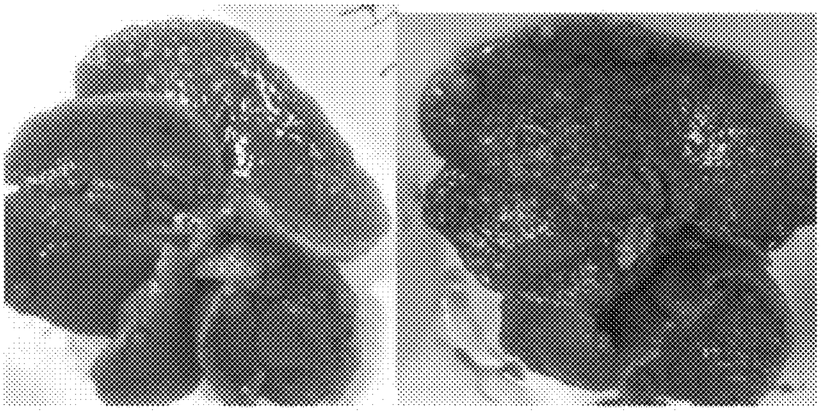
Figure 1C:
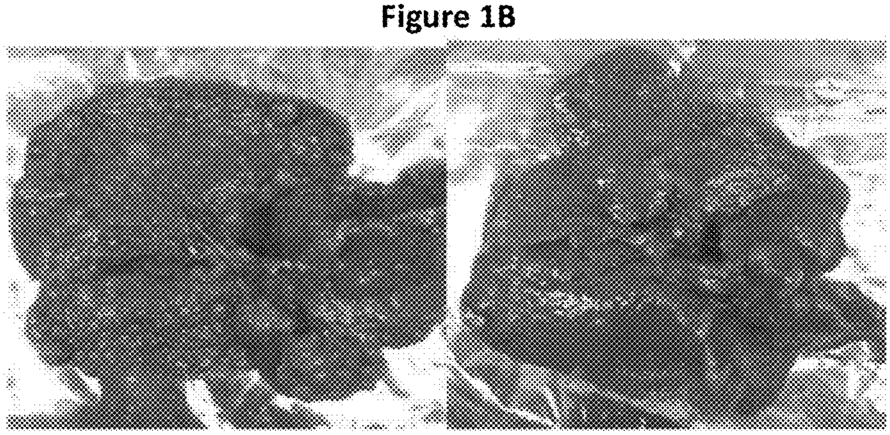
Figure 1D:
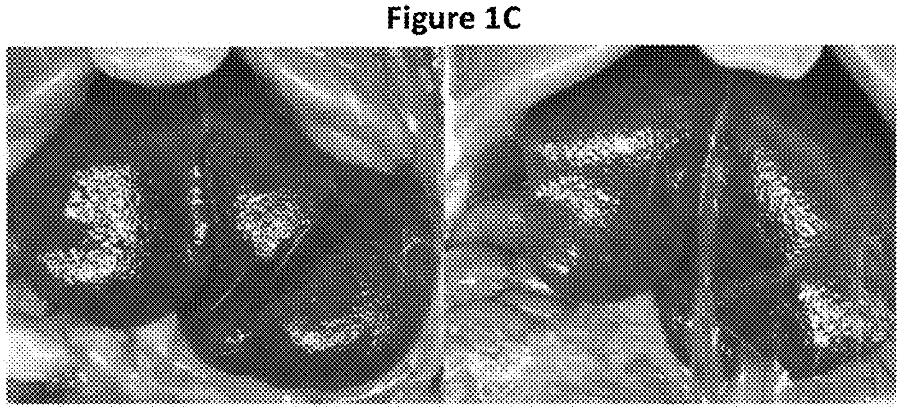
Figure 2A:
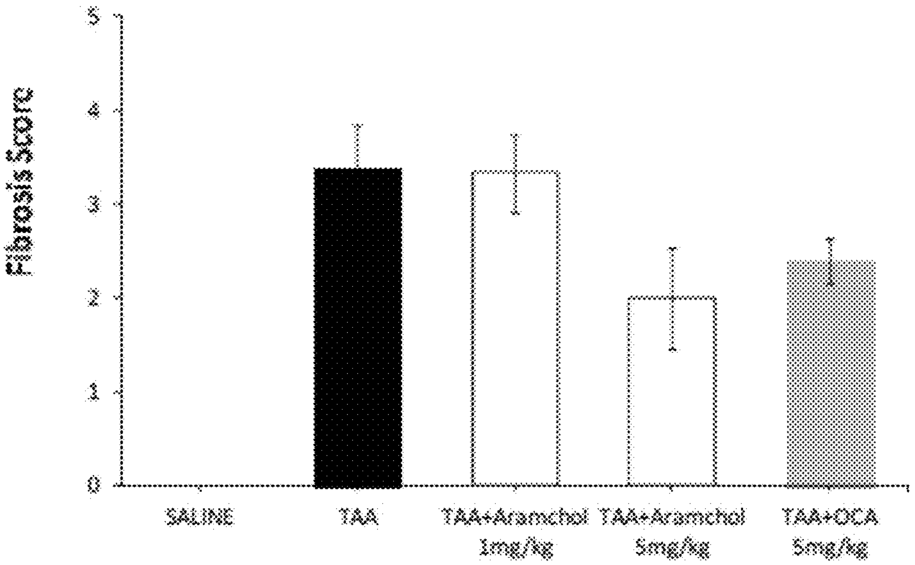
FIGS. 2A-2B demonstrate the effect of Aramchol™ on liver fibrosis by microscopic evaluation (following Masson Goldner staining).
Figure 2B:
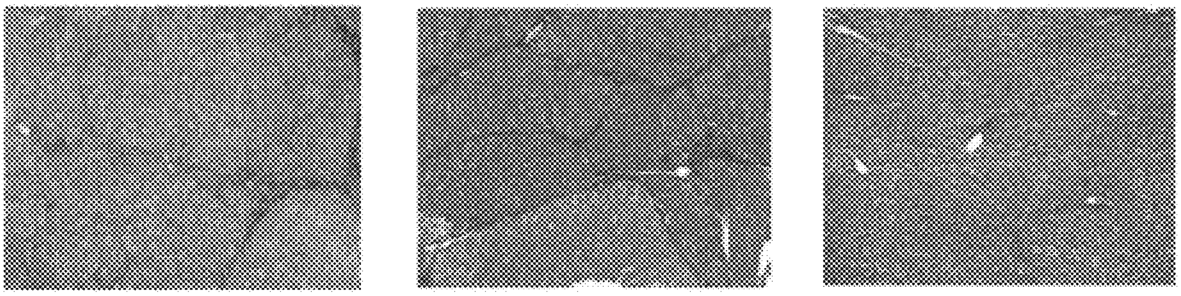

According to an embodiment of the invention, the combinations, compositions, methods and packages of the invention may comprise Aramchol™ in its free acid form. According to an embodiment of the invention, Aramchol™ is in its salt form. The salt may be an amine-based salt. The amine-based salt may be selected from the group consisting of meglumine, lysine and tromethamine salts.

Other embodiments of the invention relate to compositions, methods and packages employing the use of a Fatty Acid Bile Acid Conjugate (FABAC), or salts thereof. According to some embodiments, the FABAC is of Formula I:

$$W\text{-}X\text{-}G \qquad (I)$$

wherein G represents a bile acid or a bile salt radical thereof, W represents one or two fatty acid radicals having 6-22 carbon atoms; and X represents a bonding member selected from the group consisting of: a heteroatom, a direct C—C bond and a C═C bond; each possibility represents a separate embodiment of the present invention.

According to some embodiments, the bonding member is selected from the group consisting of: NH, P, S, O and a direct C—C or C═C bond; each possibility represents a separate embodiment of the present invention. According to some embodiments, the bonding member is NH.

According to some embodiments, each of said one or two fatty acid radicals is a radical of a fatty acid selected from the group consisting of: arachidylic acid, stearic acid, behenic acid, palmitic acid, arachidonic acid, eicosapentaenoic acid and oleic acid; each possibility represents a separate embodiment of the present invention. According to some embodiments, said one or two fatty acid radicals are radicals of arachidylic acid; each possibility represents a separate embodiment of the present invention.

According to some embodiments, W represents two fatty acid radicals, each independently comprises 6-22 carbon atoms; and wherein each of said fatty acid radicals is independently bound to a bonding member X selected from the group consisting of: a heteroatom, a direct C—C bond and a C═C bond. According to some embodiments, W represents a single fatty acid radical.

According to some embodiments, the bile acid is selected from the group consisting of: cholic acid, ursodeoxycholic acid, chenodeoxycholic acid, deoxycholic acid, lithocholic acid and derivatives thereof, each possibility represents a separate embodiment of the present invention. In another embodiment the bile acid is cholic acid, chenodeoxycholic acid, or deoxycholic acid. In another embodiment the bile acid is other than ursodeoxycholic acid and lithocholic acid. According to some embodiments, the bile acid is cholic acid.

Indications.

The invention is based, in part, on the surprising discovery that Aramchol™ exerts a potent anti-fibrotic effect, independent of its reported activities on fatty liver and steatosis, and reduces and inhibits the development of fibrosis in various experimental models. Specifically, treatment with Aramchol™ (5 mg/kg) significantly inhibited the development of toxin-induced cirrhosis, necrosis and liver fibrosis in an in vivo thioacetamide (TAA) model. Aramchol™ was also found to be unexpectedly superior to obaticholic acid (OCA), which did not induce statistically significant reduction in these parameters under the tested experimental conditions. In addition, Aramchol™ significantly reduced COL1A1 expression in LX-2 human hepatic stellate cells via PPARγ up-regulation. Aramchol™ was surprisingly found to be effective in reversing established fibrosis, and in reducing the production of collagen specifically in stellate cells.

Thus, independently from its reported activities on liver metabolism in subjects with NAFLD, Aramchol™ is surprisingly found herein to be effective in the treatment of new patient populations and patient subpopulations, such as in the treatment of patients with NAFLD or NASH who have not yet developed fibrosis. In addition, Aramchol™ was found to be effective in the treatment of non-hepatic fibrosis and various conditions characterized by fibrosis of environmental and/or immune etiology, hepatic fibrosis in patients with NAFLD or NASH, treatment of hepatic fibrosis in patients with NAFLD or NASH and advanced fibrosis (i.e. stage 2 or stage 3 fibrosis), treatment of hepatic fibrosis in patient with NAFLD or NASH who have cirrhosis (i.e. stage 4 fibrosis), treatment of hepatic fibrosis caused by contact with drugs, toxins or surgery, and specifically in alleviating hepatic cirrhosis, treatment of fibrosis without worsening of NAFLD or NASH, treatment of fibrosis without progression to Cirrhosis. The invention advantageously provides for the treatment of these new patient populations with enhanced efficacy and/or safety and minimized side effects.

In various embodiments, the treated fibrosis is pulmonary fibrosis (e.g. idiopathic pulmonary fibrosis, diffuse interstitial pulmonary fibrosis, pleural fibrosis and fibrosis associated with asthma, fibrous dysplasia, cystic fibrosis), heart fibrosis (e.g. endomyocardial fibrosis and fibrosis associated with cardiovascular disease), kidney fibrosis (e.g. associated with renal failure), dermal fibrosis (e.g. keloid), ocular fibrosis, mucosal fibrosis, fibrosis of the central nervous system, fibrosis in bone or bone marrow, fibrosis in an endocrine organ (e.g. pancreas), fibrosis in the gastro-intestinal system, mediastinal fibrosis, postfibrinous fibrosis, proliferative fibrosis, retroperitoneal fibrosis, pancreatic fibrosis, or fibrosis associated with an autoimmune disease (e.g. systemic lupus erythematosus (SLE), Sjogren syndrome, or diffuse systemic sclerosis with scleroderma).

For example, endomyocardial fibrosis is an idiopathic type of myocardiopathy that is endemic in various parts of Africa and rarely in other areas, characterized by cardiomegaly, marked thickening of the endocardium with dense white fibrous tissue that may extend to involve the inner myocardium, and by congestive heart failure.

Idiopathic pulmonary fibrosis (e.g. diffuse idiopathic interstitial fibrosis, diffuse interstitial pulmonary fibrosis) is a chronic inflammatory progressive fibrosis of the pulmonary alveolar walls, with steadily progressive dyspnea, resulting in death from oxygen lack or right heart failure. Most cases are of unknown origin, although some are thought to result from pneumoconiosis, hypersensitivity pneumonitis, scleroderma, and other diseases. In some embodiments, pulmonary fibrosis is induced (in order to study treatment thereof) via agents such as bleomycin (BLM).

Mediastinal fibrosis is characterized by development of hard white fibrous tissue in the upper portion of the mediastinum, sometimes obstructing the air passages and large blood vessels; called also fibrosing or fibrous mediastinitis.

Pleural fibrosis is characterized by fibrosis of the visceral pleura so that part or all of a lung becomes covered with a plaque or a thick layer of nonexpansible fibrous tissue. The more extensive form is called fibrothorax.

Postfibrinous fibrosis occurs in tissues in which fibrin has been deposited.

Proliferative fibrosis refers to a condition in which the fibrous elements continue to proliferate after the original causative factor has ceased to operate.

Retroperitoneal fibrosis (Ormond disease, periureteral fibrosis) is characterized by deposition of fibrous tissue in the retroperitoneal space, producing vague abdominal discomfort, and often causing blockage of the ureters, with resultant hydronephrosis and impaired renal function, which may result in renal failure.

According to an embodiment of the invention, a method is provided for treating fibrosis selected from the group consisting of: pulmonary fibrosis (e.g. idiopathic pulmonary fibrosis, diffuse interstitial pulmonary fibrosis, pleural fibrosis and fibrosis associated with asthma, fibrous dysplasia, cystic fibrosis), heart fibrosis (e.g. endomyocardial fibrosis and fibrosis associated with cardiovascular disease), kidney fibrosis (e.g. associated with renal failure), dermal fibrosis (e.g. keloid), ocular fibrosis, mucosal fibrosis, fibrosis of the central nervous system, fibrosis in bone or bone marrow, fibrosis in an endocrine organ (e.g. pancreas), fibrosis in the gastro-intestinal system, mediastinal fibrosis, postfibrinous fibrosis, proliferative fibrosis, retroperitoneal fibrosis, pancreatic fibrosis, fibrosis associated with an autoimmune disease (e.g. systemic lupus erythematosus (SLE), Sjogren syndrome, or diffuse systemic sclerosis with scleroderma) in a human subject afflicted with said condition comprising adninistering to the subject 3β-arachidylamido-7α, 12α-dihydroxy-5β-cholan-24-oic acid (Aramchol), or a pharmaceutically acceptable salt thereof, thereby treating said condition in said subject. In another embodiment of the invention the fibrosis treated is selected from the group consisting of: pulmonary fibrosis, heart fibrosis, kidney fibrosis, dermal fibrosis and fibrosis in the gastro-intestinal system. In another embodiment, the aramchol is aramchol meglumine. In another embodiment, the aramchol is administered to the subject once or twice a day. In another embodiment, the aramchol is administered in a dosage of 400-900 mg per day. Each possibility represents a separate embodiment of the invention.

In various embodiments, the human subject being treated is afflicted with Non-Alcoholic Steatohepatitis (NASH). In some embodiments, the Aramchol™ daily dose is between about 400 mg and 900 mg. In some embodiments, the Aramchol™ is administered in a dose regimen of at least twice a day. In some embodiments, each Aramchol™ dose administered to the subject is 300, 400, 450, 500, 550, 600, 650, 700, 750, 800, 850 or 900 mg once, twice or three times a day; each represent a separate embodiment according to this invention. In one embodiment, the Aramchol™ is administered to the subject, twice daily, in doses of 300 mg each. In one embodiment, the Aramchol™ is administered to the subject, three times daily, in doses of 300 mg each. In one embodiment, the Aramchol™ is administered to the subject, twice daily, in doses of 400 mg each. In one embodiment, the Aramchol™ is administered to the subject, three times daily, in doses of 400 mg each. This invention also provides a method for treating hepatic fibrosis in a human subject afflicted with hepatic fibrosis comprising administering to the subject greater than 300 μg per day of Arancholm, or a pharmaceutically acceptable salt thereof, thereby treating hepatic fibrosis in said subject. In an embodiment the human subject being treated is afflicted with Non-Alcoholic Fatty Liver Disease (NAFLD). In an embodiment the human subject being treated is afflicted with Non-Alcoholic Fatty Liver Disease (NAFLD). In an embodiment the human subject being treated is afflicted with Non-Alcoholic Steatohepatitis (NASH). In some embodiments, the Aramchol™ daily dose is between about 400 mg and 900 mg. In some embodiments, the Aramchol™ is administered in a dose regimen of at least twice a day. In some embodiments, each Aramchol™ dose administered to the subject is 300, 400, 450, 500, 550, 600, 650, 700, 750, 800, 850 or 900 mg once, twice or three times a day; each represent a separate embodiment according to this invention. In one embodiment, the Aramchol™ is administered to the subject, twice daily, in doses of 300 mg each. In one embodiment, the Aramchol™ is administered to the subject, three times daily, in doses of 300 mg each. In one embodiment, the Aramchol™ is administered to the subject, twice daily, in doses of 400 mg each. In one embodiment, the Aramchol™ is administered to the subject, three times daily, in doses of 400 mg each. This invention also provides a method for treating hepatic fibrosis in a human subject afflicted with hepatic fibrosis comprising administering to the subject greater than 300 mg per day of 3β-arachidylamido-7α, 12α-dihydroxy-5β-cholan-24-oic acid (Aramchol™), or a pharmaceutically acceptable salt thereof, thereby treating hepatic fibrosis in said subject. The exposure and absorption of a drug is limited by its bioavailability, which is usually determined by the solubility and permeability or the drug. It is herein demonstrated based on modeling and simulations, that a two-dose regimen (BID) of Aramchol™ i.e., administration of a given amount of Aramchol™ (e.g., 600 mg) in two doses (i.e., 300 mg each), twice daily, instead of one dose (i.e., 600 mg), once daily, is expected to increase the bioavailability of the drug and accordingly its exposure. It is therefore suggested that splitting the dose of Aramchol™ will be beneficial to the subject. Therefore, according to this invention, the daily amount of Aramchol™ is administered to a subject in a split dose regimen, including but not limited to: a two doses regimen (twice daily, BID), a three doses regimen (three times daily, TID), a four-dose regimen, or a five-dose regimen. Accordingly, this invention provides a method for treating hepatic fibrosis in a human subject afflicted with hepatic fibrosis comprising administering to the subject a daily dose of 100, 300, 400, 600, or 900 mg of 3β-arachidylamido-7α, 12α-dihydroxy-5β-cholan-24-oic acid (Aramchol™), or a pharmaceutically acceptable salt thereof, thereby treating hepatic fibrosis in said subject. In some embodiments, the Aramchol™ daily dose is between about 400 mg and 900 mg. In some embodiments, the Aramchol™ is administered in a dose regimen of at least twice a day. In some embodiments, each Aramchol™ dose administered to the subject is 300, 400, 450, 500, 550, 600, 650, 700, 750, 800, 850 or 900 mg once, twice or three (3) times a day; each represent a separate embodiment according to this invention. In yet another embodiment, a dose of 300 mg of Aramchol™ is administered twice daily. In yet another embodiment, a dose of 400 mg of Aramchol™ is administered twice a day. In yet another embodiment, a dose of 300 mg of Aramchol™ is administered three times a day: the human subject being treated is afflicted with Non-Alcoholic Fatty Liver Disease (NAFLD).

the human subject being treated is afflicted with Non-Alcoholic Steatohepatitis (NASH).

the human subject is afflicted with NAFLD but not afflicted with Non-Alcoholic Steatohepatitis (NASH). the human subject has a NAFLD Activity (NAS) Score of at least 4. the human subject has a NAFLD Activity (NAS) Score of at least 5, at least 6, or at least 7. the human subject has a ballooning score of at least 1, an inflammation score of at least 1, and a steatosis score of at least 1. In various embodiments, the human subject has ballooning. In other embodiments, the human subject has high levels of ALT, AST, HbA1c or any combination thereof. In other embodiments, the human subject afflicted with fibrosis has progressed to Cirrhosis.

the human subject is afflicted with NAFLD but not afflicted with Non-Alcoholic Steatohepatitis (NASH).

the human subject is afflicted with Diabetes Mellitus type II or pre-diabetes. One of the following 3 criteria is needed for pre-Diabetes: Fasting Plasma Glucose >100 mg/dl (5.5 mmol/l) or 2hPG following 75 g OGTT >140 (7.8 mmol/l) mg/dl or HbA1c >5.7%. HbA1c can be repeated at Investigator's discretion.

the subject's hepatic fibrosis is stage 2, 3, or 4 fibrosis. the subject's hepatic fibrosis is stage 1 fibrosis. the subject's hepatic fibrosis is stage 1a, stage 1b, or stage 1c fibrosis.

the human subject has a diet that is high fat and high calorie. As used herein, a high fat, high calorie diet contains at least 4000 calories per day, of which approximately 50% comes from fat. the human subject is resistant to lifestyle intervention. the human subject is resistant to diet intervention. the human subject is naïve to naïve to Aramchol™ treatment. the subject is naïve to NAFLD treatment.

The invention further relates to the treatment and reduction of fibrosis, specifically liver fibrosis. The invention provides compositions and methods useful for the treatment of hepatic cirrhosis, portal hypertension, and hepato-fibrotic conditions caused by contact with hepatotoxic chemical substances or by mechanical obstruction. Compositions and methods according to the invention employ the use of 3β-arachidylamido-7α,12α-dihydroxy-5β-cholan-24-oic acid (Aramchol™) or a pharmaceutically acceptable salt thereof.

In one aspect, there is provided a method for the treatment of hepatic fibrosis in a subject in need thereof, the hepatic fibrosis being caused by contact with a hepatotoxic chemical substance or by mechanical obstruction, comprising administering to the subject an effective amount of Aramchol™, or a pharmaceutically acceptable salt thereof, thereby treating hepatic fibrosis in said subject.

In another aspect there is provided a method for the treatment of hepatic fibrosis in a subject in need thereof, comprising administering to the subject an effective amount of Aramchol™ or a pharmaceutically acceptable salt thereof, with the proviso that the fibrosis is associated with a disorder other than non-alcoholic liver disease and non-alcoholic steatohepatitis.

In another aspect there is provided a method for treating or inhibiting a disorder selected from the group consisting of hepatic cirrhosis and portal hypertension in a subject in need thereof, comprising administering to the subject an effective amount of Aramchol™ or a pharmaceutically acceptable salt thereof.

In another aspect there is provided a method of treating or inhibiting a fibrotic disease or condition in a subject in need thereof, comprising administering to the subject an effective amount of Aramchol™ or a pharmaceutically acceptable salt thereof, thereby treating or inhibiting the disease or condition in the subject, wherein said disease or condition is selected from the group consisting of: alcoholic liver disease, viral hepatitis, parasitic hepatitis, drug-induced hepatitis, toxin-induced hepatitis, primary biliary cirrhosis and congenital hepatic fibrosis.

Known indications suggested for FABAC treatment include those disclosed in U.S. Pat. Nos. 6,384,024, 6,395,722, 6,589,946, 7,501,403, 8,110,564 and 8,975,246, as detailed herein, and are explicitly excluded in an embodiment. In some embodiments, the subject to be treated by the methods of the invention is not afflicted with an additional medical condition.

Further, according to an aspect of the present invention, there is provided a method for the treatment of hepatic fibrosis in a subject in need thereof, the hepatic fibrosis being caused by contact with a hepatotoxic chemical substance or by mechanical obstruction, comprising administering to the subject an effective amount of Aramchol™ or a pharmaceutically acceptable salt thereof, thereby treating hepatic fibrosis in said subject.

According to embodiments of the present invention, the hepatic fibrosis is caused by a factor selected from the group consisting of chronic alcoholism, malnutrition, hemochromatosis, passive congestion, exposure to poisons or toxins, exposure to drugs, immune reactions, genetically determined sensitivities to a certain substance and infections.

In other embodiments, the hepatic fibrosis is caused by a factor selected from the group consisting of viral hepatitis, syphilis and a parasitic infection. In a particular embodiment, said parasitic infection is selected from the group consisting of Schistosomiasis *mansoni* and *S. japonica*. In another particular embodiment, the viral hepatitis is associated with is chronic hepatitis C infection.

According to another embodiment of the present invention, there is provided a method for the treatment of hepatic fibrosis in a subject, comprising administering to the subject an effective amount of Aramchol™ or a pharmaceutically acceptable salt thereof, with the proviso that the fibrosis is associated with a disorder other than non-alcoholic liver disease and non-alcoholic steatohepatitis.

In various embodiments, the subject is not diagnosed with fatty liver. In certain embodiments, the fibrosis is associated with a disorder selected from the group consisting of autoimmune hepatitis, storage or metabolism hepatic disorders, congenital hepatic fibrosis, infection, primary biliary cirrhosis and primary sclerosing cholangitis; each possibility represents a separate embodiment of the invention. In a particular embodiment, the fibrosis is associated with congenital hepatic fibrosis, a developmental disorder of the liver, marked by formation of irregular broad bands of fibrous tissue containing multiple cysts formed by disordered terminal bile ducts, resulting in vascular constriction and portal hypertension.

Non-limiting examples for diseases associated with storage or metabolism abnormalities that are characterized by hepatic fibrosis (storage or metabolism hepatic disorders) include al-Antitrypsin deficiency, copper storage diseases (e.g., Wilson disease), fructosemia, galactosemia, glycogen storage diseases (especially types III, IV, VI, IX, and X), iron-overload syndromes (hemochromatosis), lipid abnormalities (e.g., Gaucher disease), peroxisomal disorders (e.g., Zellweger syndrome), and tyrosinemia; each possibility represents a separate embodiment of the invention.

Non-limiting examples for infections characterized by liver fibrosis include bacterial infections (e.g., brucellosis), parasitic infections (e.g., echinococcosis), and viral infections (e.g., viral hepatitis including, but not limited to chronic hepatitis B or C); each possibility represents a separate embodiment of the invention. In a particular embodiment, the infection is chronic hepatitis C infection.

According to yet further embodiments, the fibrosis is associated with contact with a hepatotoxic chemical substance, including, but not limited to alcohol, amiodarone, chlorpromazine, isoniazid, methotrexate, methyldopa, oxyphenisatin, and tolbutamide; each possibility represents a separate embodiment of the invention. In a particular embodiment, said substance is alcohol.

According to further embodiments, the fibrosis is associated with mechanical obstruction, e.g. scarring due to prior liver surgery.

In another embodiment the disorder is associated with COL1A1 and/or PPAR-γ dysregulation in hepatic stellate calls. In a particular embodiment, said disorder is associated with COL1A1 up-regulation and PPAR-γ down-regulation in hepatic stellate calls of said subject.

In another aspect, there is provided a method for treating or inhibiting a disorder selected from the group consisting of hepatic cirrhosis and portal hypertension in a subject in need thereof, comprising administering to the subject an effective amount of Aramchol™ or a pharmaceutically acceptable salt thereof.

In another embodiment, said fibrosis is manifested by portal hypertension and/or hepatic cirrhosis. In a particular embodiment, said fibrosis is manifested by hepatic cirrhosis.

In one embodiment, the disorder is hepatic cirrhosis. In another embodiment, said disorder is portal hypertension. According to some embodiments, the methods of the invention advantageously provide for treating an existing condition of hepatic cirrhosis and/or portal hypertension. Thus, according to some embodiments, the method comprises determining whether said subject is afflicted with of hepatic cirrhosis and/or portal hypertension, and administering said Aramchol™ or a pharmaceutically acceptable salt thereof to a subject afflicted with of hepatic cirrhosis and/or portal hypertension. According to other embodiments, said of hepatic cirrhosis and/or portal hypertension is associated with a disorder as described herein; each possibility represents a separate embodiment of the invention.

In other embodiments, the method is used for inhibiting or preventing a symptom of hepatic cirrhosis and/or portal hypertension. According to various specific embodiments, the method is used for inhibiting or preventing a symptom of portal hypertension, including, but not limited to variceal bleeding, ascites, and portosystemic encephalopathy. In other particular embodiments, the method is used for inhibiting or preventing a symptom of hepatic cirrhosis, including, but not limited to hepatic insufficiency and fatal liver failure; each possibility represents a separate embodiment of the invention.

In various embodiments, the invention provides a method of treating or inhibiting a fibrotic disease or condition in a subject in need thereof, comprising administering to the subject an effective amount of Aramchol™ or a pharmaceutically acceptable salt thereof, thereby treating or inhibiting the disease or condition in the subject, wherein said disease or condition is selected from the group consisting of: alcoholic liver disease, viral hepatitis, parasitic hepatitis, drug-induced hepatitis, toxin-induced hepatitis, primary biliary cirrhosis and congenital hepatic fibrosis. In another embodiment, said disease or condition is selected from the group consisting of: alcoholic liver disease, parasitic hepatitis, drug-induced hepatitis, and toxin-induced hepatitis; each possibility represents a separate embodiment of the invention. In another embodiment, said disease or condition is chronic. In some embodiments, the Aramchol™ daily dose is between about 400 mg and 900 mg. In some embodiments, the Aramchol™ is administered in a dose regimen of at least twice a day. In some embodiments, each Aramchol™ dose administered to the subject is 300, 400, 450, 500, 550, 600, 650, 700, 750, 800, 850 or 900 mg once, twice or three (3) times a day; each represent a separate embodiment according to this invention.

Administration and Dosage Form

According to some embodiments, the compound to be administered (e.g. Aramchol™) is in the form of a composition (referred to as the composition of the invention) comprising a therapeutically effective amount of at least one of said compound. As used herein, the term “effective amount” means an amount of compound that is capable of reducing and/or attenuating a disorder or symptom as described herein. The specific dose of a compound administered according to this invention will, of course, be determined by the particular circumstances surrounding the case including, for example, the compound administered, the route of administration, the physiological state of the subject, and the severity of the condition being treated.

This invention provides a medicament comprising greater than 300 mg of 3β-arachidylamido-7α, 12α-dihydroxy-5β-cholan-24-oic acid (Aramchol™) for use in administration to a human subject, including any of the human subjects recited hereinabove.

In various embodiments, the medicament comprises greater than 350 mg of Aramchol™ In various embodiments, the medicament comprises between 350 mg and 1200 mg of Aramchol™ In various embodiments, the medicament comprises 400 mg, 500 mg, 600 mg, 700 mg, 800 mg, 900 mg, 1000 mg, 1100 mg, or 1200 mg of Aramchol™. In various embodiments, the medicament comprises between 400 mg and 1100 mg, or between 500 mg and 1000 mg, or between 600 mg and 900 mg of Aramchol™. In various embodiments, the medicament comprises 400 mg or 600 mg of Aramchol™.

In various embodiments, the medicament is to be administered daily. In some embodiments, the medicament daily dose is between about 400 mg and 900 mg. In some embodiments, the medicament is administered in a dose regimen of at least twice a day. In various embodiments, the medicament is to be administered once (QD), twice (BID) or three times a day (TID), in a dose of 100, 200, 250, 300, 350, 400, 450, 500, 550, 600, 650, 700, 750, 800 or 900 mg each; each represent a separate embodiment according to this invention. In various embodiments, the medicament is to be administered once a day (QD). In other embodiments, the medicament is to be administered twice a day (BID). In various embodiments, the medicament is to be administered three times a day (TID).

This invention also provides 3β-arachidylamido-7α, 12α-dihydroxy-5β-cholan-24-oic acid (Aramchol™) for use in administration to a human subject at a daily dose of greater than 300 mg. In some embodiments, the medicament daily dose is between about 400 mg and 900 mg. In some embodiments, the medicament is administered in a dose regimen of at least twice a day. In various embodiments, the medicament is administered once (QD), twice (BID) or three times (TID) daily in doses of 100, 150, 300, 350, 400, 450, 500, 550, 600, 650, 700, 750, 800, 850, or 900 mg each; each represents a separate embodiment according to this invention. In various embodiments, the daily dose is 600 mg and the medicament is administered twice a day (BID) in dose amount of 300 mg each dose. In various embodiments, the daily dose is 900 mg and the medicament is administered three times a day (TID) in dose amount of 300 mg each dose. In various embodiments, the daily dose is 800 mg and the medicament is administered twice a day (BID) in dose amount of 400 mg each dose. In various embodiments, the human subject is any of the human subjects recited hereinabove.

In various embodiments, the daily dose of Aramchol™ is greater than 350 mg. In various embodiments, the daily dose of Aramchol™ is between 350 mg and 1200 mg. In various embodiments, the daily dose of Aramchol™ is 400 mg, 500 mg, 600 mg, 700 mg, 800 mg, 900 mg, 1000 mg, 1100 mg, or 1200 mg; each represents a separate embodiment according to this invention. In various embodiments, the daily dose of Aramchol™ is between 400 mg and 1100 mg, or between 500 mg and 1000 mg, or between 600 mg and 900 mg. In various embodiments, the daily dose of Aramchol™ is 400 mg or 600 mg per day. In various embodiments, the daily dose of Aramchol™ is 600 mg, administered in two doses of 300 mg each. In various embodiments, the daily dose of Aramchol™ is 600 mg, administered in three doses of 200 mg each. In various embodiments, the daily dose of Aramchol™ is 900 mg, administered in three doses of 300 mg each. In various embodiments, the daily dose of Aramchol™ is 800 mg, administered in two doses of 400 mg each. In various embodiments, the daily dose of Aramchol™ is 600 mg, administered in two doses of 300 mg each, one in the morning and one in the evening.

Any suitable route may be used to administer the medicament or Aramchol™ of the invention to a subject.

According to some embodiments, suitable administration routes may be systemic routes. According to some embodiments, administering is administering systemically. According to some embodiments, the composition is formulated for systemic administration.

According to another embodiment, administration systemically is through an enteral route. According to another embodiment, administration through an enteral route is oral administration. According to some embodiments, the composition is formulated for oral administration.

Thus, the invention provides a method for treating the subjects recited in this application by administering Aramchol™ to the subject, wherein at least 350 mg of Aramchol™ is administered to the subject per day. In various embodiments, between 350 mg and 1200 mg of Aramchol™ is administered to the subject per day. In various embodiments, 400 mg, 500 mg, 600 mg, 700 mg, 800 mg, 900 mg, 1000 mg, 1100 mg, or 1200 mg of Aramchol™ is administered to the subject per day. In various embodiments, between 400 mg and 1100 mg, or between 500 mg and 1000 mg, or between 600 mg and 900 mg of Aramchol™ is administered to the subject per day. In various embodiments, 400 mg or 600 mg of Aramchol™ is administered to the subject per day. In various embodiments, the method comprises administering Aramchol™ in an amount of about 150, 200, 250, 300, 350, 400, 450, 500, 550, 600 mg once, twice or three times per day; each represents a separated embodiment according to this invention. In some embodiments, the Aramchol™ daily dose is between about 400 mg and 900 mg. In some embodiments, the Aramchol™ is administered in a dose regimen of at least twice a day. In various embodiments, the method comprises administering Aramchol™ in an amount of about 150 to about 600 mg twice a day. In various embodiments, the method comprises administering Aramchol™ in an amount of about 200 to about 450 mg twice a day. In various embodiments, the method comprises administering Aramchol™ in an amount of 300 mg twice a day. In various embodiments, 600 mg per day is administered to the subject in two doses of 300 mg each. In various embodiments, 600 mg per day is administered to the subject in three doses of 200 mg each. In various embodiments, 600 mg per day is administered to the subject in two doses of 300 mg each, one dose every 12 hrs.

In various embodiments, the medicament or Aramchol™ is administered in the morning, in the afternoon, or in the evening. In various embodiments, the medicament or Aramchol™ is administered in the morning and in the evening. In various embodiments, the medicament or Aramchol™ is administered every 12 hours. In various embodiments, the medicament or Aramchol™ is administered every 8 hours.

In various embodiments, the medicament or Aramchol™ is administered at the same time as, or within 30 minutes of a meal In various embodiments, the meal is breakfast, lunch, or dinner. In various embodiments, the meal is breakfast and dinner. In various embodiments, the meal is breakfast lunch and dinner.

In various embodiments, the meal is a high fat meal. A high fat meal is a meal wherein approximately 500 to 600 calories are fat calories.

In various embodiments, the meal is a high calorie meal. A high calorie meal is a meal of approximately 800 to 1000 calories.

In various embodiments, the medicament or Aramchol™ is administered with water. In various embodiments, the medicament or Aramchol™ is administered with at least 100 or at least 200 mL of water.

In various embodiments, the Aramchol™ is administered over the course of at least 52 weeks, at least 72 weeks, at least 96 weeks, at least 2 years, at least 3 years, or at least 4 years.

The invention further relates to use of a therapeutically effective amount of 3β-arachidylamido-7α, 12oc-dihydroxy-5β-cholan-24-oic acid (Aramchol™), or a pharmaceutically acceptable salt thereof, for inhibiting the development of hepatic fibrosis in a human subject afflicted with Non-Alcoholic Fatty Liver Disease and having a fibrosis score of zero comprising administering to the subject greater than 300 mg per day of 3β-arachidylamido-7α, 12α-dihydroxy-5β-cholan-24-oic acid (Aramchol™), or a pharmaceutically acceptable salt thereof, thereby inhibiting the development of hepatic fibrosis in said subject. In some embodiments, the Aramchol™ daily dose is between about 400 mg and 900 mg. In some embodiments, the Aramchol™ is administered in a dose regimen of at least twice a day. In various embodiments, the Aramchol™ is administered once (QD), twice (BID) or three times (TID) daily in doses of 100, 150, 300, 350, 400, 450, 500, 550, 600, 650, 700, 750, 800, 850, or 900 mg each; each represents a separate embodiment according to this invention. In various embodiments, the daily dose is 600 mg and the Aramchol™ is administered twice a day (BID) in dose amount of 300 mg each dose. In various embodiments, the daily dose is 900 mg and the Aramchol™ is administered three times a day (TID) in dose amount of 300 mg each dose. In various embodiments, the daily dose is 800 mg and the Aramchol™ is administered twice a day (BID) in dose amount of 400 mg each dose.

The invention further provides 3β-arachidylamido-7α, 12oc-dihydroxy-5β-cholan-24-oic acid (Aramchol™), or a pharmaceutically acceptable salt thereof, for inhibiting the development of hepatic fibrosis in a human subject afflicted with Non-Alcoholic Fatty Liver Disease and having a fibrosis score of zero comprising administering to the subject greater than 300 mg per day of 3β-arachidylamido-7α, 12α-dihydroxy-5β-cholan-24-oic acid (Aramchol™), or a pharmaceutically acceptable salt thereof, thereby for inhibiting the development of hepatic fibrosis in a human subject afflicted with Non-Alcoholic Fatty Liver Disease and having a fibrosis score of zero comprising administering to the subject greater than 300 mg per day of 3β-arachidylamido-7α, 12α-dihydroxy-5β-cholan-24-oic acid (Aramchol™), or a pharmaceutically acceptable salt thereof, thereby inhibiting the development of hepatic fibrosis in said subject. In some embodiments, the Aramchol™ daily dose is between about 400 mg and 900 mg. In some embodiments, the Aramchol™ is administered in a dose regimen of at least twice a day. In various embodiments, the Aramchol™ is administered once (QD), twice (BID) or three times (TID) daily in doses of 100, 150, 300, 350, 400, 450, 500, 550, 600, 650, 700, 750, 800, 850, or 900 mg each; each represents a separate embodiment according to this invention. In various embodiments, the daily dose is 600 mg and the Aramchol™ is administered twice a day (BID) in dose amount of 300 mg each dose. In various embodiments, the daily dose is 900 mg and the Aramchol™ is administered three times a day (TID) in dose amount of 300 mg each dose. In various embodiments, the daily dose is 800 mg and the Aramchol™ is administered twice a day (BID) in dose amount of 400 mg each dose.

The invention further provides a medicament comprising 3β-arachidylamido-7 or, 12α-dihydroxy-5β-cholan-24-oic acid (Aramchol™), or a pharmaceutically acceptable salt thereof, for inhibiting the development of hepatic fibrosis in a human subject afflicted with Non-Alcoholic Fatty Liver Disease and having a fibrosis score of zero comprising administering to the subject greater than 300 mg per day of 3β-arachidylamido-7ot, 12α-dihydroxy-5β-cholan-24-oic acid (Aramchol™), or a pharmaceutically acceptable salt thereof, thereby for inhibiting the development of hepatic fibrosis in a human subject afflicted with Non-Alcoholic Fatty Liver Disease and having a fibrosis score of zero comprising administering to the subject greater than 300 mg per day of 3β-arachidylamido-7α, 12α-dihydroxy-5β-cholan-24-oic acid (Aramchol™) or a pharmaceutically acceptable Salt thereof, thereby inhibiting the development of hepatic fibrosis in said subject. In some embodiments, the Aramchol™ daily dose is between about 400 mg and 900 mg. In some embodiments, the Aramchol™ is administered in a dose regimen of at least twice a day. In various embodiments, the Aramchol™ is administered once (QD), twice (BID) or three times (TID) daily in doses of 100, 150, 300, 350, 400, 450, 500, 550, 600, 650, 700, 750, 800, 850, or 900 mg each; each represents a separate embodiment according to this invention. In various embodiments, the daily dose is 600 mg and the Aramchol™ is administered twice a day (BID) in dose amount of 300 mg each dose. In various embodiments, the daily dose is 900 mg and the Aramchol™ is administered three times a day (TID) in dose amount of 300 mg each dose. In various embodiments, the daily dose is 800 mg and the Aramchol™ is administered twice a day (BID) in dose amount of 400 mg each dose.

The invention provides a pharmaceutical package comprising a) 3β-arachidylamido-7α, 12c-dihydroxy-5β-cholan-24-oic acid (Aramchol™), or a pharmaceutically acceptable salt thereof, and b) instructions for use in inhibiting the development of hepatic fibrosis in a human subject afflicted with Non-Alcoholic Fatty Liver Disease and having a fibrosis score of zero comprising administering to the subject greater than 300 mg per day of 3β-arachidylamido-7α, 12α-dihydroxy-5β-cholan-24-oic acid (Aramchol™), or a pharmaceutically acceptable salt thereof, thereby inhibiting the development of hepatic fibrosis in said subject. In some embodiments, the Aramchol™ daily dose is between about 400 mg and 900 mg. In some embodiments, the Aramchol™ is administered in a dose regimen of at least twice a day. In various embodiments, the Aramchol™ is administered once (QD), twice (BID) or three times (TID) daily in doses of 100, 150, 300, 350, 400, 450, 500, 550, 600, 650, 700, 750, 800, 850, or 900 mg each; each represents a separate embodiment according to this invention. In various embodiments, the daily dose is 600 mg and the Aramchol™ is administered twice a day (BID) in dose amount of 300 mg each dose. In various embodiments, the daily dose is 900 mg and the Aramchol™ is administered three times a day (TID) in dose amount of 300 mg each dose. In various embodiments, the daily dose is 800 mg and the Aramchol™ is administered twice a day (BID) in dose amount of 400 mg each dose.

According to some embodiments, oral administration is in the form of hard or soft gelatin capsules, pills, capsules, tablets, including coated tablets, dragees, elixirs, suspensions, liquids, gels, slurries or syrups and controlled release forms thereof. Thus, the invention provides a method of administering Aramchol™ in the form of a tablet, a capsule, or in a liquid.

Suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP).

If desired, disintegrating agents, such as cross-linked polyvinyl pyrrolidone, agar, or alginic acid or a salt thereof, such as sodium alginate, may be added. Capsules and cartridges of, for example, gelatin for use in a dispenser may be formulated containing a powder mix of the compound and a suitable powder base, such as lactose or starch.

Solid dosage forms for oral administration include without limitation capsules, tablets, pills, powders, and granules. In such solid dosage forms, the active compound is admixed with at least one inert pharmaceutically acceptable carrier such as sucrose, lactose, or starch. Such dosage forms can also comprise, as it normal practice, additional substances other than inert diluents, e.g., lubricating, agents. In the case of capsules, tablets and pills, the dosage forms may also comprise buffering agents. Tablets and pills can additionally be prepared with enteric coatings. The term "enteric coating", as used herein, refers to a coating which controls the location of composition absorption within the digestive system. Non-limiting examples for materials used for enteric coating are fatty acids, waxes, plant fibers or plastics.

Liquid dosage forms for oral administration may further contain adjuvants, such as wetting agents, emulsifying and suspending agents, and sweetening, flavoring and perfuming agents.

According to some embodiments, concomitant treatment with fatty acids such as ethyl eicosapentanoate, eicosapentaenoic acid, and their amides, salts and phospholipids is explicitly excluded. In other embodiment, concomitant treatment with bile acids such as ursodeoxycholic acid and lithocholic acid is excluded. In other embodiments concomitant treatment with vitamin D receptor agonists, acetyl-CoA carboxylase inhibitors, dual PPAR delta/gamma agonists, and inhibitors of myofibroblast trans-differentiation and activation is excluded. According to advantageous embodiments, Aramchol™ or the pharmaceutically acceptable salt thereof is used as a sole active ingredient.

According to some embodiments, the composition is administered in several dosages over prolonged periods until a sufficient response has been achieved.

As disclosed herein, Aramchol™ was found to be an unexpectedly potent therapeutic agent, capable of reversing established fibrosis and for inhibiting the development of fibrosis, and reducing cirrhosis and collagen synthesis in stellate calls even when used as a single therapeutic agent, in the absence of adjunct therapy. Thus, according to an advantageous embodiment of the methods of the invention, Aramchol™ or the pharmaceutically acceptable salt thereof is administered as a sole active ingredient. In another embodiment, the subject is human.

In another embodiment of the methods of the invention, Aramchol™ is administered orally. In another embodiment of the methods of the invention, Aramchol™ is in the form of Aramchol™ free acid. In another embodiment of the methods of the invention, Aramchol™ is in the form of an amine-based salt. In certain particular embodiments, the salt is a meglumine, lysine or tromethamine Aramchol™ salt; each possibility represents a separate embodiment of the invention.

Patient Outcomes

According to various embodiments, this invention provides a method of for treating hepatic fibrosis in a human subject afflicted with hepatic fibrosis comprising administering to the subject greater than 300 mg per day of 3β-arachidylamido-7α, 12α-dihydroxy-5β-cholan-24-oic acid (Aramchol™), or a pharmaceutically acceptable salt thereof, thereby treating hepatic fibrosis in said subject. In some embodiments, the Aramchol™ daily dose is between about 400 mg and 900 mg. In some embodiments, the Aramchol™ is administered in a dose regimen of t least twice a day. In various embodiments, the Aramchol™ is administered once (QD), twice (BID) or three times (TID) daily in doses of 100, 150, 300, 350, 400, 450, 500, 550, 600, 650, 700, 750, 800, 850, or 900 mg each; each represents a separate embodiment according to this invention. In various embodiments, the daily dose is 600 mg and the Aramchol™ is administered twice a day (BID) in dose amount of 300 mg each dose. In various embodiments, the daily dose is 900 mg and the Aramchol™ is administered three times a day (TID)

in dose amount of 300 mg each dose. In various embodiments, the daily dose is 800 mg and the Aramchol™ is administered twice a day (BID) in dose amount of 400 mg each dose.

In various embodiments, the methods according to this invention further comprise reduction in liver fat in said subject.

In various embodiments, the methods according to this invention further comprise improvement in subject's Steatosis.

In various embodiments, the methods according to this invention further comprise reduction in subject's ballooning.

In various embodiments, the methods according to this invention further comprise NAFLD resolution in said subject. In other embodiments, the methods according to this invention further comprise NASH resolution in said subject.

In various embodiments, the methods according to this invention further comprise NAFLD resolution without worsening of fibrosis. In various embodiments, the methods according to this invention further comprise reduction of fibrosis without NAFLD worsening. In various embodiments, the methods according to this invention further comprise NASH resolution without worsening of fibrosis. In various embodiments, the methods according to this invention further comprise reduction of fibrosis without NASH worsening.

In various embodiments, the methods according to this invention further comprise reduction of ALT levels in said subject.

In various embodiments, the methods according to this invention further comprise reduction of AST levels in said subject.

In various embodiments, the methods according to this invention further comprise reduction of HbA1c levels in said subject.

In various embodiments, the methods according to this invention further comprise lack of subject's progression to Cirrhosis.

In various embodiments, the methods according to this invention further comprise inhibiting progression of Non-Alcoholic Fatty Liver Disease (NAFLD) and/or Non-Alcoholic Steatohepatitis (NASH).

In various embodiments, the methods according to this invention further comprise any combination of hereinbove mentioned indications and/or symptoms.

In various embodiments, treating the subject comprises lack of worsening of the subject's NAFLD Activity (NAS) score.

In an embodiment treating the subject comprises lack of worsening of the subject's Steatosis, Activity and Fibrosis (SAF) Activity score.

In various embodiments, treating the subject comprises lack of worsening of the subject's fibrosis score.

In various embodiments, the lack of worsening is lack of worsening at 52, 65, 72 or 96 weeks from the commencement of administration of Aramchol™.

In various embodiments, the lack of worsening is lack of worsening at 2, 3, or 4 years from the commencement of administration of Aramchol™.

In various embodiments, treating the subject treating comprises an improvement of the subject's NAFLD Activity (NAS) score.

In various embodiments, the subject's NAS score is at least 4 at the commencement of administration of Aramchol™ and the improvement of the subject's NAS score is an improvement of at least 2 points.

In various embodiments, treating the subject comprises an improvement of the subject's Steatosis, Activity and Fibrosis (SAF) Activity Score.

In various embodiments, the subject's SAF Activity score is at least 4 at the commencement of administration of Aramchol™ and improvement of the subject's SAF Activity score is an improvement of at least 2 points.

In various embodiments, treating the subject comprises an improvement of the subject's fibrosis score.

In various embodiments, the improvement of the subject's fibrosis score is an improvement of 1 grade, or greater than 1 grade. In various embodiments, improvement is improvement at 52, 65, 72, or 96 weeks from the commencement of administration of Aramchol™.

In various embodiments, improvement is improvement at 2, 3, or 4 years from the commencement of administration of Aramchol™.

In various embodiments, treating the fibrosis comprises inhibiting progression of Non-Alcoholic Fatty Liver Disease (NAFLD). In various embodiments, inhibiting the fibrosis comprises inhibiting progression of Non-Alcoholic Fatty Liver Disease (NAFLD).

In various embodiments, inhibiting progression of NAFLD comprises prevention of progression, or reduced progression relative to a patient not treated with Aramchol™.

In various embodiments, the human subject is afflicted with Non-Alcoholic Steatohepatitis (NASH) and treating comprises inhibiting progression of NASH.

In various embodiments, inhibiting progression of NASH comprises prevention of progression, or reduced progression relative to a patient not treated with Aramchol™.

In various embodiments, treating comprises preventing progression from Non-Alcoholic Fatty Liver Disease (NAFLD) to NASH.

In various embodiments, improvement progression is progression at 2, 4, 8, 24, 40, 52, 65, 72, or 96 weeks from the commencement of administration of Aramchol™.

In various embodiments, improvement progression is progression at 2, 3, or 4 years from the commencement of administration of Aramchol™.

In various embodiments, the human subject is afflicted with Non-Alcoholic Steatohepatitis (NASH) and the treating comprises NASH resolution in the subject.

In various embodiments, NASH resolution comprises the human subject having a ballooning score of 0 and an inflammation score of 0 or 1.

In various embodiments, treating comprises NASH resolution in the subject at 52, 72, or 96 weeks from the commencement of administration of Aramchol™.

In various embodiments, treating comprises NASH resolution in the subject at 2, 3, or 4 years from the commencement of administration of Aramchol™.

In various embodiments, treating comprises a reduction in the level of liver triglycerides in the subject relative to the level at the commencement of administration of Aramchol™.

In various embodiments, treating comprises a reduction in the ratio of liver triglycerides to water in the subject relative to the ratio at the commencement of administration of Aramchol™.

In various embodiments, there is a greater than 10% reduction in ratio of liver triglycerides to water.

In various embodiments, there is a 10% to 40% reduction in ratio of liver triglycerides to water.

In various embodiments, there is a 15% to 35% reduction in ratio of liver triglycerides to water.

In various embodiments, there is a 20% to 30% reduction in ratio of liver triglycerides to water.

In various embodiments, the methods according to this invention comprise:

a. a reduction in the level of Hemoglobin A1C or HOMA-IR;
b. a reduction in the level of Fibrinogen, CK-18, C-reactive protein (CRP), TNFα, IL 6 and fibrosis Tests (NFS;
c. a reduction in the ratio of leptin to adinopectin; or
d. an increase in the level of adinopectin;

in the subject relative to the level or ratio at the commencement of administration of Aramchol™.

In various embodiments, the methods according to this invention further comprise:

a. a reduction in the human subject's body weight relative to the human subject's body weight at the commencement of administration of Aramchol™;
b. a reduction in the human subject's waist circumference relative to the human subject's waist circumference at the commencement of administration of Aramchol™; or
c. a reduction in the human subject's Fatty Liver Index relative to the human subject's Fatty Liver Index at the commencement of administration of Aramchol™.

In various embodiments, the reduction or increase is a reduction or increase at 2, 4, 8, 24, 40, 52, 65, 72, or 96 weeks from the commencement of administration of Aramchol™.

In various embodiments, the reduction or increase is a reduction or increase at 2, 3, or 4 years from the commencement of administration of Aramchol™.

In another embodiment, administration of Aramchol™ or a pharmaceutically acceptable salt thereof according to the methods of the invention inhibits collagen synthesis (e.g. COL1A1 expression) in hepatic stellate calls. In another embodiment, administration of Aramchol™ or a pharmaceutically acceptable salt thereof according to the methods of the invention enhances PPAR-γ expression in hepatic stellate calls.

The present invention also provides a medicament or Aramchol™ of the invention wherein the medicament or Aramchol™ is effective to prevent worsening of NASH in the subject.

In various embodiments, the medicament or Aramchol™ is effective to prevent worsening of fibrosis in the subject.

The present invention also provides a medicament or Aramchol™ of the invention wherein the human subject being administered the medicament or Aramchol™ is afflicted with fibrosis and wherein the medicament or Aramchol™ is effective to improve the human subject's fibrosis score.

In various embodiments, the medicament or Aramchol™ is effective to improve the human subject's NAFLD Activity (NAS) score.

In various embodiments, the medicament or Aramchol™ is effective to improve the human subject's NAFLD Activity (NAS) score by at least 2 points.

In various embodiments, the medicament or Aramchol™ is effective to improve the human subject's Steatosis, Activity and Fibrosis (SAF) Activity score.

In various embodiments, the medicament or Aramchol™ is effective to improve the human subject's Steatosis, Activity and Fibrosis (SAF) Activity score by at least 2 points.

In various embodiments, the medicament or Aramchol™ is effective to resolve NASH in the human subject.

In various embodiments, resolving NASH comprises reducing ballooning to a score of 0 and reducing inflammation to a score of 0 or 1.

In various embodiments, the medicament or Aramchol™ is effective at 2, 4, 8, 24, 40, 52, 65, 72, or 96 weeks, or 2, 3, or 4 years from the commencement of administration.

In various embodiments, the medicament or Aramchol™ is effective to reduce the level of liver triglycerides in the subject relative to the level at the commencement of administration.

In various embodiments, the medicament or Aramchol™ is effective to reduce the ratio of liver triglycerides to water in the subject relative to the ratio at the commencement of administration.

In various embodiments, the medicament or Aramchol™ is effective to reduce the ratio of liver triglycerides to water in the subject by at least 10% relative to the ratio at the commencement of administration.

In various embodiments, the medicament or Aramchol™ is effective to reduce the ratio of liver triglycerides to water in the subject by between 10% and 40% relative to the ratio at the commencement of administration.

In various embodiments, the medicament or Aramchol™ is effective to reduce the ratio of liver triglycerides to water in the subject by between 15% and 35% relative to the ratio at the commencement of administration.

In various embodiments, the medicament or Aramchol™ is effective to reduce the ratio of liver triglycerides to water in the subject by between 20% and 30% relative to the ratio at the commencement of administration.

In various embodiments, the medicament or Aramchol™ is effective to:

a. reduce the level of Hemoglobin A1C or HOMA-IR;
b. reduce the level of Fibrinogen, CK-18, C-reactive protein (CRP), TNFα, IL 6 and fibrosis Tests (NFS);
c. reduce the ratio of leptin to adinopectin; or
d. increase the level of adinopectin;

in the subject relative to the level or ratio at the commencement of administration.

In various embodiments, the medicament or Aramchol™ is effective to:

a. reduce the human subject's body weight relative to the human subject's body weight at the commencement of administration;
b. reduce the human subject's waist circumference relative to the human subject's waist circumference at the commencement of administration; or
c. reduce the human subject's Fatty Liver Index relative to the human subject's Fatty Liver Index at the commencement of administration.

In various embodiments, the medicament or Aramchol™ is effective at 2, 4, 8, 24, 40, 52, 65, 72, or 96 weeks, or 2, 3, or 4 years from the commencement of administration.

The invention relates to use of a therapeutically effective amount of 3β-arachidylamido-7α, 12α-dihydroxy-5β-cholan-24-oic acid (Aramchol™), or a pharmaceutically acceptable salt thereof, for the treatment and inhibition of fibrotic disorders, hepato-fibrotic conditions associated with Non-Alcoholic Fatty Liver Disease (NAFLD) and Non-Alcoholic Steatohepatitis (NASH).

The invention provides 3β-arachidylamido-7α, 12α-dihydroxy-5β-cholan-24-oic acid (Aramchol™), or a pharmaceutically acceptable salt thereof, for the treatment and inhibition of fibrotic disorders, hepato-fibrotic conditions associated with Non-Alcoholic Fatty Liver Disease (NAFLD) and Non-Alcoholic Steatohepatitis (NASH).

The invention provides a medicament comprising 3β-arachidylamido-7α, 12α-dihydroxy-5β-cholan-24-oic acid (Aramchol™), or a pharmaceutically acceptable salt thereof, for the treatment and inhibition of fibrotic disorders, hepato-fibrotic conditions associated with Non-Alcoholic Fatty Liver Disease (NAFLD) and Non-Alcoholic Steatohepatitis (NASH).

The invention provides a pharmaceutical package comprising a) 3β-arachidylamido-7α, 12α-dihydroxy-5β-cholan-24-oic acid (Aramchol™), or a pharmaceutically acceptable salt thereof, and b) instructions for use of the Aramchol™ in the treatment and inhibition of fibrotic disorders, hepato-fibrotic conditions associated with Non-Alcoholic Fatty Liver Disease (NAFLD) and Non-Alcoholic Steatohepatitis (NASH).

Combination Therapy

The C—C motif chemokine receptor CCR5 is involved in the process by which HIV, the virus that causes AIDS, enters cells. CCR5 receptor antagonists are a class of small molecules that antagonize the CCR5 receptor. Hence, antagonists of this receptor are entry inhibitors and have potential therapeutic applications in the treatment of HIV infections. The C—C chemokine receptor type 2 (CCR2) is a protein that in humans is encoded by the CCR2 gene. This gene encodes two isoforms of a receptor for monocyte chemoattractant protein-1 (CCL2), a chemokine which specifically mediates chemotaxis of cells such as monocytes and macrophages. Cenicriviroc ((S,E)-8-(4-(2-Butoxyethoxy)phenyl)-1-isobutyl-N-(4-(((1-propyl-1H-imidazol-5-yl)methyl) sulfinyl)phenyl)-1,2,3,4-tetrahydrobenzo[b]azocine-5-carboxamide, CAS No. 497223-25-3) is an inhibitor of both CCR2 and CCR5 receptors.

In various embodiments, of the invention, the methods further comprise administering a therapeutically effective amount of a pharmaceutical composition comprising a C—C chemokine receptor type 2 (CCR2) antagonist, a C—C chemokine receptor type 5 (CCR5) antagonist, a dual CCR2/CCR5 antagonist, or a combination or pharmaceutically acceptable salt thereof.

In various embodiments, the CCR2 antagonist is selected from the group consisting of: a double-stranded RNA, a compound antagonizing the binding of CCR2 to its ligand, a neutralizing antibody to CCR2, a ligand corresponding to a neutralizing antibody to CCR2, an isolated peptide derived from the sequences of CCR2 or analogs thereof capable of inhibiting CCR2, an antisense nucleic acid, an antagonist microRNA, and an enzymatic RNA molecule.

In various embodiments, the methods further comprise administering to the subject a CCR5 antagonist and a CCR2 antagonist, or a dual CCR2/CCR5 antagonist.

In various embodiments, the CCR2/CCR5 dual antagonist is (S,E)-8-(4-(2-Butoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide (Cenicriviroc) or Cenicriviroc mesylate.

In various embodiments, the methods comprise administering a daily dose of 50 to 500 mg of Cenicriviroc. In certain embodiments, the method described above comprises administering a daily dose of 10 to 200 mg of Cenicriviroc. In certain embodiments, the method comprises administering a dailydose of 50 to 500 mg, 50 to 400 mg, 50 to 300 mg, 50 to 200 mg, or 100 to 200 mg of Cenicriviroc. In certain embodiments, the method described above comprises administering a daily dose of 100-200 mg of Cenicriviroc. In various embodiments, the method comprises administering a daily dose of 100 or 200 mg of Cenicriviroc.

In some embodiments, the methods further comprise administering a therapeutically effect amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids.

In some embodiments, the EPA-E or EPA may be at least 40% by weight in total of the fatty acids and their derivatives.

In some embodiments, the pharmaceutical composition comprises Epadel® (Machida Pharmaceutical Co., Ltd., Tokyo Japan), Lovaza™ (GlaxoSmithKline, FL USA), Omacor™ (Pronova Biopharma ASA, Oslo Norway), Lotriga™ (Takeda Pharmaceutical Co., Ltd., Osaka Japan), Vascepa™ (Amarin Pharma Inc., NJ USA), Epanova™ (Astra Zeneca Pharmaceuticals LP, Wilmington, Germany) or Omtryg™ (Trygg Pharma Inc., VA USA).

Lovaza™, omega-3-acid ethyl esters, predominantly a combination of ethyl esters of eicosapentaenoic acid (EPA—approximately 465 mg) and docosahexaenoic acid (DHA—approximately 375 mg), is indicated as an adjunct to diet to reduce triglyceride (TG) levels in adult patients with severe (≥500 mg/dL) hypertriglyceridemia (Lovaza, Food and Drug Administration Approved Labeling (Reference ID:3371921) [online], GlaxoSmithKline, 2013).

The recommended dose and schedule for Lovaza™ is 4 g per day. The daily dose may be taken as a single 27 4-gram dose (4 capsules) or as two 2-gram doses (2 capsules given twice daily).

In some embodiments, the administration of Lovaza™ comprises 4.0 g per day, 3.5 g per day, 3.0 g per day, 2.5 g per day, 2.0 g per day, 1.5 g per day, 1.0 g per day or less of Lovaza™.

Omacor™, omega-3-acid ethyl esters, predominantly a combination of ethyl esters of eicosapentaenoic acid (EPA—approximately 465 mg) and docosahexaenoic acid (DHA—approximately 375 mg), is a a lipid-regulating agent. (Reference ID: "FPL for approved NDA 21-654") [online], Abbott Laboratories).

The recommended dose and schedule for Omacor™ is 4 g per day. The daily dose may be taken as a single 4-g dose (4 capsules) or as two 2-g doses (2 capsules given twice daily).

In some embodiments, the administration of Omacor™ comprises 4.0 g per day, 3.5 g per day, 3.0 g per day, 2.5 g per day, 2.0 g per day, 1.5 g per day, 1.0 g per day or less of Omacor™.

Vascepa™, containing 1 gram of icosapent ethyl, an ethyl ester of the omega-3 fatty acid eicosapentaenoic acid (EPA), is a a lipid-regulating agent indicated as an adjunct to diet to reduce triglyceride (TG) levels in adult patients with severe (≥500 mg/dL) hypertriglyceridemia (Vascepa™, Food and Drug Administration Approved Labeling (Reference ID:3783357) [online], Amarin Pharmaceuticals, 2012).

The recommended dose and schedule for Vascepa™ is 4 grams per day taken as 2 capsules twice daily with food.

In some embodiments, the administration of Vascepa™ comprises 4.0 g per day, 3.5 g per day, 3.0 g per day, 2.5 g per day, 2.0 g per day, 1.5 g per day, 1.0 g per day or less of Vascepa™.

Epanova™, containing 1 gram of fish oil-derived free fatty acids, designated "omega-3-carboxylic acids," with at least 850 mg of polyunsaturated fatty acids, including multiple omega-3 fatty acids (eicosapentaenoic acid [EPA] and docosahexaenoic acid [DHA] being the most abundant), is a lipid-regulating agent indicated as an adjunct to diet to reduce triglyceride (TG) levels in adult patients with severe (≥500 mg/dL) hypertriglyceridemia (Epanova™, Food and Drug Administration Approved Labeling (Reference ID:3501113) [online], AstraZeneca Pharmaceuticals, 2014).

The recommended dose and schedule for Epanova™ is 4 grams per day taken as 2 grams (2 capsules) twice daily, or 4 grams (4 capsules) once daily.

In some embodiments, the administration of Epanova™ comprises 4.0 g per day, 3.5 g per day, 3.0 g per day, 2.5 g per day, 2.0 g per day, 1.5 g per day, 1.0 g per day or less of Epanova™.

Omtryg™, a combination of ethyl esters of omega-3 fatty acids predominantly a combination of ethyl esters of eicosapentaenoic acid (EPA—approximately 465 mg) and docosahexaenoic acid (DHA—approximately 375 mg), is a lipid-regulating agent, indicated as an adjunct to diet to reduce triglyceride (TG) levels in adult patients with severe (≥500 mg/dL) hypertriglyceridemia (Omtryg™, Food and Drug Administration Approved Labeling (Reference ID:3494935) [online], Trygg Pharma Inc., 2014).

The recommended dose and schedule for Omtryg™ is 4 grams per day taken as 2 grams (2 capsules) twice daily, or 4 grams (4 capsules) once daily.

In some embodiments, the administration of Omtryg™ comprises 4.0 g per day, 3.5 g per day, 3.0 g per day, 2.5 g per day, 2.0 g per day, 1.5 g per day, 1.0 g per day or less of Omtryg™.

The compositions recited hereinabove are described in U.S. Patent Application Publication No. 2016/0213639, the entire contents of which is incorporated by reference.

In some embodiments, the method further comprises administering a therapeutically effect amount of an inhibitor of Acetyl-CoA carboxylase (ACC) alone, or in combination with one or more additional therapeutic agents.

As used herein generally, "ACC inhibitor" means any therapeutic agent that reduces the activity of an acetyl CoA carboxylase enzyme.

Suitable ACC inhibitors include those described in WO2013/071169A1, WO2014/182943A1, WO2014/182945A1, WO2014/182950A1, and WO2014/182951A1, the entirety of each of which is hereby incorporated by reference.

In some embodiments, the ACC inhibitor is soraphen A.

In some embodiments, additional therapeutic agents are independently selected from the group consisting of angiotensin II receptor antagonists, angiotensin converting enzyme (ACE) inhibitors, caspase inhibitors, cathepsin B inhibitors, CCR2 chemokine antagonists, CCR5 chemokine antagonists, chloride channel stimulators, cholesterol solubilizers, diacylglycerol O-acyltransferase 1 (DGATl) inhibitors, dipeptidyl peptidase IV (DPPIV) inhibitors, farnesoid X receptor (FXR) agonists, FXR/TGR5 dual agonists, galectin-3 inhibitors, glucagon-like peptide (GLPI) agonists, glutathione precursors, hepatitis C virus NS3 protease inhibitors, HMG CoA reductase inhibitors, II~-hydroxysteroid dehydrogenase (II~-HSD I) inhibitors, IL-I~ antagonists, IL-6 antagonists, IL-I 0 agonists, IL-I 7 antagonists, ileal sodium bile acid cotransporter inhibitors, leptin analogs, 5-lipoxygenase inhibitors, LPL gene stimulators, lysyl oxidase homolog 2 (LOXL2) inhibitors, PDE3 inhibitors, PDE4 inhibitors, phospholipase C (PLC) inhibitors, PPARa agonists, PPARγ agonists, PPAR8 agonists, Rho associated protein kinase 2 (ROCK2) inhibitors, sodium glucose transporter-2 (SGLT2) inhibitors, stearoyl CoA desaturaseI inhibitors, thyroid hormone receptor-agonists, tumor necrosis factor a (TNFα) ligand inhibitors, transglutaminase inhibitors, transglutaminase inhibitor precursors, PTPib inhibitors, and ASKI inhibitors.

The compositions recited hereinabove are described in PCT International Application Publication No. WO 2016/112305, the entire contents of which is incorporated by reference.

In some embodiments, the method further comprises administering a therapeutically effect amount of Pioglitazone hydrochloride (Actos®) or an enantiopure deuterium-enriched pioglitazone.

As used herein, the deuterated pioglitazone contains deuterium enrichment at the chiral center of pioglitazone and optionally in other locations in the compound. Further, the deuterium-enriched pioglitazone is provided in enantiomerically pure form.

In some embodiments, the deuterium-enriched compound having an optical purity of at least 75% enantiomeric excess.

Pioglitazone hydrochloride, the active ingredient of Actos®, is a thiazolidinedione and an agonist for peroxisome proliferatoractivated receptor (PPAR) gamma indicated as an adjunct to diet and exercise to improve glycemic control in adults with type 2 diabetes mellitus in multiple clinical settings (Actos®, Food and Drug Administration Approved Labeling (Reference ID:2983732) [online], Takeda Pharmaceuticals, 2009-2011).

The recommended dose and schedule for Actos® is 15 mg or 30 mg once daily starting dose. If there is inadequate glycemic control, the dose can be increased in 15 mg increments up to a maximum of 45 mg once daily.

In some embodiments, the administration of Actos® comprises 15 mg, 16 mg, 17 mg, 18 mg, 19 mg, 20 mg, 25 mg, 30 mg, 35 mg, 40 mg, or 45 mg or less of Actos®.

The compositions recited hereinabove are described in PCT International Application Publication No. WO 2016/153948, the entire contents of which is incorporated by reference.

In some embodiments, the method further comprises administering a therapeutically effect amount of a peroxisome proliferator activated receptor (PPAR) delta and gamma dual agonist.

In some embodiments, the delta activity is greater than gamma activity, and gamma activity is greater than alpha activity.

In some embodiments, the method further comprises administering a therapeutically effect amount of an indane acetic acids and their derivatives, which are dual PPAR delta and gamma agonists.

Exemplary additional therapeutic agents may include, but are not limited to combination with: farnesoid X receptor agonists such as obeticholic acid and Px-104, GR-MD-02, cysteamine bitartrate, simtuzumab, emricasan, GFT-505, CER-002, KD3010, KD3020, MBX8025, LUM002, RP-103, galectin-3 blockers such as LIPC-1010 and GR-MD-02, cenicriviroc, vascular adhesion protein-1 inhibitors such as PXS4728A, metformin, PPAR gamma agonists such as rosiglitazone and pioglitazone, metformin, pentoxyfylline, vitamin E, selenium, omega-3 fatty acids and betaine.

The compositions recited hereinabove are described in PCT International Application Publication No. WO 2016/154258, the entire contents of which is incorporated by reference.

The embodiments referred to above refer to several drugs being substantially effective in the body at a same time. Several drugs can be administered substantially at the same time, or can be administered at different times but have effect on the body at the same time. For example, this includes administering Aramchol™ before or subsequently, while functioning of Aramchol™ in the body is substantially extant.

Thus in some embodiments, the method further comprises administering a therapeutically effect amount of a pharmaceutical composition comprising at least one compound selected from the group consisting of:

ethyl eicosapentanoate (EPA-E), eicosapentaenoic acid (EPA) and its pharmaceutically acceptable amides, salts, esters and phospholipids;

an inhibitor of Acetyl-CoA carboxylase (ACC) alone, or in combination with one or more additional therapeutic agents;

pioglitazone hydrochloride or an enantiopure deuterium-enriched pioglitazone; and a peroxisome proliferator activated receptor (PPAR) delta and gamma dual agonist.

In some embodiments, additional therapeutic agents are independently selected from the group consisting of angiotensin II receptor antagonists, angiotensin converting enzyme (ACE) inhibitors, caspase inhibitors, cathepsin B inhibitors, CCR2 chemokine antagonists, CCR5 chemokine antagonists, chloride channel stimulators, cholesterol solubilizers, diacylglycerol O-acyltransferase 1 (DGATl) inhibitors, dipeptidyl peptidase IV (DPPIV) inhibitors, farnesoid X receptor (FXR) agonists such as obeticholic acid and Px-104, FXR/TGR5 dual agonists, galectin-3 inhibitors such as LIPC-1010 and GR-MD-02, glucagon-like peptide (GLPI) agonists, glutathione precursors, hepatitis C virus NS3 protease inhibitors, HMG CoA reductase inhibitors, II~-hydroxysteroid dehydrogenase (II~-HSD I) inhibitors, IL-I-antagonists, IL-6 antagonists, IL-I 0 agonists, IL-I 7 antagonists, ileal sodium bile acid cotransporter inhibitors, leptin analogs, 5-lipoxygenase inhibitors, LPL gene stimulators, lysyl oxidase homolog 2 (LOXL2) inhibitors, PDE3 inhibitors, PDE4 inhibitors, phospholipase C (PLC) inhibitors, PPARa agonists, PPAR gamma agonists such as rosiglitazone and pioglitazone, metformin, pentoxyfylline, vitamin E, selenium, omega-3 fatty acids and betaine, PPAR8 agonists, Rho associated protein kinase 2 (ROCK2) inhibitors, sodium glucose transporter-2 (SGLT2) inhibitors, stearoyl CoA desaturasel inhibitors, thyroid hormone receptor-agonists, tumor necrosis factor a (TNFα) ligand inhibitors, transglutaminase inhibitors, transglutaminase inhibitor precursors, PTPib inhibitors, ASKI inhibitors, and vascular adhesion protein-1 inhibitors such as PXS4728A, metformin, GR-MD-02, cysteamine bitartrate, simtuzumab, emricasan, GFT-505, CER-002, KD3010, KD3020, MBX8025, LUM002, RP-103, and cenicriviroc.

The administration of two drugs to treat a given condition, such as non-alcoholic fatty liver disease (NAFLD), raises a number of potential problems. In vivo interactions between two drugs are complex. The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug. (Guidance for Industry, 1999) Thus, when two drugs are administered to treat the same condition, it is unpredictable whether each will complement, have no effect on, or interfere with the therapeutic activity of the other in a human subject.

Not only may the interaction between two drugs affect the intended therapeutic activity of each drug, but the interaction may increase the levels of toxic metabolites (Guidance for Industry, 1999). The interaction may also heighten or lessen the side effects of each drug. Hence, upon administration of two drugs to treat a disease, it is unpredictable what change will occur in the negative side effect profile of each drug.

Additionally, it is difficult to accurately predict when the effects of the interaction between the two drugs will become manifest. For example, metabolic interactions between drugs may become apparent upon the initial administration of the second drug, after the two have reached a steady-state concentration or upon discontinuation of one of the drugs. (Guidance for Industry, 1999)

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

Each embodiment disclosed herein is contemplated as being applicable to each of the other disclosed embodiments. Thus, all combinations of the various elements described herein are within the scope of the invention.

The following examples are presented in order to more fully illustrate some embodiments of the invention. They should, in no way be construed, however, as limiting the broad scope of the invention.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Example 1—Thioacetamide (TAA)-Induced Fibrosis—Model for Hepatic Cirrhosis

Liver fibrosis was induced in Wistar rats by intraperitoneal injections of TAA (20 mg/100 gr body weight) twice per week during 10 weeks. I.p. application of TAA results in hepatic centrolobular necrosis, elevated transaminase activity and robust liver fibrosis. Treatment groups further included co-administration of Aramchol™ (1 or 5 mg/kg orally) or obaticholic acid (OCA, 5 mg/kg). A control group of saline-treated rats (in the absence of TAA administration) was further included. Rats were then sacrificed, and livers were observed macroscopically for signs of cirrhosis and necrotic lesions, and microscopically, following Masson Goldner staining. The fibrosis score, calculated at a scale of 0-4, was determined for each sample, wherein 0 indicates no fibrosis and 4 indicates advanced fibrosis and cirrhosis.

As can be seen in FIGS. 1A-1D and 2A-2B, treatment with Aramchol™ (5 mg/kg) significantly prevented TAA induced fibrosis. The treatment reduced significantly the development of necrosis and cirrhosis (FIGS. 1A-1D), as well as the fibrotic score and collagen distribution in the tissue (FIGS. 2A-2B), in a dose-dependent manner. In contradistinction, OCA did not induce statistically significant reduction in these parameters.

Thus, Aramchol™ was surprisingly found to be a potent anti-fibrotic and anti-cirrhotic agent. Aramchol™ was also found to be unexpectedly superior to OCA and provide for improved, effective treatment for liver fibrosis.

Cirrhosis and portal hypertension from TAA intoxication may eventually lead to the development of acute liver failure and associated conditions such as hepatic encephalopathy, and the TAA model is also used in evaluating these phenomena. Accordingly, as disclosed herein, Aramchol™ may also be used in some embodiments for preventing acute or fatal liver failure and/or hepatic or portosystemic encephalopathy, for example toxin-induced liver failure and/or hepatic encephalopathy.

Example 2—Inhibition of Collagen Synthesis in Stellate Cells

LX2 cells (150.000 cells per well) were plated in DMEM media containing antibiotics, glutamine and bovine fetal serum. After 24 hours incubation, media was changed to 0% serum and incubated for an additional period of 16 hours. Then, Aramchol™ (10 mM) was added and 24 hours later RNA was extracted with Trizol.

Figure 3:
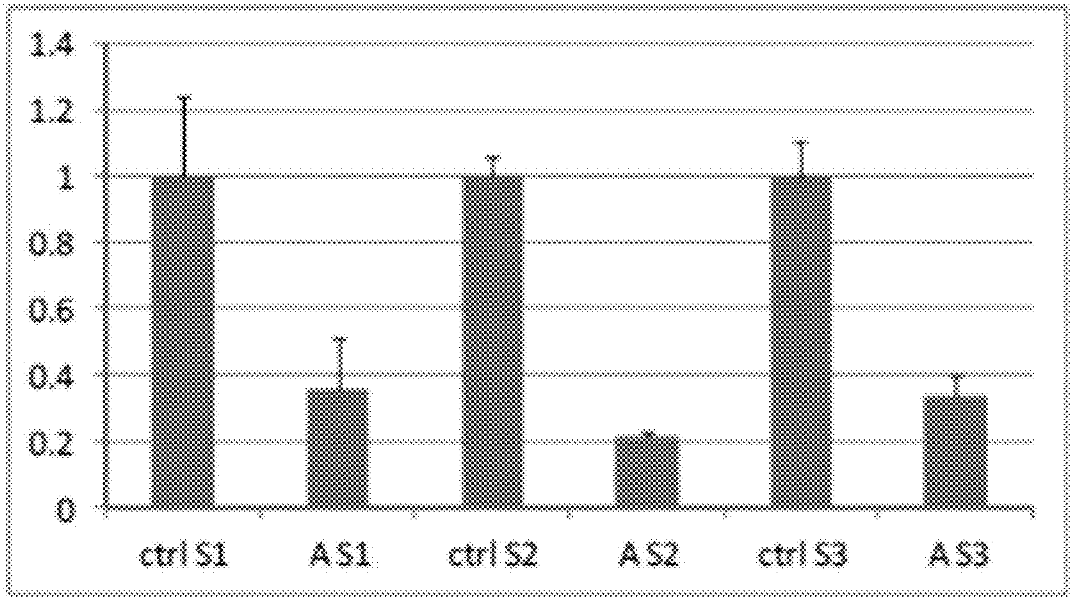
FIG. 3. depicts the effect of Aramchol™ on COL1A1 expression in LX-2 human hepatic stellate cells. "Ctrl S1, S2 and S3" represent control (saline-treated cells) in three separate experiments; "A S1, S2 and S3" represent the result of Aramchol™ treated cells in these experiments.
Figure 4:
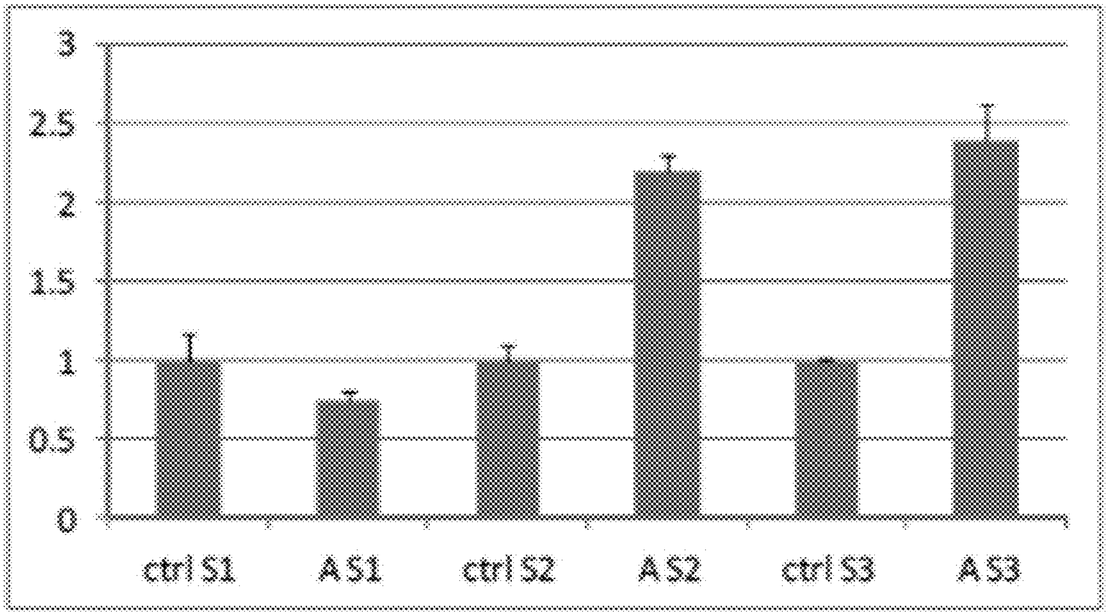
FIG. 4. depicts the effect of Aramchol™ on PPAR-γ expression in LX-2 human hepatic stellate cells. "Ctrl S1, S2 and S3" represent control (saline-treated cells) in three separate experiments; "A S1, S2 and S3" represent the result of Aramchol™ treated cells in these experiments.

Surprisingly, as can be seen in FIGS. 3 and 4, COL1A1 expression in LX-2 human hepatic stellate cells was reduced by Aramchol™ via PPARγ up-regulation.

Figure 5:
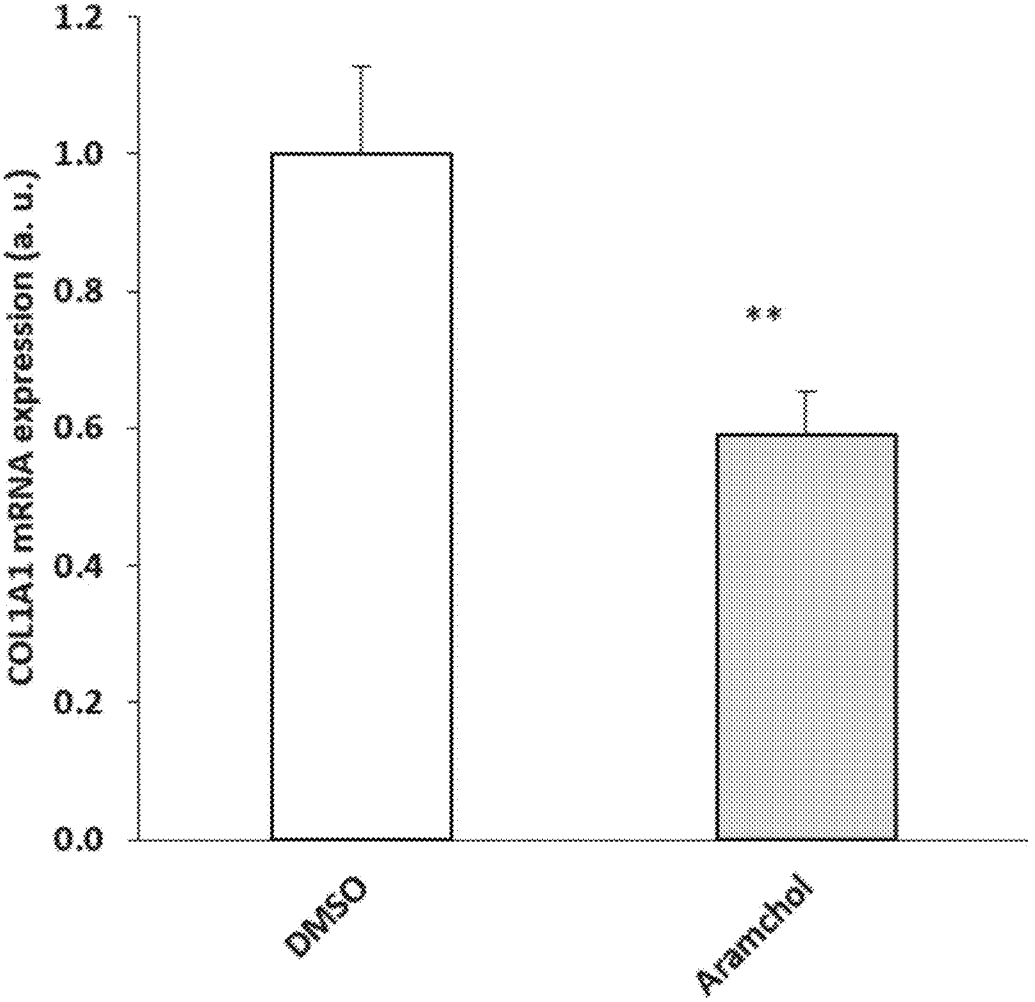
FIG. 5. depicts the effect of Aramchol™ on collagen production from LX-2 human hepatic stellate cells compared to a DMSO control.

Consistently, Aramchol™ significantly down regulates collagen production in LX-2 human hepatic stellate cells relative to a DMSO control (FIG. 5). Again, Aramchol™ was surprisingly found to be effective in reducing the production of collagen specifically in stellate cells.

Example 3—Aramchol™ Reduces Established Fibrosis in a MCD Diet Animal Model

The study described below investigates the mechanism of action of Aramchol™ and its potential effect on fibrosis using the 0.1% methionine- and choline-deficient (0.1MCD) diet mouse model of NASH.

C57Bl/6 were fed the Methionine and Choline Deficient (MCD) and control diet and were sacrificed after 4 weeks. The MCD diet induces aminotransferase elevation and changes in hepatic histological features, characterized by steatosis, local inflammation, hepatocyte necrosis and fibrosis. These changes occur rapidly and are morphologically similar to those observed in human NASH. In this study the MCD diet contained 0.1% methionine to minimize and stabilize weight loss. At the end of the second week, after verification of established NASH, 0.1MCD-fed mice were treated orally by gavage with Aramchol™ (5 mg/Kg/day) or vehicle (n=10, each condition). Control diet-fed mice were also treated with vehicle for same duration (n=10). At the end of the experiment, blood and liver samples were obtained. A diagram of the experimental design is shown below:

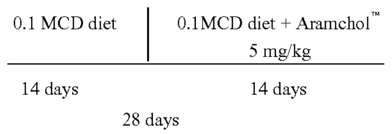

Figure 6A:
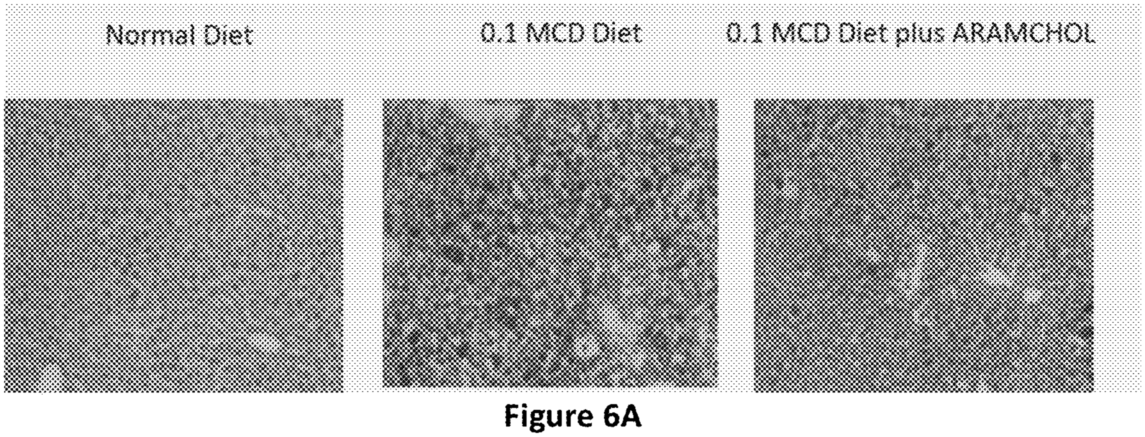
FIGS. 6A-6B depict the effect of Aramchol™ on liver steatosis in 0.1 MCD diet.
Figure 6B:
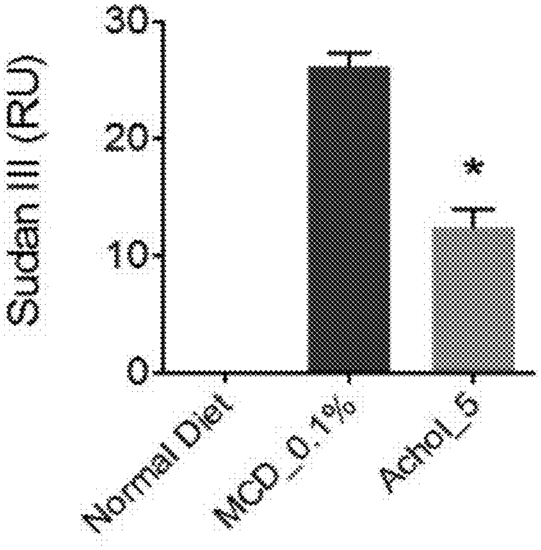
Figure 7A:
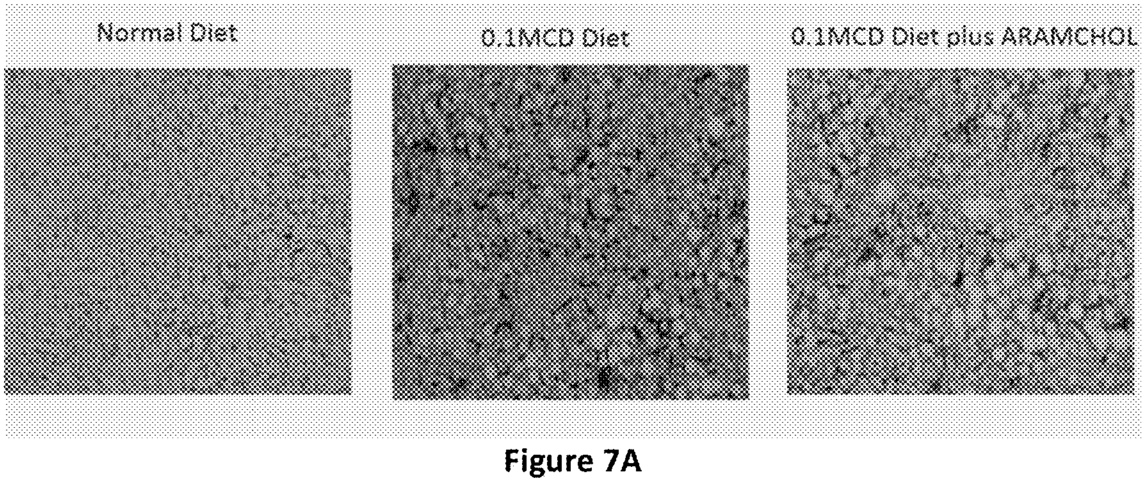
FIGS. 7A-7C depict the effect of Aramchol™ on macrophage activation and infiltration in 0.1 MCD diet.
Figure 7B:
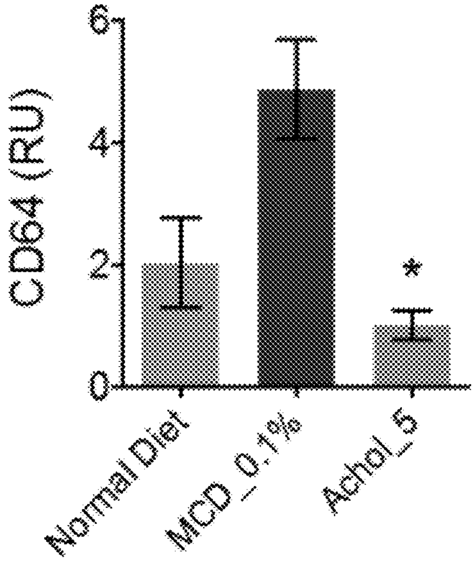
Figure 7C:
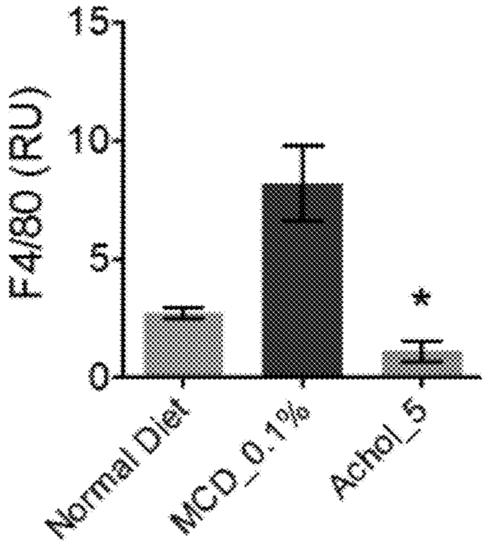
Figure 8A:
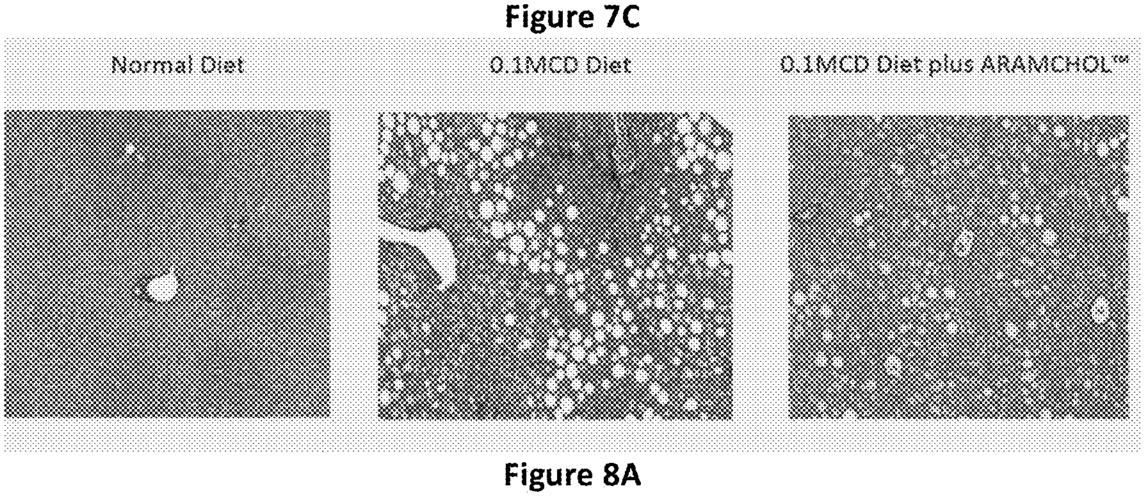
FIGS. 8A-8B. depict the effect of Aramchol™ on fibrosis in 0.1MCD Diet (histology—sirius red).
Figure 8B:
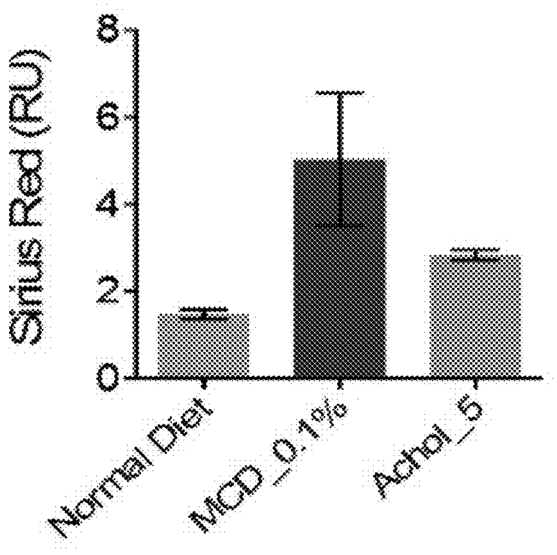
Figure 9:
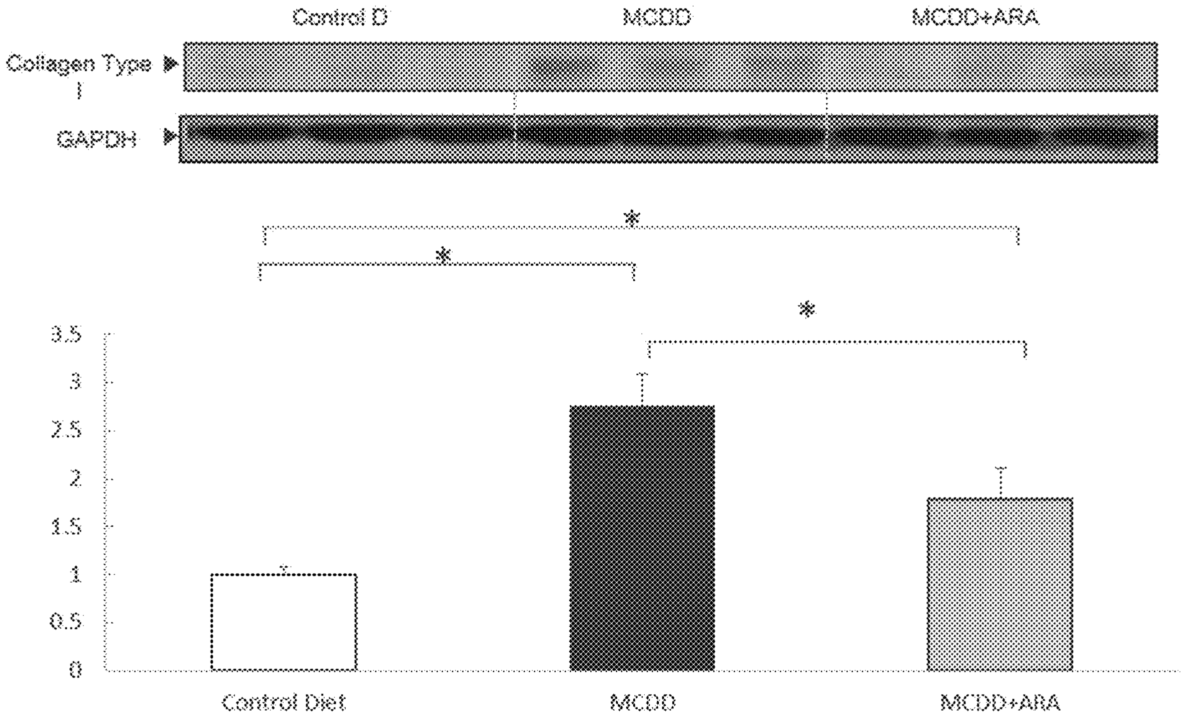
FIG. 9. depicts the effect of Aramchol™ on collagen production using liver extract from 0.1 MCD mice.
Figure 10A:
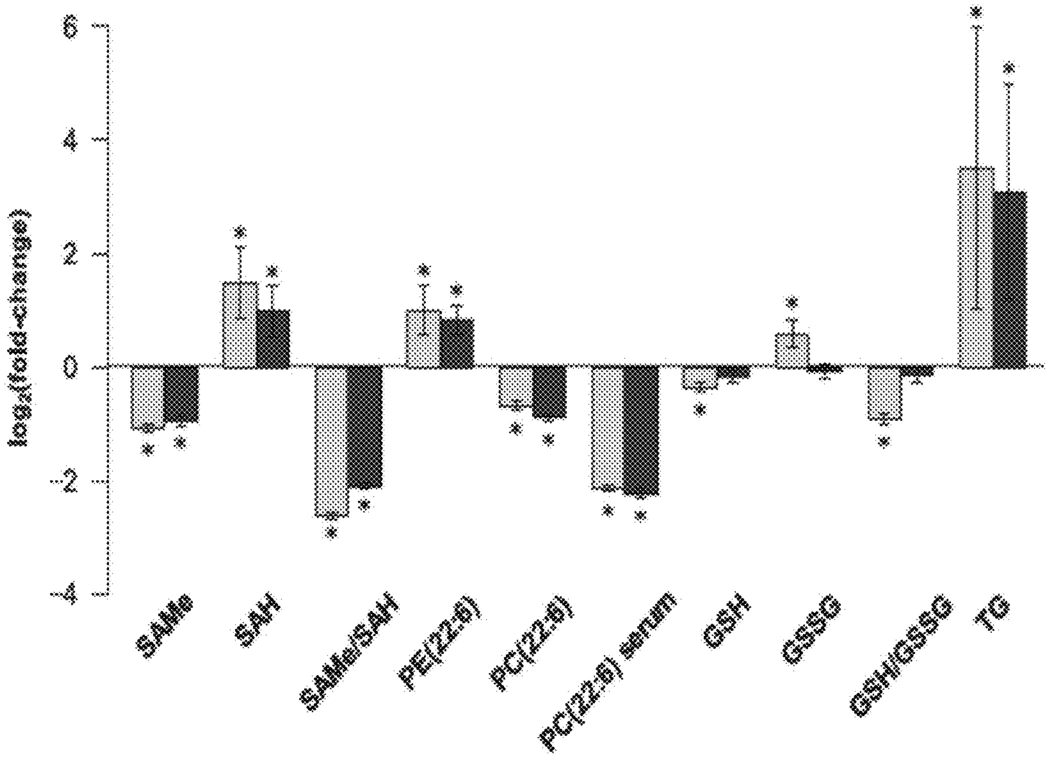
FIGS. 10A-10B depict the effects of Aramchol™ on liver biochemistry in 0.1 MCD mice.
Figure 10B:
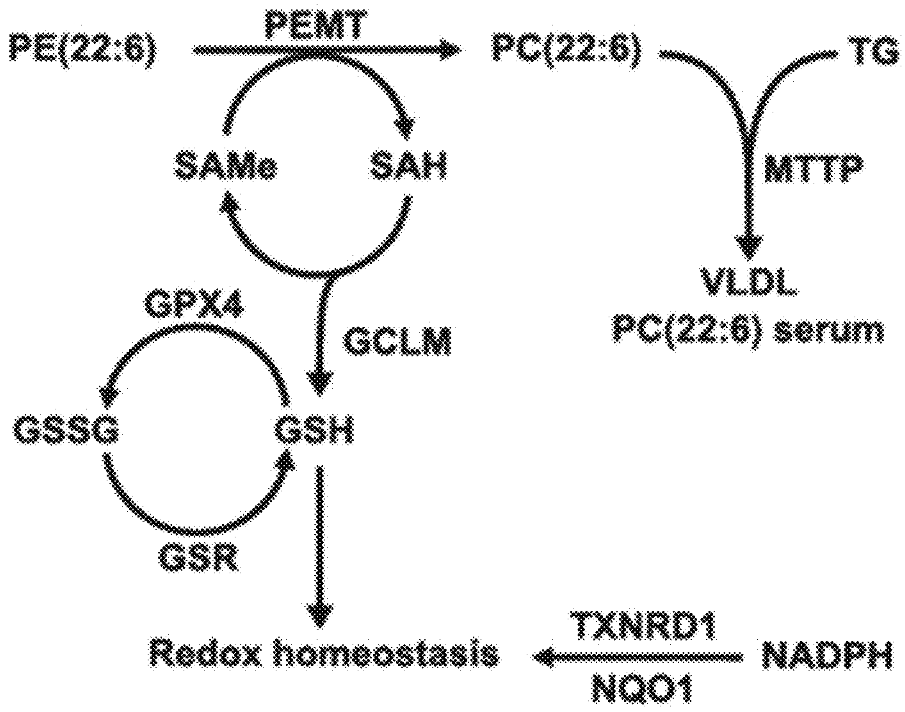

Results from the study showed: 1) treatment with Aramchol™ significantly down regulates steatosis in the liver (FIGS. 6A-6B); 2) treatment with Aramchol™ significantly down regulates/normalizes infiltration and activation status of macrophages in the liver (FIG. 7A-7C); 3) treatment with Aramchol™ significantly down regulates/normalizes fibrosis in the liver (FIGS. 8A-8B); 4) Aramchol™ significantly down regulates collagen in the liver (FIG. 9); and 5) Aramchol™ significantly up regulates glutathione and elevates GSH/GSSG ratio in 0.1% MCD mice (FIGS. 10A-10B).

Additionally, Aramchol™ treatment further reduced SCD1 activity, which was evidenced by a marked decrease in SCD1 expression, in the FA(16:1)/FA(16:0) ratio and in the total content of monounsaturated FA (MUFA), which led to a reduction in the hepatic content of diglycerides (DG) and TG. Aramchol™ treatment improved oxidative stress, as shown by the normalization of the GSH/GSSG ratio, a biomarker of the cellular redox potential, and a marked reduction in the content of total oxFA including oxLA, which has been associated with liver injury in human NASH.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Example 4

Brief Summary

This is a multicenter, Phase IIb, randomized, double blind, placebo-controlled study designed to evaluate the efficacy and safety of two Aramchol™ doses in subjects that are 18 to 75 years of age, with Non-Alcoholic Steatohepatitis (NASH) confirmed by liver biopsy performed in a period of 6 months before entering the study, with overweight or obesity and who are pre diabetic or type II diabetic.

Intervention

Drug: Aramchol™

Subjects will be administered Aramchol™ as follows:

a. One tablet of Aramchol™ 400 mg and one tablet of matching placebo for Aramchol™
b. One tablet of Aramchol™ 400 mg and one tablet of Aramchol™ 200 mg.
c. Two tablet of Aramchol™ matching placebo. The tablets should be taken orally in the morning within 30 min after breakfast with a glass of water (250 ml).

Subjects are allowed to omit study drugs up to 3 consecutive days during the study.

Other Name: Placebo

Study Arms

Experimental: Aramchol™ 600 mg a. One tablet of Aramchol™ 400 mg and one tablet of Aramchol™ 200 mg.
b. Intervention: Drug: Aramchol™

Experimental: Aramchol™ 400 mg a. One tablet of Aramchol™ 400 mg and one tablet of matching placebo for Aramchol™
b. Intervention: Drug: Aramchol™

Placebo Comparator: Placebo a. Two tablets of Aramchol™ matching placebo.
b. Intervention: Drug: Aramchol™

Estimated Enrollment

240

Inclusion Criteria

Male or female age 18 to 75 years.

BMI between 25 kg/m2 to 40 kg/m2 or waist circumference between 88 cm to 200 cm for women, and between 102 cm to 200 cm for men. If there is deviation above the upper limit, please consult the MRI center, to ensure that the machine is suitable for the patient.

Known type II Diabetes Mellitus or pre-Diabetes according to American Diabetes Association. One of the following 3 criteria is needed for pre-Diabetes: Fasting Plasma Glucose >100 mg/dl (5.5 mmol/l) or 2hPG following 75 g OGTT>140 (7.8 mmol/l) mg/dl or HbA1c >5.7%. HbA1c can be repeated at Investigator's discretion.

Histologically proven Steatohepatitis on a diagnostic liver biopsy performed either during screening or within 6 months before screening visit, confirmed by central laboratory reading of the slides. (Steatosis ≥1+inflammation ≥1+ballooning ≥1). Total activity NAS score of 4 or more.

Liver fat concentration in the liver of 5.5% or more as measured by NMRS.

Biopsies with an activity NAS score of 4 or more.

Normal synthetic liver function (serum albumin >3.2 g/dl, INR 0.8-1.2, conjugated bilirubin <35 μmol/L).

Understanding the nature of the study and signature of the written informed consent.

Negative pregnancy test at study entry for females of child bearing potential.

Females of child bearing potential practicing reliable contraception throughout the study period (including oral contraceptives) as well as negative pregnancy test at study entry.

Hypertensive patients must be well controlled by stable dose of anti-hypertensive medication for at least 2 months prior to screening.

Patients previously treated with vitamin E (>4001 U/day), Polyunsaturated fatty acid (>2 g/day) or Ursodeoxycholic acid or fish oil can be included if stopped or at least maintained on stable dose at least 3 months prior to diagnostic liver biopsy (and are not started during the trial). These treatments-dosages are allowed if they were stable for at least 12 months prior to biopsy and can remain stable throughout the study. (Dosages less than the amounts stated above are allowed without washout- or stable-period restrictions).

For patients with type II Diabetes, glycaemia must be controlled (Glycosylated Hemoglobin A1c ≤9%) while any HbA1c change should not exceed 1.5% during 6 months prior to enrolment). Treatments with anti-diabetic medications (except for those mentioned in Exclusion 16) are permitted if glycaemia is self-monitored by the patient. HbA1c can be repeated at Investigator's discretion.

Exclusion Criteria

Exclusion Criteria:

Patients with other active (acute or chronic) liver disease other than NASH (e.g. viral hepatitis, unless eradicated at least 3 years prior to screening; genetic hemochromatosis; Wilson disease; alpha lantitripsin deficiency; alcohol liver disease; drug-induced liver disease) at the time of randomization.

Patients with clinically or histologically documented liver cirrhosis

Known alcohol and/or any other drug abuse or dependence in the last five years.

Known history or presence of clinically significant cardiovascular, gastrointestinal, metabolic other than Diabetes Mellitus, neurologic, pulmonary, endocrine, psychiatric, neoplastic disorder or nephrotic syndrome, that in the opinion of the Investigator warrant exclusion from the study.

Patients with familial (i.e., genetic) hypertriglyceridemia and familial (i.e., genetic) hypercholesterolemia.

History or presence of any disease or condition known to interfere with the absorption distribution, metabolism or excretion of drugs including bile salt metabolites (e.g. inflammatory bowel disease (IBD)), previous intestinal (ileal or colonic) operation, chronic pancreatitis, celiac disease or previous vagotomy. Ongoing Chronic constipation Patients with heart or brain pacemaker (i.e., implantable neurological devices).

Surgery during the last three month before screening which involved stent implantation of metal devices (e.g. knee, hip etc.)

Weight loss of more than 5% within 6 months prior to randomization.

History of bariatric surgery within 5 years of liver biopsy.

Uncontrolled arterial hypertension.

Women who are pregnant and breast feeding.

Diabetes Mellitus other than type II (type I, endocrinopathy, genetic syndromes etc.).

Patients with HIV infection.

Daily alcohol intake >20 g/day for women and >30 g/day for men (on average per day) as per medical history.

Treatment with other anti-diabetic medications: GLP-1 receptor agonists and Thiazolidinediones (TZDs), unless started at least 12 months prior to biopsy and on stable dose for 6 months. In case of GLP-1 receptor agonists stopped, it should be at least 6 months before biopsy as per medical history.

SGLT-2 Inhibitors, Metformin, fibrates, statins, insulin, DPP-4 inhibitors and sulfonylurea unless prescribed dose has been stable for the last 6 months prior to the biopsy.

Treatment with Valproic acid, Tamoxifen, Methotrexate, Amiodarone or chronic treatment with anti-cholinergic agents, corticosteroids, high dose estrogen and tetracycline within 12 months prior to the screening visit.

Chronic treatment with antibiotics (e.g. Rifaximin).

Homeopathic and/or alternative treatments. Any treatment should be stopped during the screening period at least 48 hours before randomization.

Uncontrolled hypothyroidism defined as Thyroid Stimulating hormone >2× the upper limit of normal (ULN). Thyroid dysfunction controlled for at least 6 months prior to screening is permitted.

Patients with renal dysfunction eGFR<40.

Unexplained serum creatine phosphokinase (CPK) >3× the upper limit ofnormal (UNL). Patients with a reason for CPK elevation may have the measurement repeated prior to randomization; a CPK retest >3×ULN leads to exclusion.

Patients with condition(s) that makes them unsuitable to perform the NMRS (as determined by the PI or the MRI facility).

Hypersensitivity to Aramchol™ or to any of the excipients in the tablets

Hypersensitivity to cholic acid or bile acid sequestrants

Detailed Description

This is a multicenter, Phase IIb, randomized, double blind, placebo-controlled study designed to evaluate the efficacy and safety of two Aramchol™ doses in subjects that are 18 to 75 years of age, with Non-Alcoholic Steatohepatitis (NASH) confirmed by liver biopsy performed in a period of 6 months before entering the study, with overweight or obesity and who are pre diabetic or type II diabetic.

Eligible subjects will be enrolled into three treatments arms: Aramchol™ 400 and 600 mg tablets and placebo tablets in ratio 2:2:1.

The subjects will be evaluated at study sites for 11 scheduled visits: at screening (visit 1 (weeks −4-0)), baseline (visit 2 (day 0)), visit 3 (week 2), visit 4 week 4), visit 5

(week 8), visit 6 (week 12), visit 7 (week 24), visit 8 (week 32), visit 9 (week 40) and visit 10 (week 52-(End of Treatment/early termination visit)). After completion of the study treatment period, the subjects will be followed for an additional period of 13 weeks without study medication (until visit 11 (week 65)).

During the screening period, the severity of the disease will be evaluated with blood tests, liver biopsy and NMRS.

During the study the following assessments will be performed:

a. Vital signs will be measured at each study visit.
b. A physical examination will be performed at the screening visit, 24 weeks, End of Treatment/early termination and week 65 visit.

The following blood tests will be performed: complete blood count (CBC), serum chemistry (including electrolytes, liver enzymes, direct and total bilirubin, glucose, lipid profile which include triglyceride, cholesterol, HDL, LDL and VLDL, CPK, creatinine, urea, albumin, alkaline phosphatase), ESR and urinalysis during the screening visit, baseline, week 2, 4, 8, 24, 40, 52 and 65 (end of follow up) visits. Serology (HBV, HCV and HIV) will be performed during the screening visit. Coagulation (fibrinogen, PT/INR, aPTT) will be measured in screening and baseline, week 24, End of Treatment/early termination and week 65 visits. Insulin (HOMA) will be measured in the screening, week 24 and End of Treatment/early termination visits. HbA1C will be measured in the screening, week 8, 24, 40 and End of Treatment/early termination visits. C reactive protein, Leptin, Adiponectin, CK-18 (M30 and M65), Ferritin, PAI-1, IL-6, TNF-alpha, FGF-19, C4 (7-alpha-hydroxy-4-cholesten-3-one), pool serum Bile Acids, B-hydroxybutyrate and Free Fatty Acids will be measured in baseline visit and end of treatment period. The blood samples taken at these visits, will be tested for possible biomarkers, including, but not limited to, Fetuine A and GDF15. TSH, T3 and T4 will be measured during the screening visit. beta-hCG in women of childbearing potential will be performed during the screening visit. A serum sample will be collected and kept frozen until study end in case special investigation needs to be performed. This sample will be collected during the screening and visit 10/Early Termination.

Body weight and waist circumference will be measured in screening, baseline, week 24, end of treatment and week 65 visits. Height will be measured during the screening visit.

ECG will be performed during the screening visit, visit 7 (week 24) and end of treatment visits.

All subjects will undergo two NMRS scans, at screening and end of treatment visits.

FibroMax test will be performed only if the investigator thinks it is necessary

Liver biopsy will be conducted during the screening and end of treatment visit. The biopsy in the screening visit will be performed only if it was not done within the 6 months prior to this visit.

Metabolomics blood test will be performed at the screening, visit 7 and the End-of-Treatment/Early Termination visits. From some consenting patients (about 15) a sample from the liver biopsy will be taken for analysis.

Endothelial Function will be conducted in selected sites. The test will be conducted during the baseline visit before the study treatment will be given and End of Treatment/early termination visit.

Blood sample for Aramchol™ trough level will be collected (pre-dose) from patients in Israel at baseline (visit 2) week 4 (visit 4), week 12 (visit 6), week 24 (visit 7), week 40 (visit 9), end of treatment (visit 10) and follow up (visit 11). At selected sites in Mexico, USA and Hong Kong one blood sample will be collected (pre-dose) on visit 4 (up to 10 subjects per country) to test for trough Aramchol™ blood level differences between populations (e.g., African American, Asian, Hispanic).

Blood sample for gene analysis will be taken from all consenting patients during the baseline visit, will be kept frozen and analyzed only at the study end.

Life style questionnaire will be completed in all visits.

Adverse events will be monitored throughout the study.

Concomitant Medications will be monitored throughout the study.

Telephone contacts will be performed on week 16, 20, 28, 36, 44 and 48. An interim safety analysis will be conducted as soon as 120 subjects will completed the follow up period of 24 weeks under study treatment. An independent DSMB will analyze the safety data and recommend a continued course of action. All patients will continue to be treated under the study protocol until conclusion of the analysis will be known.

Safety assessment will include frequency and severity of treatment-emergent AEs, clinically significant laboratory abnormalities, ECG changes and physical examination findings.

Results

Primary and Secondary Outcome Measures (400 mg arm)

Treatment with 400 mg of Aramchol™ significantly reduces liver triglycerides ratio as measured by Magnetic Resonance Spectroscopy (MRS).

Treatment with 400 mg of Aramchol™ reduces liver triglycerides ratio as measured by Magnetic Resonance Spectroscopy (MRS) by 10-40%.

Treatment with 400 mg of Aramchol™ reduces liver triglycerides ratio as measured by Magnetic Resonance Spectroscopy (MRS) by 15%-35%.

Treatment with 400 mg of Aramchol™ reduces liver triglycerides ratio as measured by Magnetic Resonance Spectroscopy (MRS) by 20%-30%.

Treatment with 400 mg of Aramchol™ results in a significantly higher proportion of subjects having fibrosis improvement (i.e. decrease > or =to 1 point) without a worsening of NASH, compared to subjects treated with a placebo.

Treatment with 400 mg of Aramchol™ results in a significantly higher proportion of subjects having fibrosis improvement (i.e. decrease > or =to 1 point) without a worsening of NASH, compared to subjects treated with a placebo. The improvement ratio is at least 2 when compared to subjects treated with a placebo.

Treatment with 400 mg of Aramchol™ results in a significantly higher proportion of subjects with NAS Score improvement (i.e. improvement of at least 2 points) without worsening of fibrosis score, compared to subjects treated with a placebo.

Treatment with 400 mg of Aramchol™ results in a significantly higher proportion of subjects with SAF Activity score improvement (i.e. improvement of at least 2 points) without worsening of fibrosis score, compared to subjects treated with a placebo.

Treatment with 400 mg of Aramchol™ results in a significantly higher proportion of subjects with NASH resolution (ballooning of 0, inflammation of 0 or 1) without worsening of fibrosis, compared to subjects treated with a placebo.

Exploratory Outcome Measures (400 mg arm)

Treatment with 400 mg of Aramchol™ inhibits worsening of the subject's fibrosis score significantly more than what would be expected based on Aramchol™'s effect on the subject's liver triglycerides.

Treatment with 400 mg of Aramchol™ to subjects afflicted with hepatic fibrosis improves the subject's fibrosis score significantly more than what would be expected based on Aramchol™'s effect on the subject's liver triglycerides.

Treatment with 400 mg of Aramchol™ to subjects afflicted with stage 1a hepatic fibrosis improves the subject's fibrosis score significantly more than the effect that would be expected based on Aramchol™'s effect on the subject's liver triglycerides.

Treatment with 400 mg of Aramchol™ to subjects afflicted with stage 1b hepatic fibrosis improves the subject's fibrosis score significantly more than the effect that would be expected based on Aramchol™'s effect on the subject's liver triglycerides.

Treatment with 400 mg of Aramchol™ to subjects afflicted with stage 1c hepatic fibrosis improves the subject's fibrosis score significantly more than the effect that would be expected based on Aramchol™'s effect on the subject's liver triglycerides.

Treatment with 400 mg of Aramchol™ to subjects afflicted with stage 2 hepatic fibrosis improves the subject's fibrosis score significantly more than the effect that would be expected based on Aramchol™'s effect on the subject's liver triglycerides.

Treatment with 400 mg of Aramchol™ to subjects afflicted with stage 3 hepatic fibrosis improves the subject's fibrosis score significantly more than the effect that would be expected based on Aramchol™'s effect on the subject's liver triglycerides.

Treatment with 400 mg of Aramchol™ to subjects afflicted with stage 4 hepatic fibrosis improves the subject's fibrosis score significantly more than the effect that would be expected based on Aramchol™'s effect on the subject's liver triglycerides.

Treatment with 400 mg of Aramchol™ to subjects afflicted with hepatic fibrosis improves the subject's SAF score more than what would be expected based on Aramchol™'s effect on the subject's liver triglycerides.

Treatment with 400 mg of Aramchol™ to subjects afflicted with hepatic fibrosis results in a significantly higher proportion of subjects without worsening of fibrosis score, compared to subjects afflicted with hepatic fibrosis treated with a placebo.

Treatment with 400 mg of Aramchol™ to subjects afflicted with hepatic fibrosis results in a significantly higher proportion of subjects having fibrosis improvement (i.e. decrease > or =to 1 point), compared to subjects afflicted with hepatic fibrosis treated with a placebo.

Treatment with 400 mg of Aramchol™ to subjects afflicted with hepatic fibrosis results in a significantly higher proportion of subjects having fibrosis improvement (i.e. decrease > or =to 1 point) without a worsening of NASH, compared to subjects afflicted with hepatic fibrosis treated with a placebo.

Treatment with 400 mg of Aramchol™ to subjects afflicted with hepatic fibrosis results in a significantly higher proportion of subjects having fibrosis improvement (i.e. decrease > or =to 1 point) without a worsening of NASH, compared to subjects treated with a placebo. The improvement ratio is at least 2 when compared to subjects afflicted with hepatic fibrosis treated with a placebo.

Treatment with 400 mg of Aramchol™ results in a significantly higher proportion of subjects with NAS Score improvement (i.e. improvement of at least 2 points) compared to subjects afflicted with hepatic fibrosis treated with a placebo.

Treatment with 400 mg of Aramchol™ results in a significantly higher proportion of subjects with NAS Score improvement (i.e. improvement of at least 2 points) without worsening of fibrosis score, compared to subjects afflicted with hepatic fibrosis treated with a placebo.

Treatment with 400 mg of Aramchol™ to subjects afflicted with hepatic fibrosis results in a significantly higher proportion of subjects with SAF Activity score improvement (i.e. improvement of at least 2 points) compared to subjects afflicted with hepatic fibrosis treated with a placebo.

Treatment with 400 mg of Aramchol™ to subjects afflicted with hepatic fibrosis results in a significantly higher proportion of subjects with SAF Activity score improvement (i.e. improvement of at least 2 points) without worsening of fibrosis score, compared to subjects afflicted with hepatic fibrosis treated with a placebo.

Treatment with 400 mg of Aramchol™ to subjects afflicted with hepatic fibrosis results in a significantly higher proportion of subjects with NASH resolution (ballooning of 0, inflammation of 0 or 1) compared to subjects afflicted with hepatic fibrosis treated with a placebo.

Treatment with 400 mg of Aramchol™ to subjects afflicted with hepatic fibrosis results in a significantly higher proportion of subjects with NASH resolution (ballooning of 0, inflammation of 0 or 1) without worsening of fibrosis, compared to subjects afflicted with hepatic fibrosis treated with a placebo.

Treatment with 400 mg of Aramchol™ to subjects not afflicted with hepatic fibrosis results in a significantly higher proportion of subjects without worsening of fibrosis score, compared to subjects not afflicted with hepatic fibrosis treated with a placebo.

Treatment with 400 mg of Aramchol™ results in a significantly higher proportion of subjects with NAS Score improvement (i.e. improvement of at least 2 points) compared to subjects not afflicted with hepatic fibrosis treated with a placebo.

Treatment with 400 mg of Aramchol™ results in a significantly higher proportion of subjects with NAS Score improvement (i.e. improvement of at least 2 points) without worsening of fibrosis score, compared to subjects not afflicted with hepatic fibrosis treated with a placebo.

Treatment with 400 mg of Aramchol™ to subjects not afflicted with hepatic fibrosis results in a significantly higher proportion of subjects with SAF Activity score improvement (i.e. improvement of at least 2 points) compared to subjects not afflicted with hepatic fibrosis treated with a placebo.

Treatment with 400 mg of Aramchol™ to subjects not afflicted with hepatic fibrosis results in a significantly higher proportion of subjects with SAF Activity score improvement (i.e. improvement of at least 2 points) without worsening of fibrosis score, compared to subjects not afflicted with hepatic fibrosis treated with a placebo.

Treatment with 400 mg of Aramchol™ to subjects not afflicted with hepatic fibrosis results in a significantly higher proportion of subjects with NASH resolution (ballooning of 0, inflammation of 0 or 1) compared to subjects not afflicted with hepatic fibrosis treated with a placebo.

Treatment with 400 mg of Aramchol™ to subjects not afflicted with hepatic fibrosis results in a significantly higher proportion of subjects with NASH resolution (ballooning of 0, inflammation of 0 or 1) without worsening of fibrosis, compared to subjects not afflicted with hepatic fibrosis treated with a placebo.

Primary and Secondary Outcome Measures (600 mg Arm)

Treatment with 600 mg of Aramchol™ significantly reduces liver triglycerides ratio as measured by Magnetic Resonance Spectroscopy (MRS).

Treatment with 600 mg of Aramchol™ reduces liver triglycerides ratio as measured by Magnetic Resonance Spectroscopy (MRS) by 10-40%.

Treatment with 600 mg of Aramchol™ reduces liver triglycerides ratio as measured by Magnetic Resonance Spectroscopy (MRS) by 15%-35%.

Treatment with 600 mg of Aramchol™ reduces liver triglycerides ratio as measured by Magnetic Resonance Spectroscopy (MRS) by 20%-30%.

Treatment with 600 mg of Aramchol™ results in a significantly higher proportion of subjects having fibrosis improvement (i.e. decrease > or =to 1 point) without a worsening of NASH, compared to subjects treated with a placebo.

Treatment with 600 mg of Aramchol™ results in a significantly higher proportion of subjects having fibrosis improvement (i.e. decrease > or =to 1 point) without a worsening of NASH, compared to subjects treated with a placebo. The improvement ratio is at least 2 when compared to subjects treated with a placebo.

Treatment with 600 mg of Aramchol™ results in a significantly higher proportion of subjects with NAS Score improvement (i.e. improvement of at least 2 points) without worsening of fibrosis score, compared to subjects treated with a placebo.

Treatment with 600 mg of Aramchol™ results in a significantly higher proportion of subjects with SAF Activity score improvement (i.e. improvement of at least 2 points) without worsening of fibrosis score, compared to subjects treated with a placebo.

Treatment with 600 mg of Aramchol™ results in a significantly higher proportion of subjects with NASH resolution (ballooning of 0, inflammation of 0 or 1) without worsening of fibrosis, compared to subjects treated with a placebo.

Exploratory Outcome Measures (600 mg Arm)

Treatment with 600 mg of Aramchol™ inhibits worsening of the subject's fibrosis score significantly more than what would be expected based on Aramchol™'s effect on the subject's liver triglycerides.

Treatment with 600 mg of Aramchol™ to subjects afflicted with hepatic fibrosis improves the subject's fibrosis score significantly more than what would be expected based on Aramchol™'s effect on the subject's liver triglycerides.

Treatment with 600 mg of Aramchol™ to subjects afflicted with stage 1a hepatic fibrosis improves the subject's fibrosis score significantly more than the effect that would be expected based on Aramchol™'s effect on the subject's liver triglycerides.

Treatment with 600 mg of Aramchol™ to subjects afflicted with stage 1b hepatic fibrosis improves the subject's fibrosis score significantly more than the effect that would be expected based on Aramchol™'s effect on the subject's liver triglycerides.

Treatment with 600 mg of Aramchol™ to subjects afflicted with stage 1c hepatic fibrosis improves the subject's fibrosis score significantly more than the effect that would be expected based on Aramchol™'s effect on the subject's liver triglycerides.

Treatment with 600 mg of Aramchol™ to subjects afflicted with stage 2 hepatic fibrosis improves the subject's fibrosis score significantly more than the effect that would be expected based on Aramchol™'s effect on the subject's liver triglycerides.

Treatment with 600 mg of Aramchol™ to subjects afflicted with stage 3 hepatic fibrosis improves the subject's fibrosis score significantly more than the effect that would be expected based on Aramchol™'s effect on the subject's liver triglycerides.

Treatment with 600 mg of Aramchol™ to subjects afflicted with stage 4 hepatic fibrosis improves the subject's fibrosis score significantly more than the effect that would be expected based on Aramchol™'s effect on the subject's liver triglycerides.

Treatment with 600 mg of Aramchol™ to subjects afflicted with hepatic fibrosis improves the subject's SAF score more than what would be expected based on Aramchol™'s effect on the subject's liver triglycerides.

Treatment with 600 mg of Aramchol™ to subjects afflicted with hepatic fibrosis results in a significantly higher proportion of subjects without worsening of fibrosis score, compared to subjects afflicted with hepatic fibrosis treated with a placebo.

Treatment with 600 mg of Aramchol™ to subjects afflicted with hepatic fibrosis results in a significantly higher proportion of subjects having fibrosis improvement (i.e. decrease > or =to 1 point), compared to subjects afflicted with hepatic fibrosis treated with a placebo.

Treatment with 600 mg of Aramchol™ to subjects afflicted with hepatic fibrosis results in a significantly higher proportion of subjects having fibrosis improvement (i.e. decrease > or =to 1 point) without a worsening of NASH, compared to subjects afflicted with hepatic fibrosis treated with a placebo.

Treatment with 600 mg of Aramchol™ to subjects afflicted with hepatic fibrosis results in a significantly higher proportion of subjects having fibrosis improvement (i.e. decrease > or =to 1 point) without a worsening of NASH, compared to subjects treated with a placebo. The improvement ratio is at least 2 when compared to subjects afflicted with hepatic fibrosis treated with a placebo.

Treatment with 600 mg of Aramchol™ results in a significantly higher proportion of subjects with NAS Score improvement (i.e. improvement of at least 2 points) compared to subjects afflicted with hepatic fibrosis treated with a placebo.

Treatment with 600 mg of Aramchol™ results in a significantly higher proportion of subjects with NAS Score improvement (i.e. improvement of at least 2 points) without worsening of fibrosis score, compared to subjects afflicted with hepatic fibrosis treated with a placebo.

Treatment with 600 mg of Aramchol™ to subjects afflicted with hepatic fibrosis results in a significantly higher proportion of subjects with SAF Activity score improvement (i.e. improvement of at least 2 points) compared to subjects afflicted with hepatic fibrosis treated with a placebo.

Treatment with 600 mg of Aramchol™ to subjects afflicted with hepatic fibrosis results in a significantly higher proportion of subjects with SAF Activity score improvement (i.e. improvement of at least 2 points) without worsening of fibrosis score, compared to subjects afflicted with hepatic fibrosis treated with a placebo.

Treatment with 600 mg of Aramchol™ to subjects afflicted with hepatic fibrosis results in a significantly higher proportion of subjects with NASH resolution (ballooning of 0, inflammation of 0 or 1) compared to subjects afflicted with hepatic fibrosis treated with a placebo.

Treatment with 600 mg of Aramchol™ to subjects afflicted with hepatic fibrosis results in a significantly higher proportion of subjects with NASH resolution (ballooning of 0, inflammation of 0 or 1) without worsening of fibrosis, compared to subjects afflicted with hepatic fibrosis treated with a placebo.

Treatment with 600 mg of Aramchol™ to subjects not afflicted with hepatic fibrosis results in a significantly higher proportion of subjects without worsening of fibrosis score, compared to subjects not afflicted with hepatic fibrosis treated with a placebo.

Treatment with 600 mg of Aramchol™ results in a significantly higher proportion of subjects with NAS Score improvement (i.e. improvement of at least 2 points) compared to subjects not afflicted with hepatic fibrosis treated with a placebo.

Treatment with 600 mg of Aramchol™ results in a significantly higher proportion of subjects with NAS Score improvement (i.e. improvement of at least 2 points) without worsening of fibrosis score, compared to subjects not afflicted with hepatic fibrosis treated with a placebo.

Treatment with 600 mg of Aramchol™ to subjects not afflicted with hepatic fibrosis results in a significantly higher proportion of subjects with SAF Activity score improvement (i.e. improvement of at least 2 points) compared to subjects not afflicted with hepatic fibrosis treated with a placebo.

Treatment with 600 mg of Aramchol™ to subjects not afflicted with hepatic fibrosis results in a significantly higher proportion of subjects with SAF Activity score improvement (i.e. improvement of at least 2 points) without worsening of fibrosis score, compared to subjects not afflicted with hepatic fibrosis treated with a placebo.

Treatment with 600 mg of Aramchol™ to subjects not afflicted with hepatic fibrosis results in a significantly higher proportion of subjects with NASH resolution (ballooning of 0, inflammation of 0 or 1) compared to subjects not afflicted with hepatic fibrosis treated with a placebo.

Treatment with 600 mg of Aramchol™ to subjects not afflicted with hepatic fibrosis results in a significantly higher proportion of subjects with NASH resolution (ballooning of 0, inflammation of 0 or 1) without worsening of fibrosis, compared to subjects not afflicted with hepatic fibrosis treated with a placebo.

Discussion

Based on studies described herein, Aramchol™ is surprisingly found to be a potent anti-fibrotic and anti-cirrhotic agent. Aramchol™ is also found to be unexpectedly superior to OCA and provides improved, effective treatment for liver fibrosis. Accordingly, Aramchol™ may be used to prevent acute or fatal liver failure and/or hepatic or portosystemic encephalopathy, for example toxin-induced liver failure and/or hepatic encephalopathy.

Furthermore, Aramchol™ is also surprisingly found to be effective in reversing established fibrosis. Aramchol™ treatment improves liver histology as determined by a reduction of lipid accumulation (Sudan red staining), fibrosis (Sirius red and SMA staining) and inflammation (F4/80 and CD64 staining). Indeed, Aramchol™ has an effect on fibrosis in addition to main pathologies of NASH, namely steatosis and inflammation.

Results presented herein show that Aramchol™ downregulates collagen production from human stellate cells, the effects of Aramchol™ are mediated through down regulation of SCD 1 and up regulation of glutathione production, and the effect of Aramchol™ on fibrosis is mediated via down regulation of steatosis and inflammation as well as directly via down regulation of collagen production from stellate cells. Taken together, information herein supports the effects of Aramchol™ in human patients as set forth in the claims.

Results analogous to those of Example 4 for 400 mg or 600 mg doses are expected for higher doses of Aramchol™ that are recited herein.

Example 5: In Vivo Studies with Aramchol™, a Stearoyl CoA Desaturase Inhibitor, in Human Subjects with NASH. One-Year Results of the Global Phase 2b Randomized Placebo-Controlled ARREST Trial In a 3-month, phase 2a human NAFLD study, Aramchol™ reduced hepatic fat. It also had antifibrotic effects in preclinical models.

The final results from the global phase 2b ARREST study evaluating a 1-year treatment with Aramchol™ in patients (pts) with NASH are reported herein.

Methods

Overweight/obese pts with pre-diabetes or diabetes and biopsy-proven NASH (with NAS≥4; F<4) were included. Liver biopsy and liver fat measurement by MR spectroscopy (LF-MRS) were performed at baseline and week 52. Both read centrally. The primary endpoint was the absolute change from baseline in LF-MRS (600 mg vs. placebo, PLB; mixed model repeated measures). Key secondary endpoints included: NASH resolution without fibrosis worsening, >1 stage fibrosis reduction without NASH worsening and ALT reduction.

Results 247 pts from 11 countries (US, Europe, Latin America) were randomized 2:2:1 to Aramchol™ 400 mg QD (N=101), 600 mg QD (N=98) or PLB (N=48). At baseline: 65% females, mean age 54.4 yrs, BMI 32.7 kg/m2, HbA1c 6.6%+1.0% (mean±SD), LF-MRS 28.5%+11.7% (mean±SD); 60% fibrosis stage 2-3 and NAS 5.12±1.00 (mean±SD). 89% of pts completed the study. The results of the study are summarized in FIGS. 16A-16B to FIGS. 20A-20B.

Figure 16A:
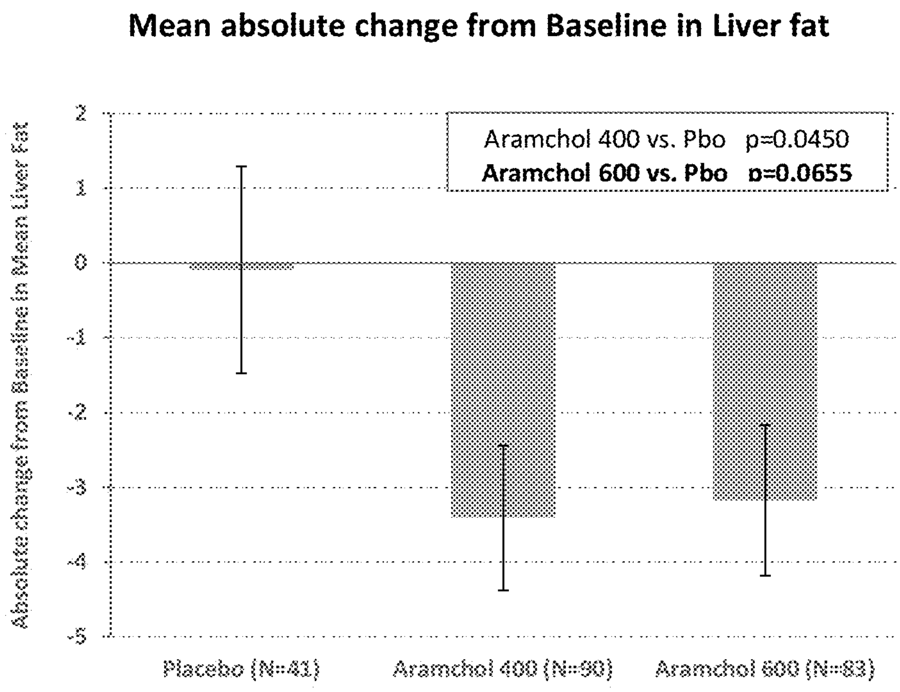
FIGS. 16A-16B depict the reduction in liver fat in human subjects receiving 400 mg, 600 mg doses of Aramchol™ and placebo.
Figure 16B:
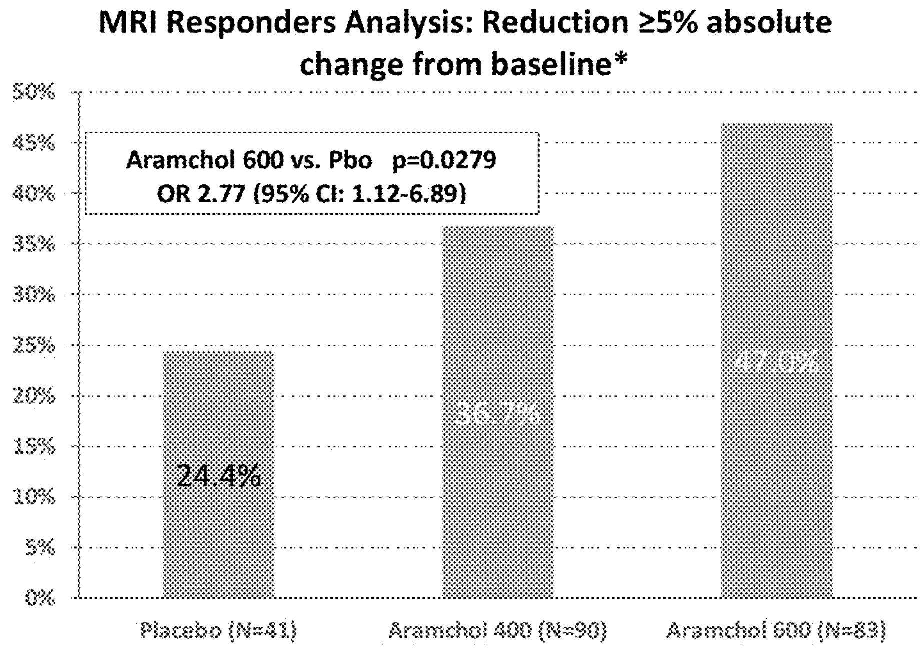
Figure 17A:
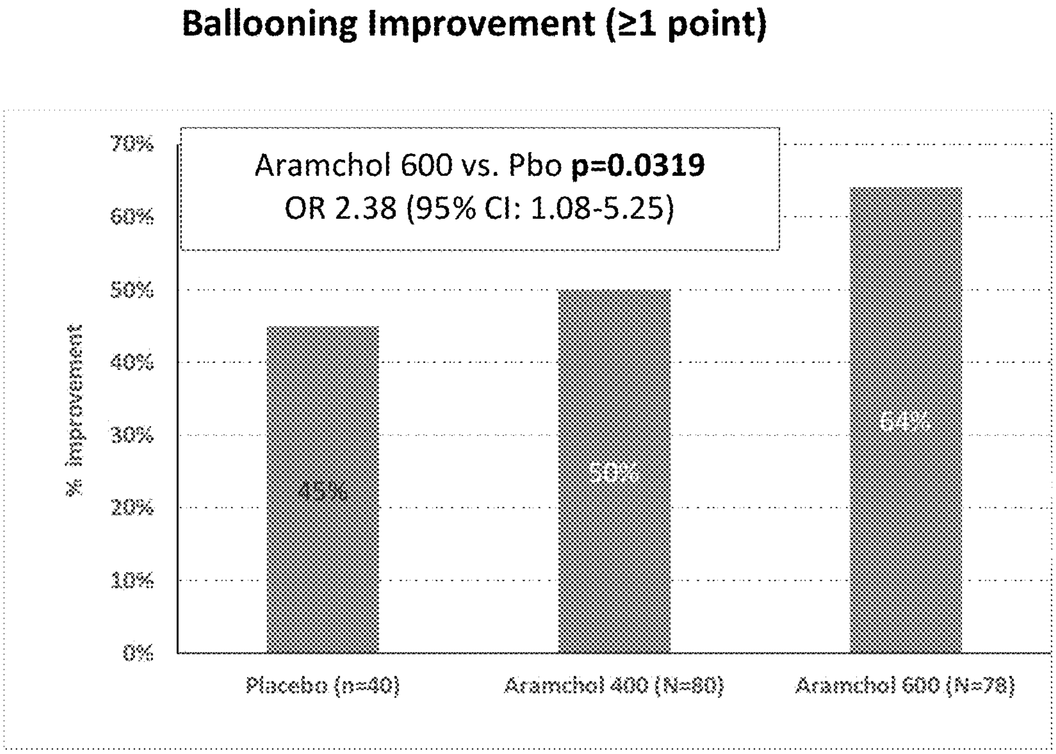
FIGS. 17A-17B depict the reduction in ballooning in human subjects receiving 400 mg, 600 mg doses of Aramchol™ and placebo.
Figure 17B:
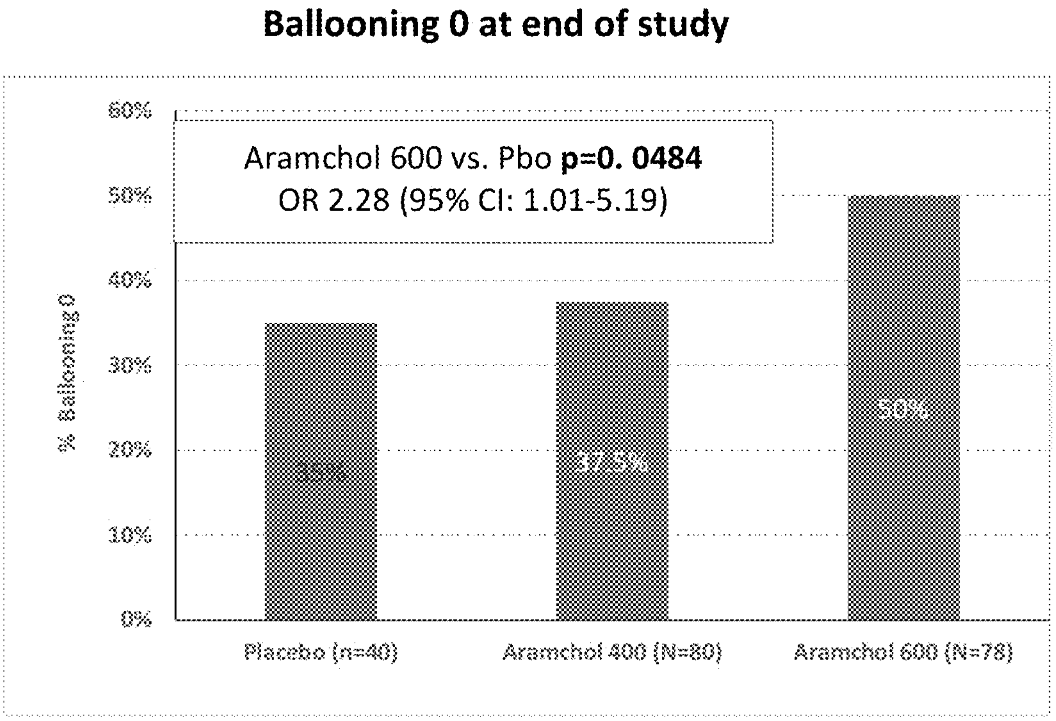
Figure 18A:
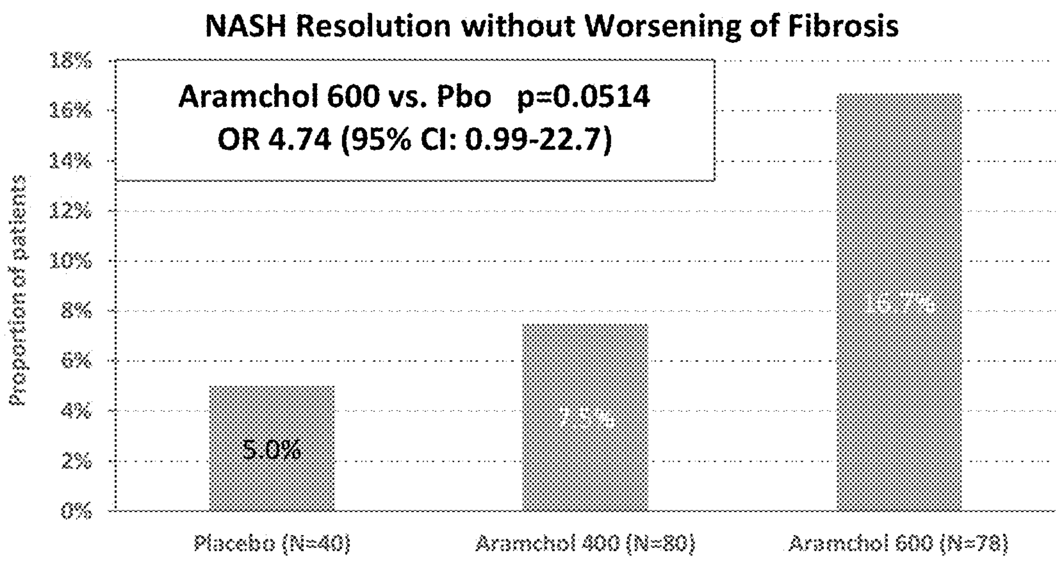
FIGS. 18A-18B depict the NASH Resolution without worsening of Fibrosis demonstrated in human subjects receiving 400 mg, 600 mg doses of Aramchol™ and placebo.
Figure 18B:
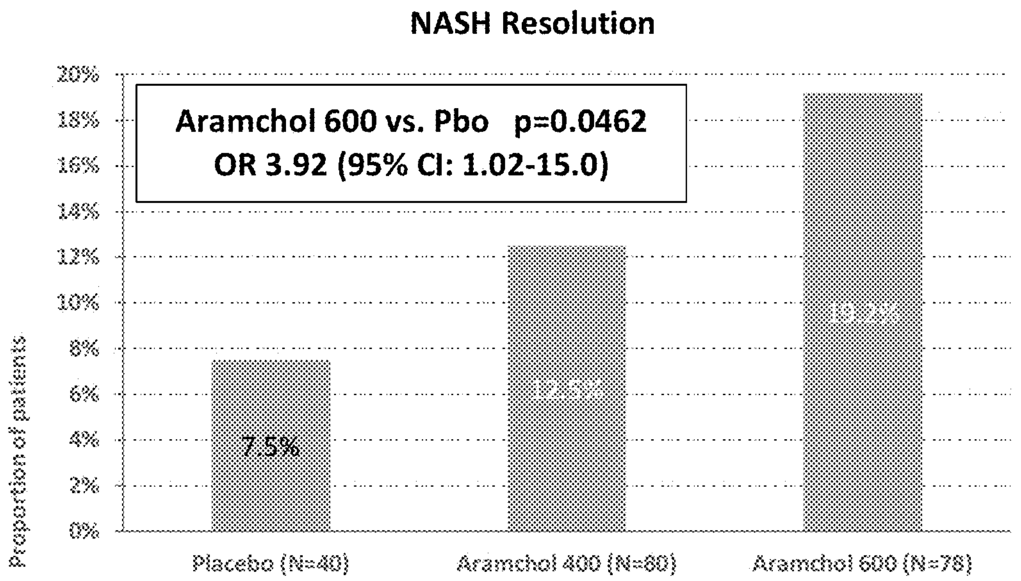
Figure 19A:
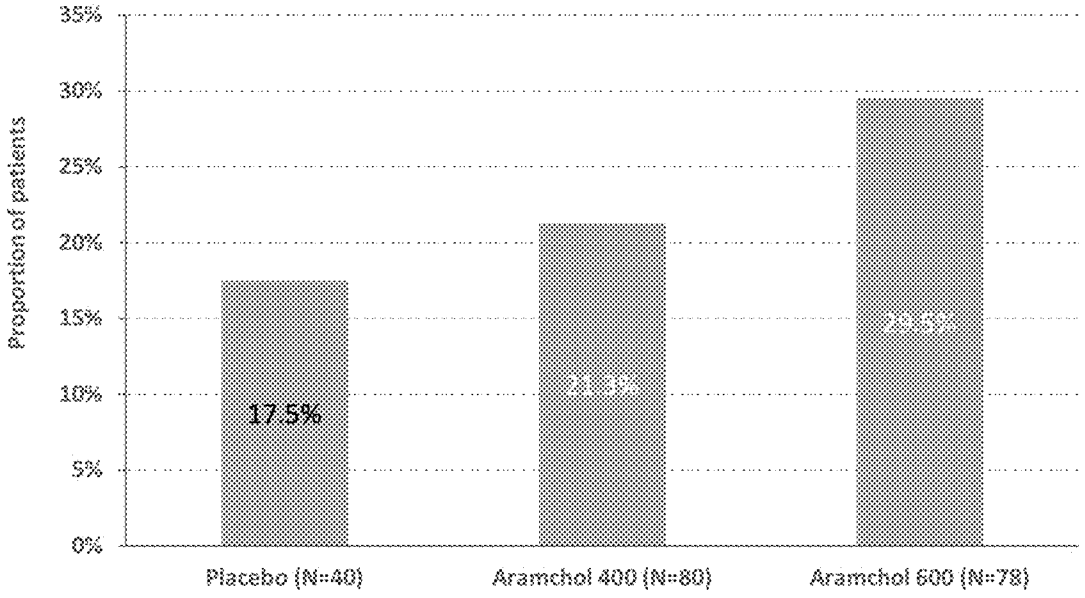
FIGS. 19A-19B depict the fibrosis improvement and the progression to Cirrhosis as demonstrated in human subjects receiving 400 mg, 600 mg doses of Aramchol™ and placebo.
Figure 19B:
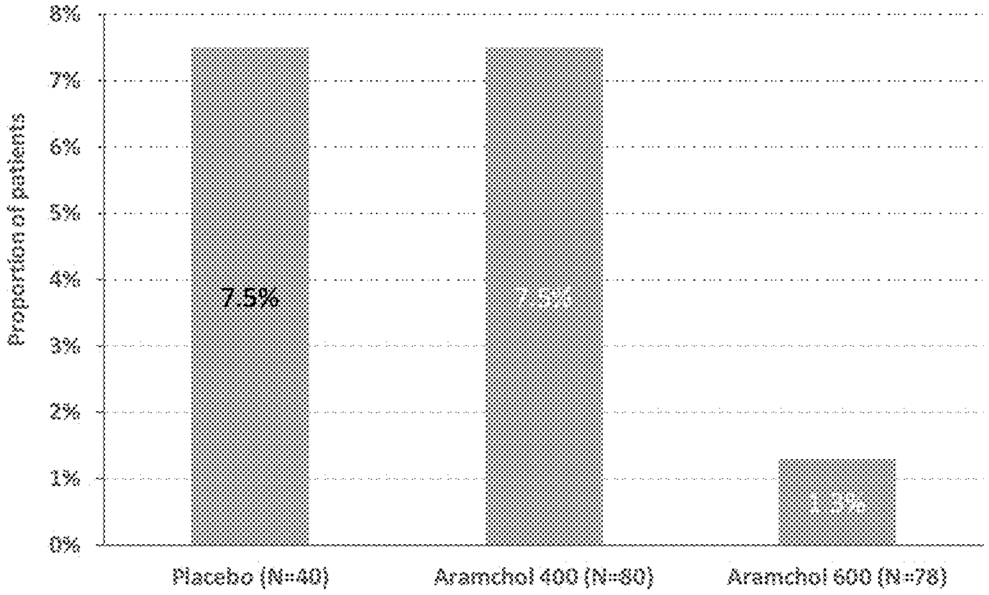
Figure 20A:
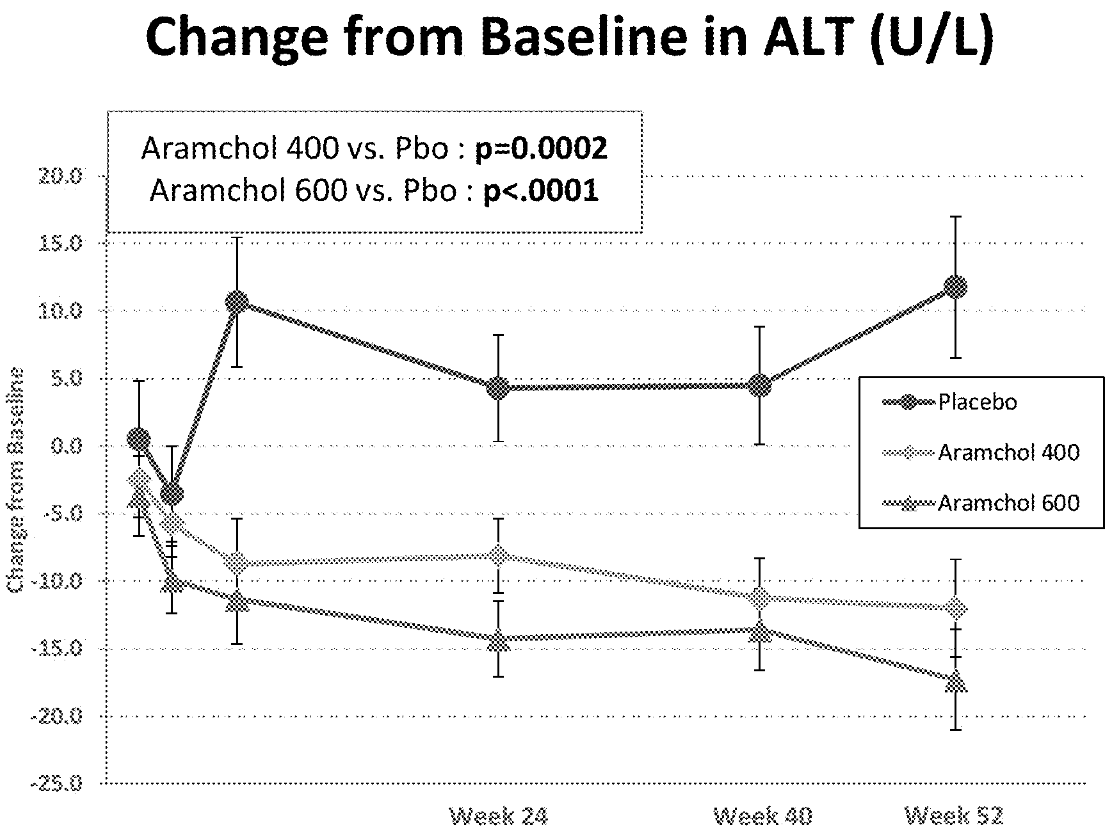
FIGS. 20A-20B depict the Aramchol™ effect on ALT and AST levels as demonstrated in human subjects receiving 400 mg, 600 mg doses of Aramchol™ and placebo.
Figure 20B:
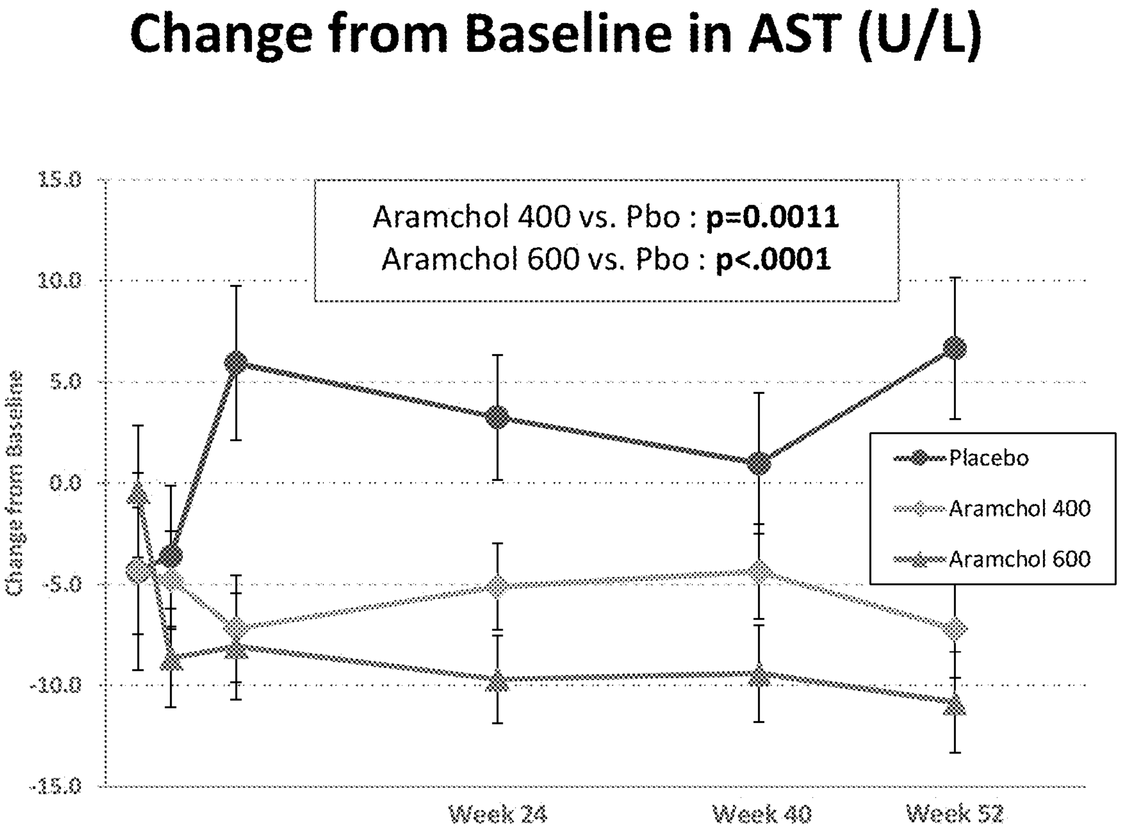

LF-MRS was significantly reduced vs PLB by 400 mg (p=0.045) and 600 mg (p<0.066). A statistically significant >5% absolute reduction in liver fat was seen in 47% of pts on 600 mg vs 24% on PLB (p<0.028) and 37% on 400 mg suggesting a dose response (FIG. 16B). Pts in the 600 mg arm had NASH resolution without fibrosis worsening more often than PLB: 16.7% vs. 5.0% respectively, (OR=4.74, 95% CI: 0.99-22.66, p=0.051)(FIG. 18A). A >1 stage fibrosis reduction without NASH worsening occurred in 29.5% of the 600 mg arm vs 17.5% of the PLB arm (p=0.21)(FIG. 19A). One (1.3%) pt progressed to cirrhosis in the 600 mg arm vs 6 (7.5%) in the 400 mg arm and 3 (7.5%) in the PLB arm (FIG. 19B). Both doses significantly reduced ALT (p<0.001)(FIG. 20A), AST (p=0.002)(FIG. 20B) and HbA1c (p<0.007) vs PLB in a dose response manner. Serum lipid parameters and body weight did not change. Discontinuation due to adverse events (AE) was <5% and serious AE occurred in 10% of pts without a difference between arms.

Conclusion

In a one year, PLB-controlled, phase 2b trial in pts with NASH, Aramchol™ significantly reduced liver fat, improved histology, hepatic biochemistry and glycemic control with excellent safety and tolerability. The therapeutic potency of Aramchol™ for NASH should be tested in a larger, phase 3 trial.

Example 6: In Vivo Studies with Aramchol™, in Human Subjects with NASH. Modelling and Simulation of 300 mg BID and 600 mg OD Doses of ARAMCHOL™ in Patients Table 1 summarizes the reported plasma exposure from three studies—single dose Phase I in healthy volunteers (30-900 mg, AUC=$AUC_{inf}$); Phase II ARAMCHOL™ 003 repeat dose study (AUC on D84 from 100 & 300 mg QD), Phase IIb Cmin on D84 (400 and 600 mg QD).

TABLE 1

Summary of exposure data in healthy volunteers and patients.

| Study | Dose (mg) | SS Cmin (ng/mL) | AUC (ng/mL · h) | AUC/Dose (ng/mL · h/ (mg/kg)) | Relative bioavailability (AUC/Dose normalized to 30 mg HV data) |
|---|---|---|---|---|---|
| Phase 1 single dose | 30 | | 11919 | 397 | 1 |
| healthy volunteers | 100 | | 25698 | 257 | 0.65 |
| | 300 | | 64285 | 214 | 0.54 |
| | 900 | | 86943 | 97 | 0.24 |
| Phase 2 | 100 | | 19738 | 197 | 0.50 |
| ARAMCHOL ™ 003 | 300 | | 32992 | 110 | 0.28 |
| Phase 2b (Report ref | 400 | 2859 | 68616* | 172 | 0.43 |
| Summary of Through ARAMCHOL ™ Concentrations 081320180536) | 600 | 3611 | 86664* | 144 | 0.36 |

Figure 11:
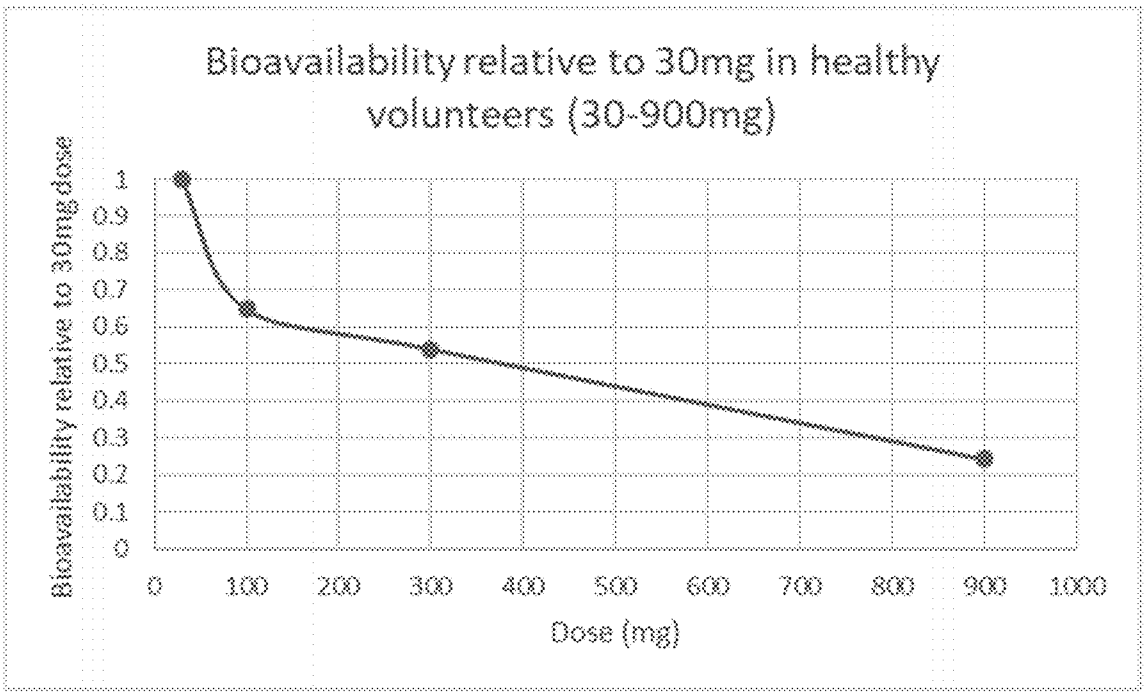
FIG. 11 depicts the bioavailability of 100 mg, 300 mg and 900 mg doses, relative to 30 mg dose in healthy volunteers. Relative oral bioavailability in healthy volunteers decreases with increasing dose across the range 30-900 mg.

Exposure in healthy volunteers is sub-proportional with an approximate four-fold decrease in AUC/Dose across the dose range 30-900 mg (397-97 ng/mL·h/(mg/kg)). Bioavailability relative to 30 mg/kg has been calculated as (AUC/Dose)/(AUC/30 mg) and is plotted for this group in FIG. 11.

Exposure in patients is also sub-proportional from 100 to 300 mg. It is noted that the average steady-state AUC in this study at 300 mg (32992 ng/mL·h) is approximately 2-fold lower than the $AUC_{inf}$ from a single dose in healthy volunteers (64285 ng/mL·h). This may be due to the use of a tablet formulation in the patient study versus the powder/suspension in healthy volunteers or may simply reflect a high degree of inter-subject variability (typically exposure CV is >50% within a study group).

The steady state (day 84) $C_{min}$ in patients at 400 mg and 600 mg has been measured. While the AUC in this study was not calculated, as the half-life is relatively long (>24 h), $C_{min}$, $C_{max}$ & $C_{avg}$ is expected to be similar and so AUC can be approximated by $C_{min}$*24 to allow comparison with other studies (the true value is expected to be slightly higher). This indicates that exposure at 400 mg (68616 ng/mL·h) is super-proportional relative to 300 mg in patients (32992 ng/mL·h) which is contrary to the general trend that AUC/Dose decreases with dose. Again, this may reflect inter-subject variability or a difference in the excipients used in the tablets.

Figure 12A:
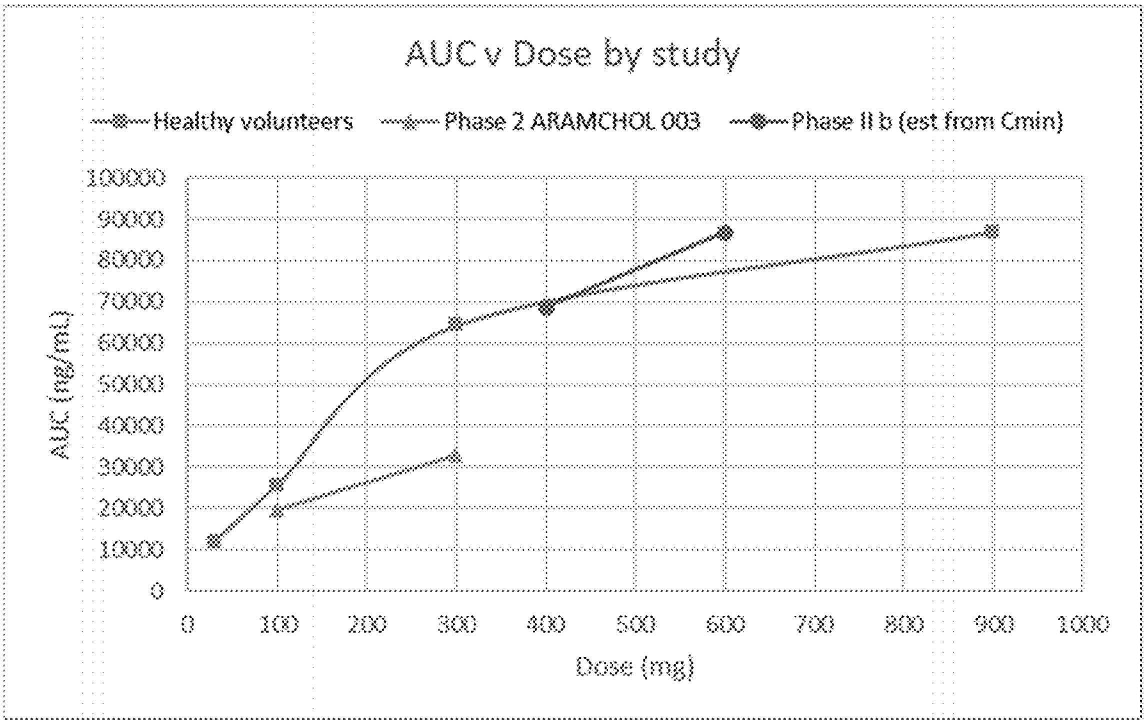
FIGS. 12A-12B depict the AUC vs. dose (FIG. 12A) and AUC/Dose vs. dose (FIG. 12B) grouped by study. AUC for the Phase IIb study in circles is estimated from the observed $C_{min}$ on D84*24 h.
Figure 12B:
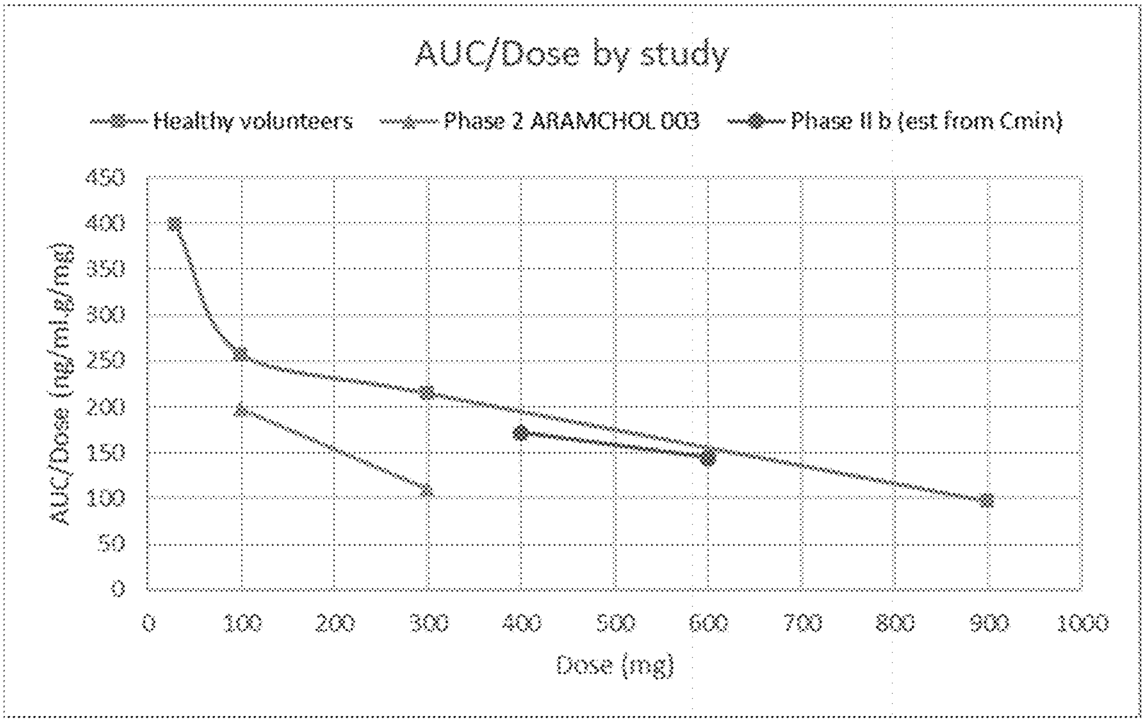

Plots of AUC v Dose and AUC/Dose v Dose are shown in FIGS. 12A and 12B.

Modelling and Simulation

Given the sub-proportional exposure generally seen, splitting the same total daily dose into two BID doses is likely to increase plasma AUC. The aim of this analysis was to model this behavior.

Figure 13A:
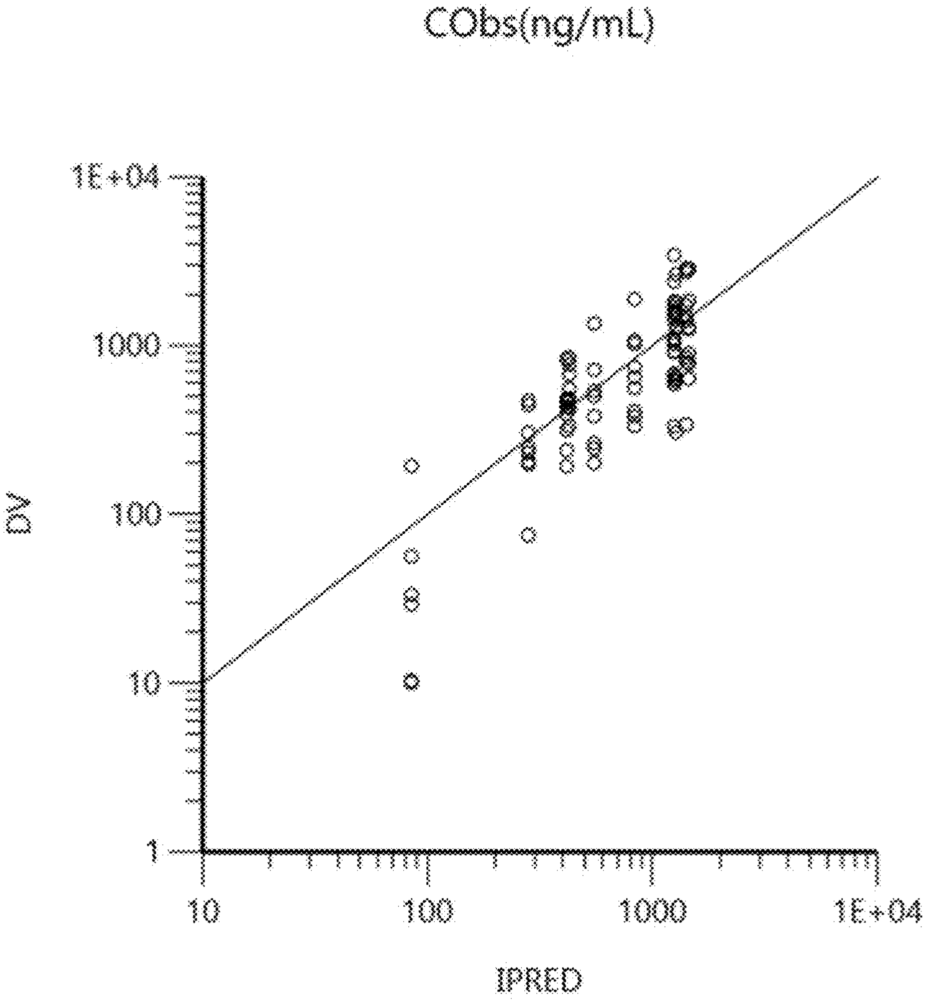
FIG. 13A depicts the predicted versus observed concentration (straight line represents the dose level and study).
Figures 13B, 13C:
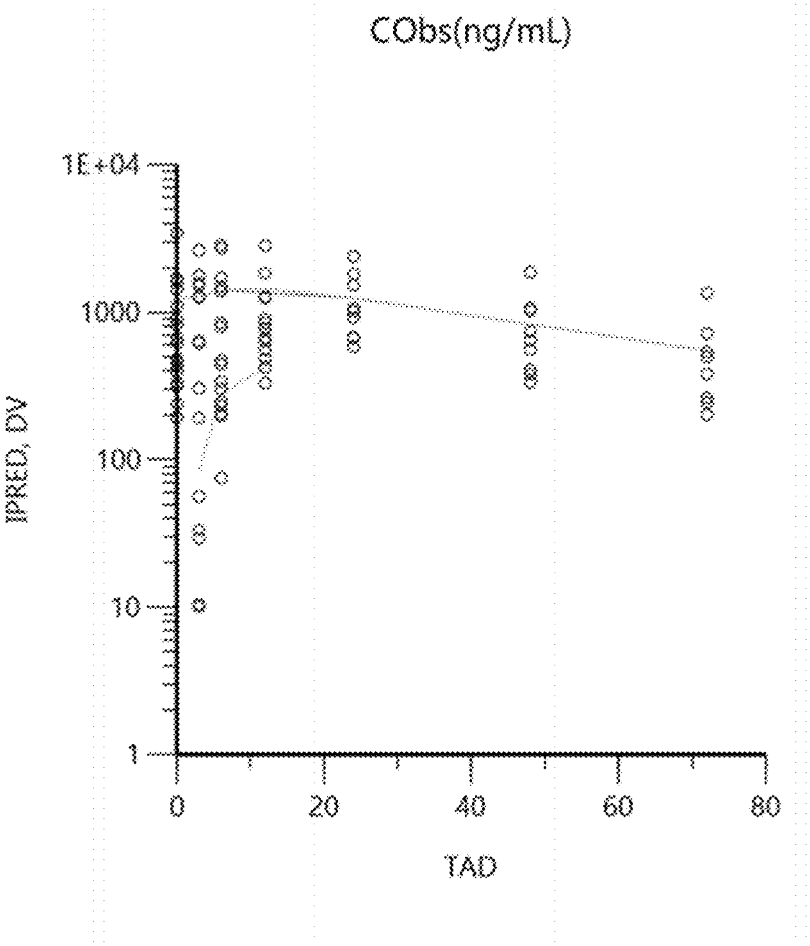
FIG. 13B depicts the predicted versus observed concentration-time after dose (circles=observed, sold lines=model).
FIG. 13C depicts the data and model parameters.

The 300 mg data on day 1 and day 84 in patients (Phase 2 ARAMCHOL™ 003) has been modelled in Phoenix 64® assuming single compartment pharmacokinetics (parameterized by Cl and V) and first order absorption at a rate Ka with a delay, Tlag. The fitted model parameters all have a CV<25% and the predicted concentration data reasonably capture the observed data as shown in FIGS. 13A-13C.

Figures 14A, 14B:
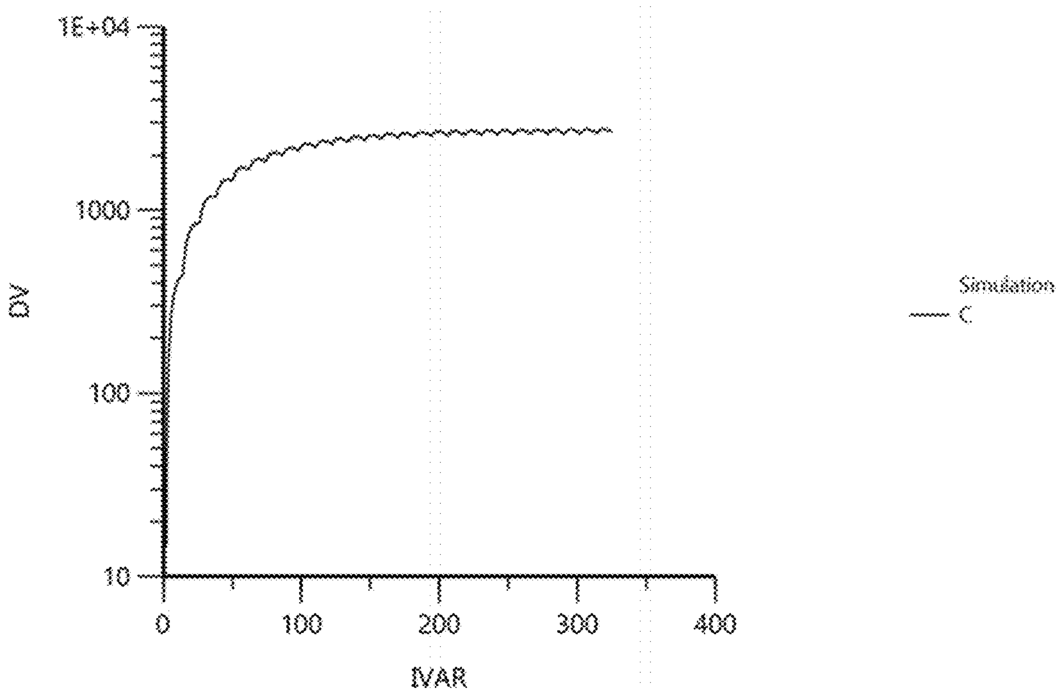
FIG. 14A is the simulated plasma exposure from a 300 mg BID dose using the model parameters (FIG. 14B) fit to the observed data at 300 mg QD in patients (Tlag is the delay in absorption; V/F is the volume of the central compartment divided by the bioavailability; Cl/F is the clearance from the compartment divided by bioavailability; and Ka is the rate of absorption into the compartment).

These model parameters were used to simulate exposure at 300 mg BID as shown in FIGS. 14A-14B. The predicted steady state $C_{min}$ using this model is 2630 ng/mL with an AUC of 65500 ng/mL·h.

To predict exposure at 600 mg, a correction for sub-proportional PK (lower bioavailability at higher dose) has been made assuming the same non-linearity at observed in healthy volunteers. Based on, FIGS. 13A-13C, relative bioavailability will be approximately 0.75 fold lower at 600 mg (ca. 0.4) compared to 300 mg (0.53) and the model parameters V/F and Cl/F from the 300 mg data have been adjusted accordingly.

Figures 15A, 15B:
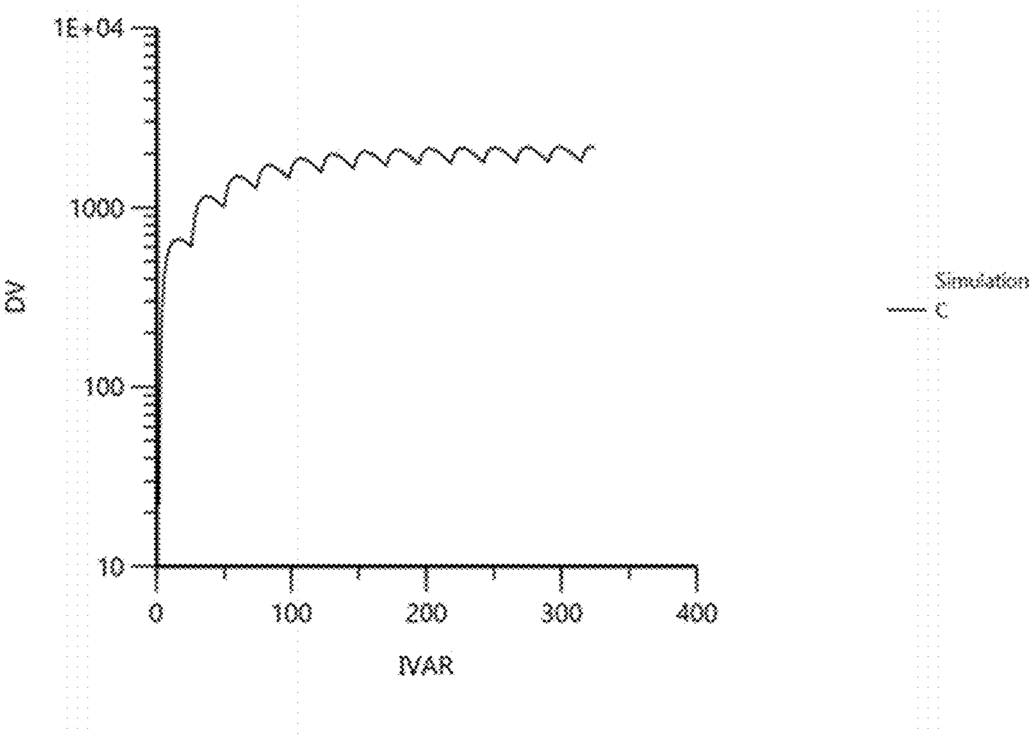
FIGS. 15A-15B present simulated plasma exposure from a 600 mg QD dose (FIG. 15A) using the model parameters (FIG. 15B) fit to the observed data at 300 mg QD in patients with 75% lower bioavailability estimated from the non-linear exposure in healthy volunteers between 300 and 900 mg (resulting in higher V/F and Cl/F), (Tlag is the delay in absorption; V/F is the volume of the central compartment divided by the bioavailability; Cl/F is the clearance from the compartment divided by bioavailability; and Ka is the rate of absorption into the compartment).

The simulated exposure from a 600 mg QD dose is shown in FIGS. 15A-15B with a predicted $C_{min}$ of 1820 ng/mL and an AUC of 49100 ng/mL·h.

Given the variability in exposure between subjects and between studies, the absolute values of AUC and $C_{min}$ are likely to differ from those predicted but a 300 mg BID dose is predicted, on average, to give a $C_{min}$ approximately 1.4-fold higher than 600 mg QD and a 1.3-fold higher AUC.

In summary:

Exposure of drug is expressed by area under the curve (AUC, the integrated concentration-time profile) and is often linear with dose. Under these circumstances, one dose of 900 mg Aramchol™ is expected to give three times the exposure (AUC) of 300 mg dose. However, it was found that higher doses result in a lower than linear increase in exposure. Accordingly, a single 900 mg dose gave only 1.35 fold higher exposure (AUC=86943 ng/mL·h) than a single 300 mg dose (AUC=64285 ng/mL·h) in healthy volunteers, despite the 3 fold higher dose. This is likely due to incomplete absorption of Armachol at the higher dose level. Based on this relationship, two 300 mg doses, for example, with a 12 h dose interval are expected to give higher exposure than a single daily 600 mg dose by a factor of approximately 1.4.

Example 7: Mechanistic Studies with Aramchol™: Aramchol™ Downregulates SCD1 and Induces PPARγ in Hepatic Stellate Cells to Attenuate Cellular Activation and Fibrogenesis Background Activation of hepatic stellate cells (HSCs) drives hepatic fibrosis through a process that is inhibited by PPARγ signaling. Aramchol™ (arachidyl amido cholanoic acid) is a fatty acid-bile acid conjugate that reduces liver fat content in nonalcoholic fatty liver disease (NAFLD) and improved nonalcoholic steatohepatitis (NASH) without worsening fibrosis in a Phase 2b study. Aramchol™ attenuates fibrosis in two distinct models (MCD diet and thioacetamide). In mice, Aramchol™ reduces liver fat by downregulating the fatty acid synthetic enzyme stearoyl Co-A desaturase 1 (SCD-1) in hepatocytes. The mechanism for Aramchol™'s antifibrotic effect is not known; moreover, although HSCs also store lipids as retinyl esters. The role of SCD-1 in HSCs and the impact of Aramchol™ on SCD-1 activity are unknown.

Aim:

To investigate the direct anti-fibrotic effect of Aramchol™ on HSCs using LX-2, a human hepatic stellate cell line, and to define the mechanism of Aramchol™'s effects on HSCs.

Methods:

Serum-starved LX2 cells were treated with Aramchol™ (10 μM) for 24 or 48 hours. Fibrogenic gene expression and SCD-1 protein expression were measured by qPCR and Western, respectively. RNAseq was performed at 24 and 48 h in duplicate. Differential gene expression was assessed with DSeq2, while gene set enrichment analysis (GSEA) and gene ontology (GO) analyses assessed functionality of gene expression changes. Primary hepatocytes from C57BL/6 mice were harvested by perfusion and treated with Aramchol™ (10 μM) for 48 hours in culture. PPAR γ mRNA expression was measured by qPCR.

Results:

Results are shown in FIGS. 21A-21B to FIGS. 25A-25B.

Figure 21A:
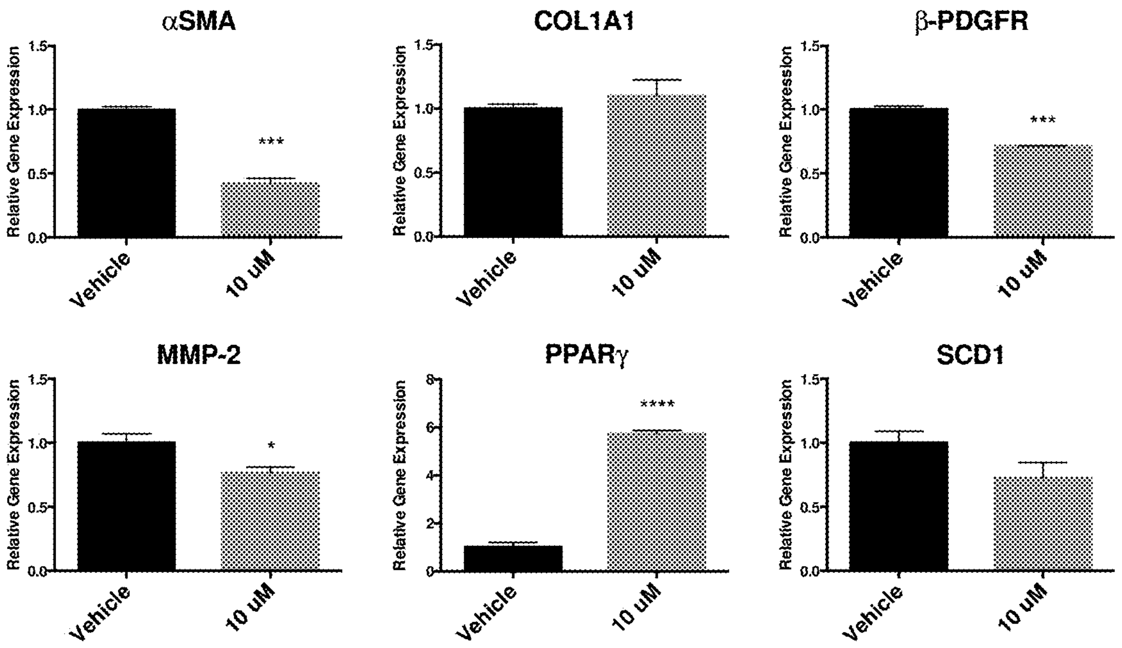
FIGS. 21A-21B depict how Aramchol™ downregulates SCD-1 mRNA and fibrogenic genes and upregulates PPARγ mRNA in HSCs. Based on RT-PCR (N=3) *$p<0.05$, $p<0.01$, *$p<0.01$.
Figure 21B:
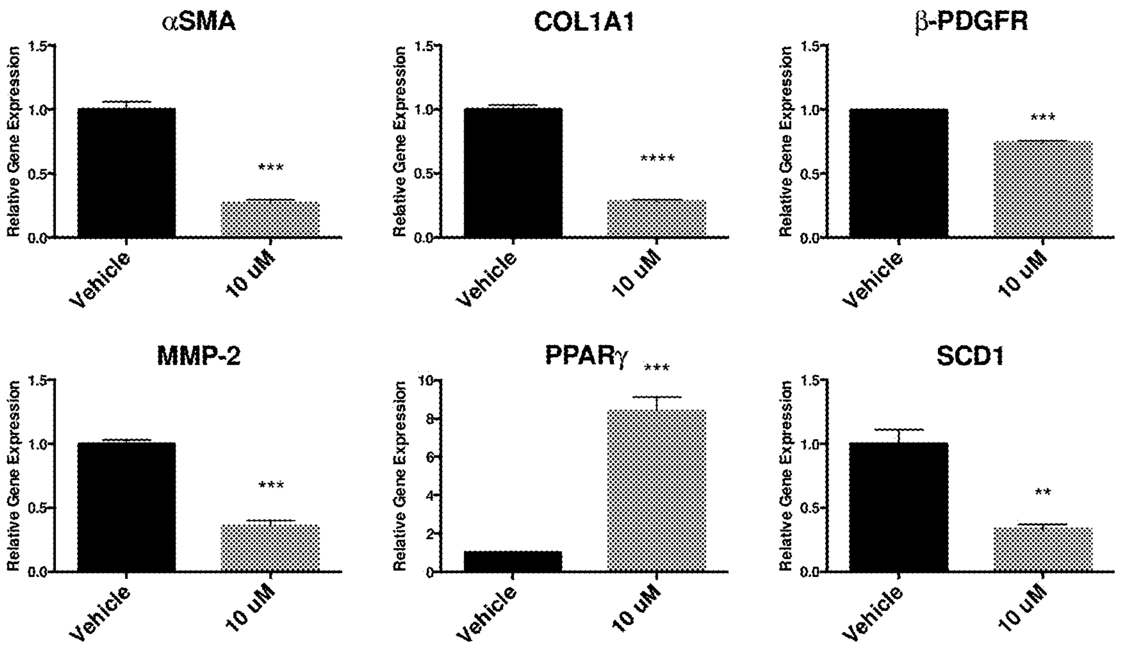

FIGS. 21A-21B depict how Aramchol™ downregulates SCD-1 mRNA and fibrogenic genes and upregulates PPARγ mRNA in HSCs. Based on RT-PCR (N=3) *p<0.05, p<0.01, *p<0.001.

Figure 22A:
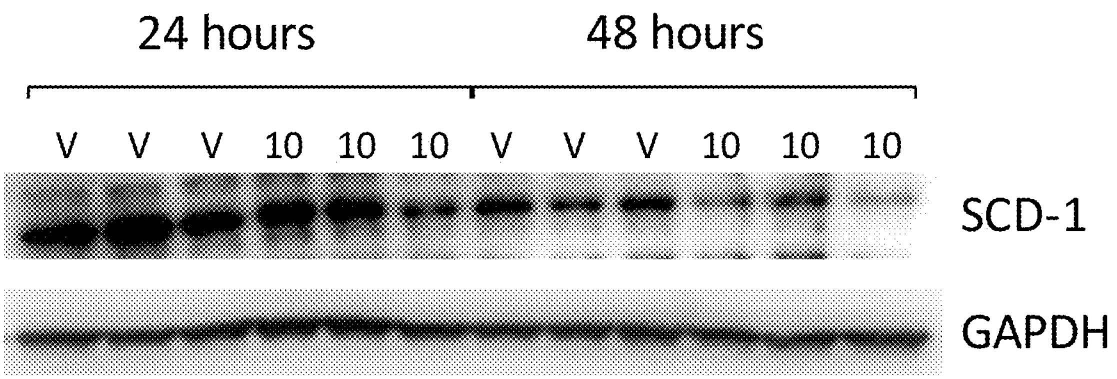
FIGS. 22A-22B depict how Aramchol™ downregulates SCD-1 in HSCs.
Figure 22B:
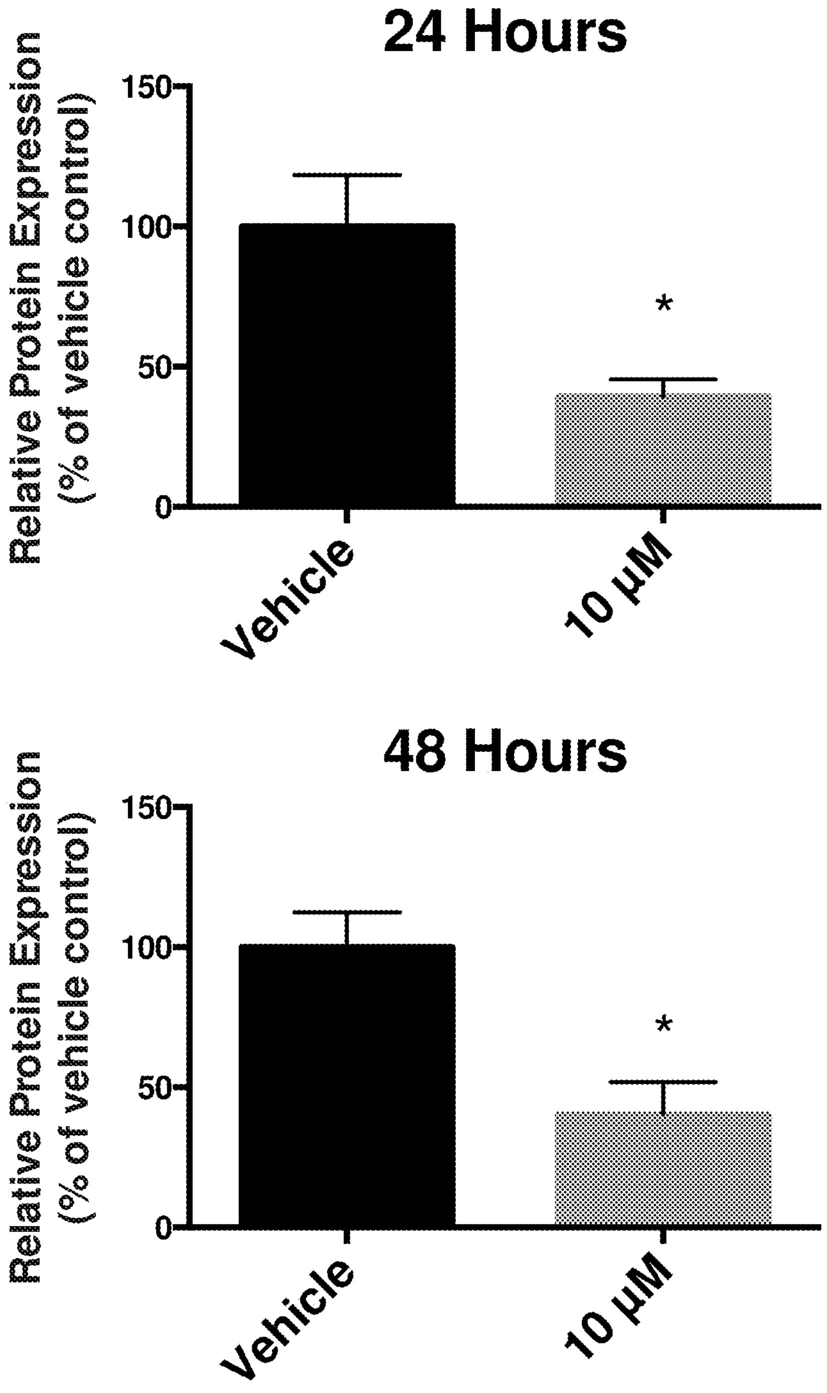

FIGS. 22A-22B depict how Aramchol™ downregulates SCD-1 in HSCs. FIG. 22A and FIG. 22B depict the Western Blot and the densitometry respectively of downregulated SCD-1 protein in HSCs treated with Aramchol™ for 24 or 48 hrs. (N=3) *p<0.05, p<0.01, *p<0.001.

Figure 23:
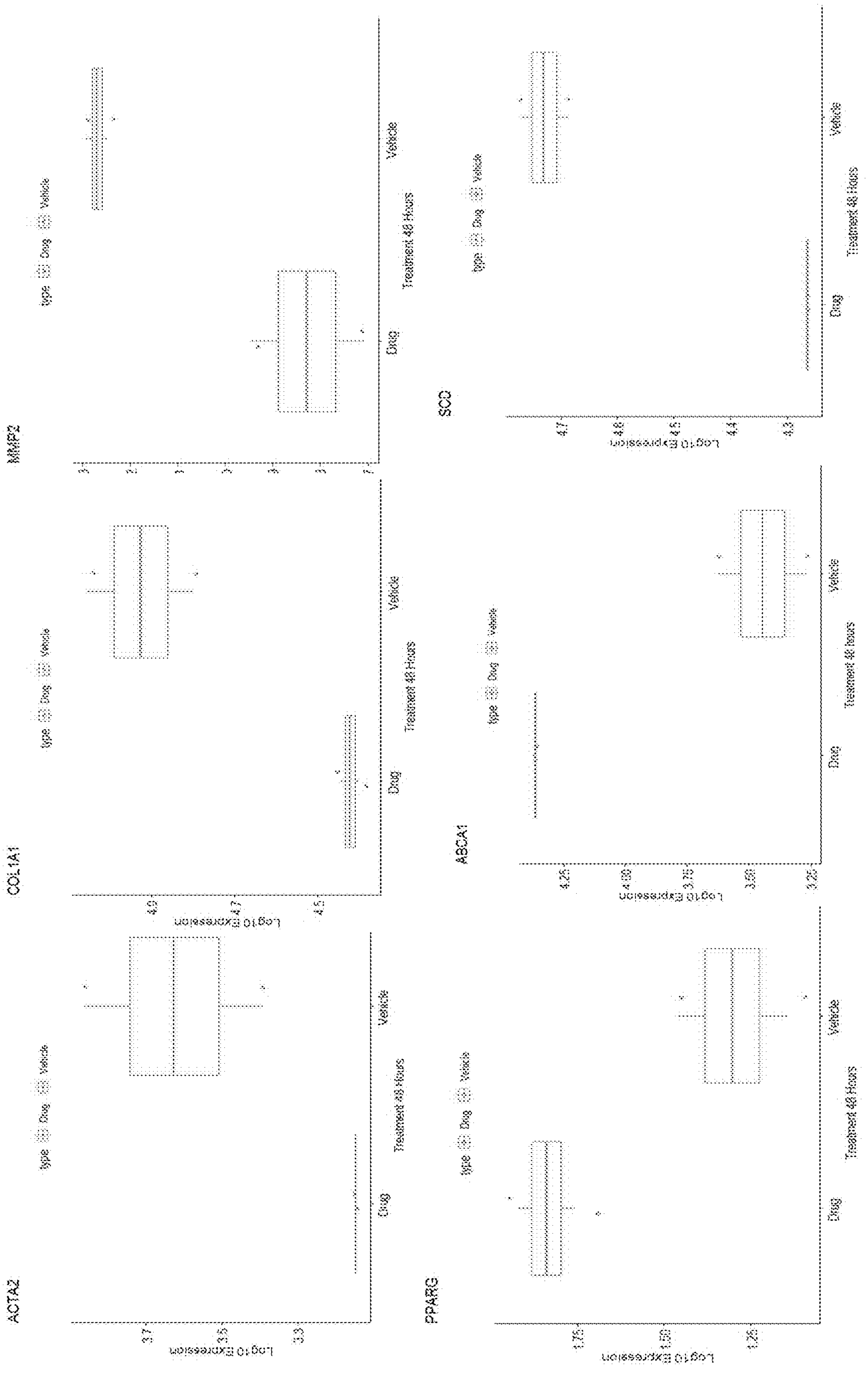
FIG. 23 depicts the confirmation by RNASeq for downregulation of fibrogenic genes and SCD-1 mRNA, and upregulation of PPARγ mRNA after 48 hrs of treatment with Aramchol™ The cholesterol efflux regulatory protein, ABCA1, is also upregulated.

FIG. 23 depicts the confirmation by RNASeq for downregulation of fibrogenic genes and SCD-1 mRNA, and upregulation of PPARγ mRNA after 48 hrs of treatment with Aramchol™ The cholesterol efflux regulatory protein, ABCA1, is also upregulated.

Figure 24:
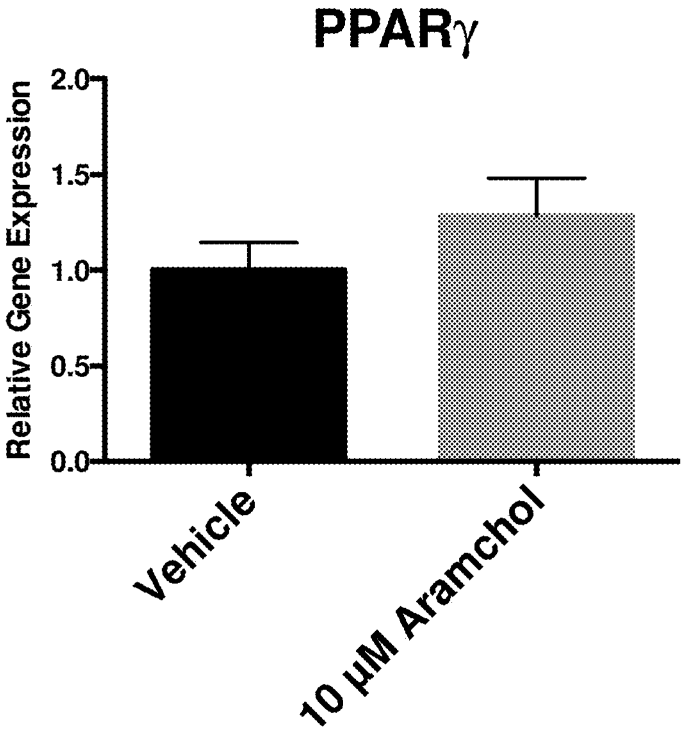
FIG. 24 depicts that Aramchol™ does not affect PPARγ mRNA expression in primary mouse hepatocytes after 48 hours of treatment. (N=3) *$p<0.05$, $p<0.01$, *$p<0.001$.

FIG. 24 depicts that Aramchol™ does not affect PPARγ mRNA expression in primary mouse hepatocytes after 48 hours of treatment. (N=3) *p<0.05, p<0.01, *p<0.001

Figure 25A:
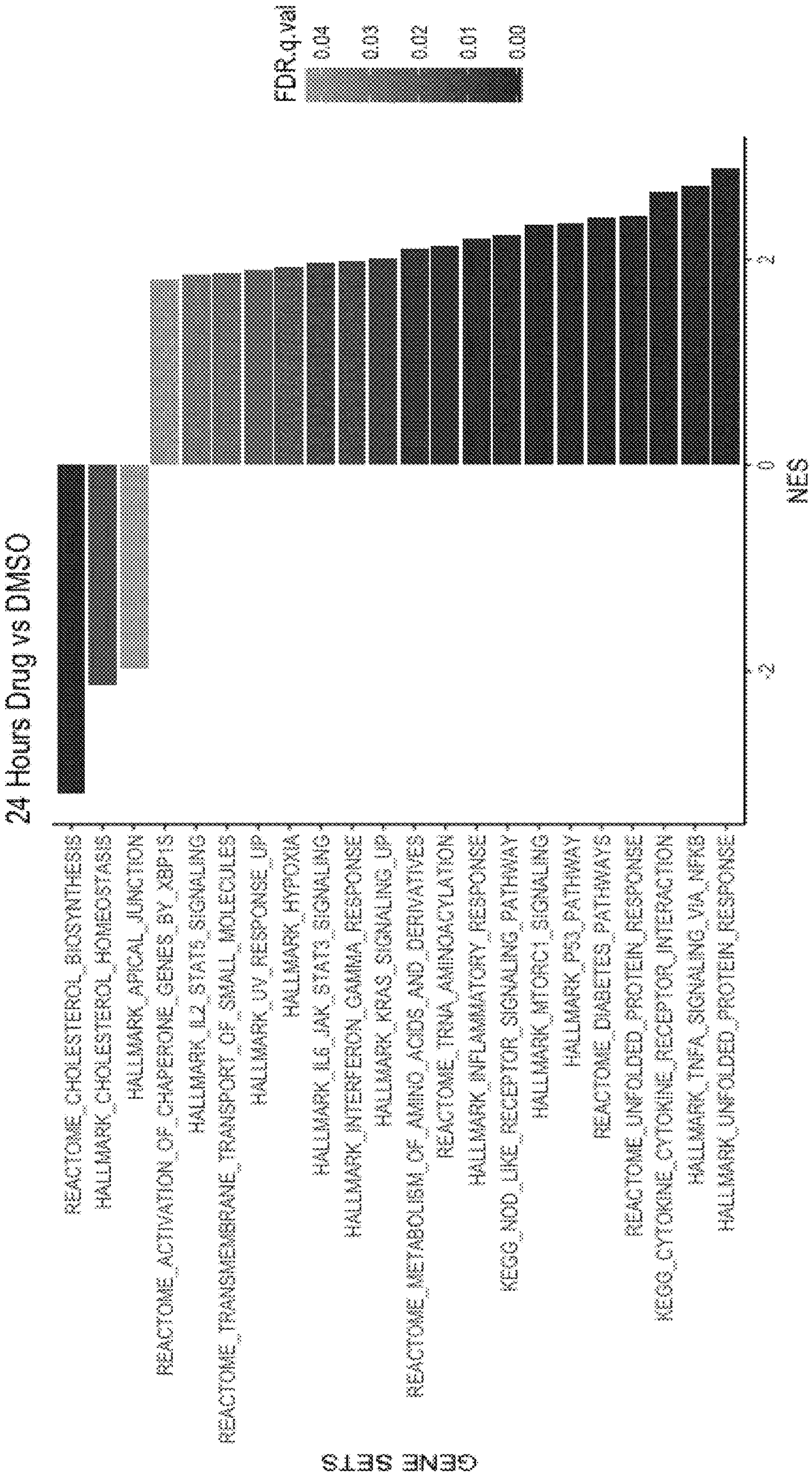
FIGS. 25A-25B depict how Aramchol™ downregulates cholesterol biosynthesis and collagen formation in HSCs. Gene Set Enrichment Analysis of LX-2 cells after 24 (FIG. 25A) or 48 (FIG. 25B) hours of treatment.
Figure 25B:
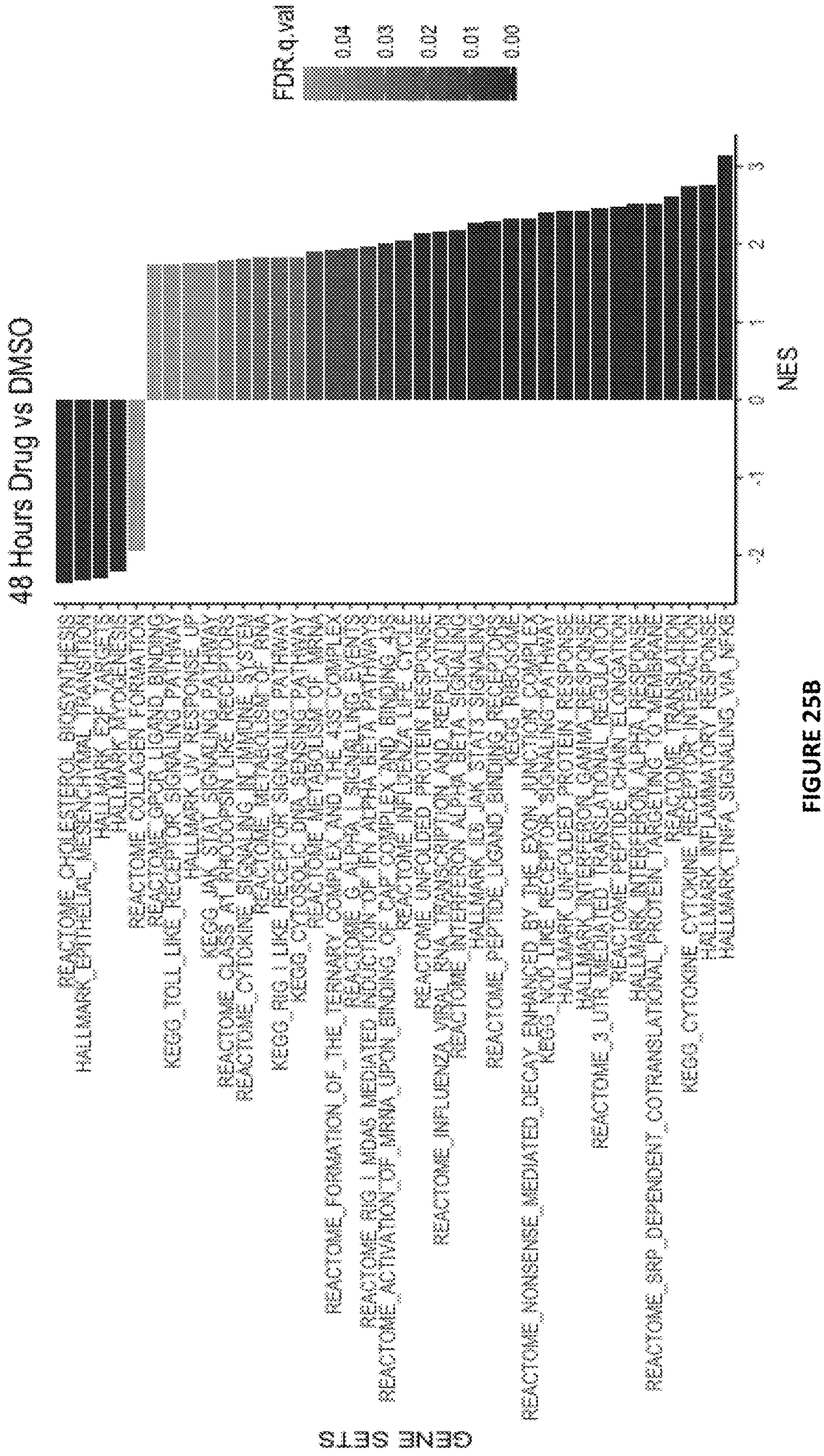

FIGS. 25A-25B depict how Aramchol™ downregulates cholesterol biosynthesis and collagen formation in HSCs. Gene Set Enrichment Analysis of LX-2 cells after 24 (FIG. 25A) or 48 (FIG. 25B) hours of treatment.

Conclusions:

Aramchol™ elevates PPAR γ mRNA and down regulates SCD-1 mRNA and protein and in hepatic stellate cells. By RNAseq and pathway analysis, Aramchol™ downregulates fibrogenic genes that are part of a clinically validated HSC activation signature, including COL1A1 and αSMA, as well as pathways involved in cholesterol biosynthesis & homeostasis, and collagen formation. Aramchol™ upregulates PPARγ mRNA selectively in HSCs and not in hepatocytes.

Example 8: Pulmonary Fibrosis Treatment by Aramchol™

The following model was employed:

Male C57BL/12mice, 22-26 g

Induction by administration of Bleomycin (1.5 U/kg), intratracheal

Ref Comp.: Pirfenidone, 100 mg/kg, p.o., BID

Treatment Mode: Prophylactic (from day 0→21)

Figure 26A:
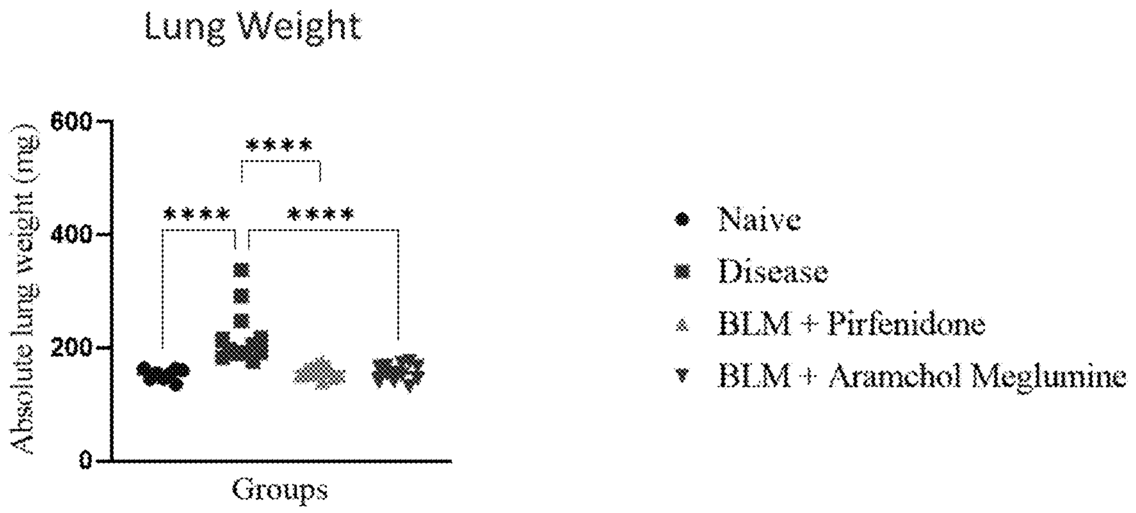
FIGS. 26A-26B depict how Aramchol™ (meglumine salt) or pirfenidone affect lung weight (FIG. 26A) and hydroxyproline concentration (FIG. 26B) in mice afflicted with pulmonary fibrosis (induced by bleomycin (BLM)).
Figure 26B:
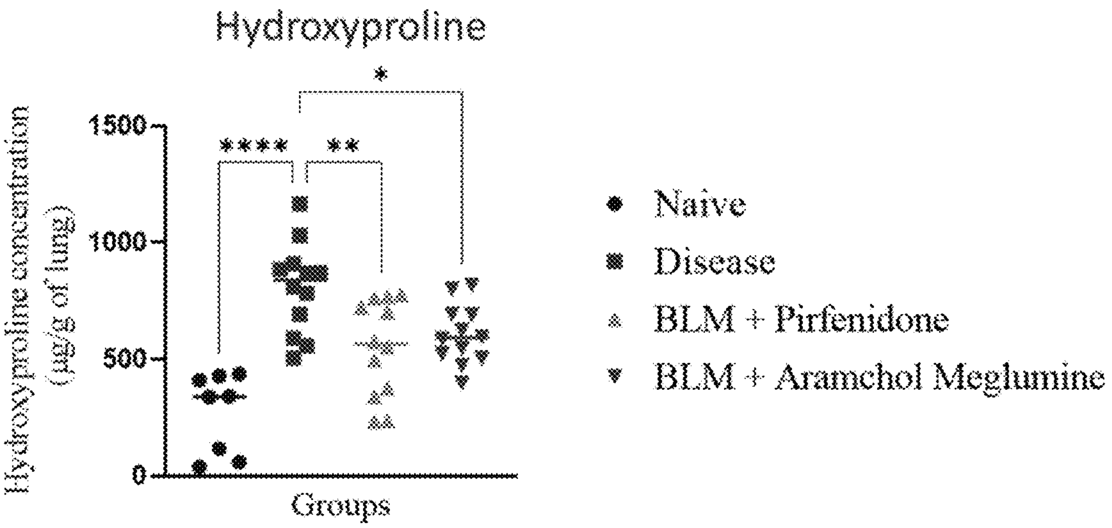

Pulmonary fibrosis was induced by bleomycin (BLM) and treated with aramchol (meglumine salt). As a reference, results for the known anti-idiophatic pulmonary fibrosis agent pirfenidone are also presented, in FIGS. 26A-26B, where hydroxyproline was used as biomarker for fibrosis (hydroxyproline use as idiophatic pulmonary fibrosis biomarker is disclosed in "*Lung fibrosis is ameliorated by pirfenidone fed in diet after the second dose in a three-dose bleomycin-hamster model*", Iyer, Swarnalatha N.; Margolin, S. B.; Hyde, D. M.; Gin, S. N.; Experimental Lung Research (1998), 24(1), 119-132; and "*Simple determination of L-hydroxyproline in idiopathic pulmonary fibrosis lung tissues of rats using non-extractive high-performance liquid chromatography coupled with fluorescence detection after pre-column derivatization with novel synthetic* 9-*acetylimidazol-carbazole*", Ren, Y.; Zhao, J.; Shi, Y.; Chen, C.; Chen, X.; Lv, C.; Journal of Pharmaceutical and Biomedical Analysis 2017, 142, 1-6).

Figure 27:
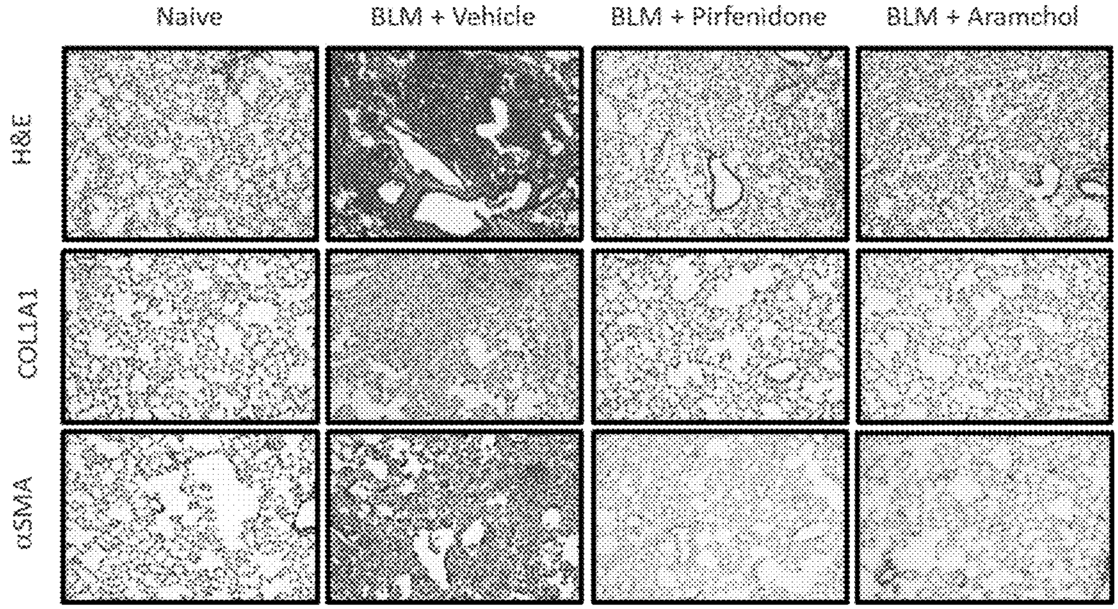
FIG. 27 depicts histopathology of the lungs of mice having pulmonary fibrosis induced by bleomycin (BLM) and treated with Aramchol™ (meglumine salt) or pirfenidone. "H & E": Hematoxylin and Eosin (H&E) staining; "COL1A1": a gene encoding the alpha1 chain of type I collagen; and "αSMA": α-Smooth muscle actin—a marker of myofibroblast formation.
Figure 28A:
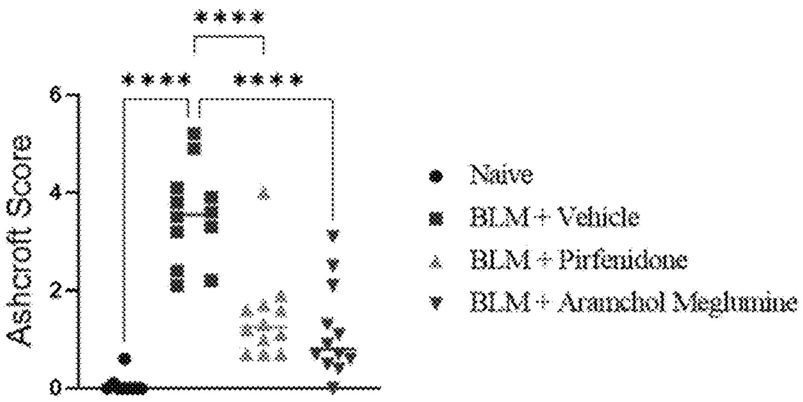
FIGS. 28A-28E depict Aschroft score (FIG. 28A); COL1A1 (FIGS. 28B-28C); and αSMA (FIGS. 28D-28E) results of mice having pulmonary fibrosis induced by bleomycin (BLM) and treated with Aramchol™ (meglumine salt) or pirfenidone. "Ashcroft score": a scale for evaluating pulmonary fibrosis, where the higher the score, the more severe the pulmonary fibrosis is; "COL1A1": a gene encoding the alpha1 chain of type I collagen; and "αSMA": α-Smooth muscle actin—a marker of myofibroblast formation.
Figure 28B:
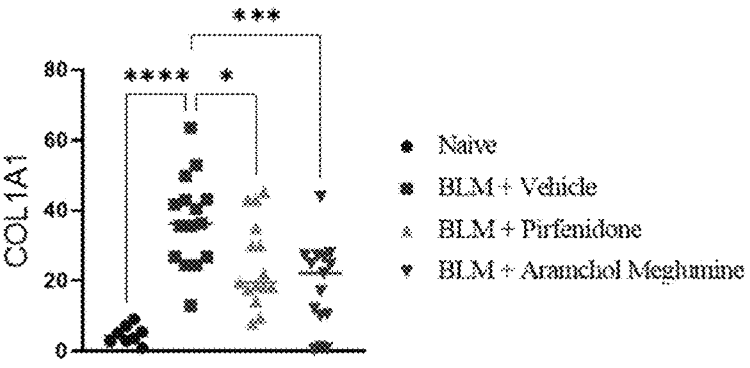
Figure 28C:
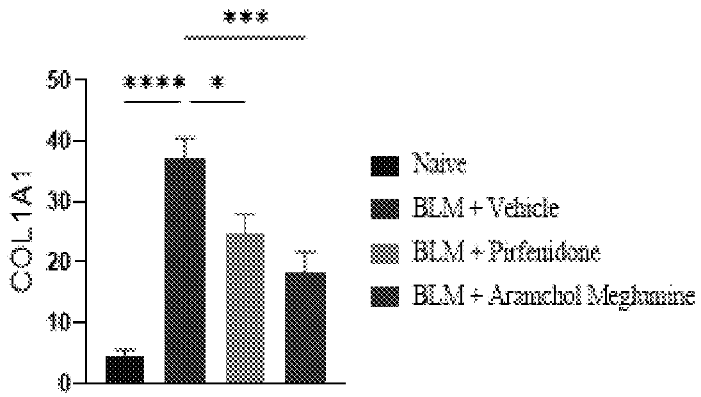
Figure 28D:
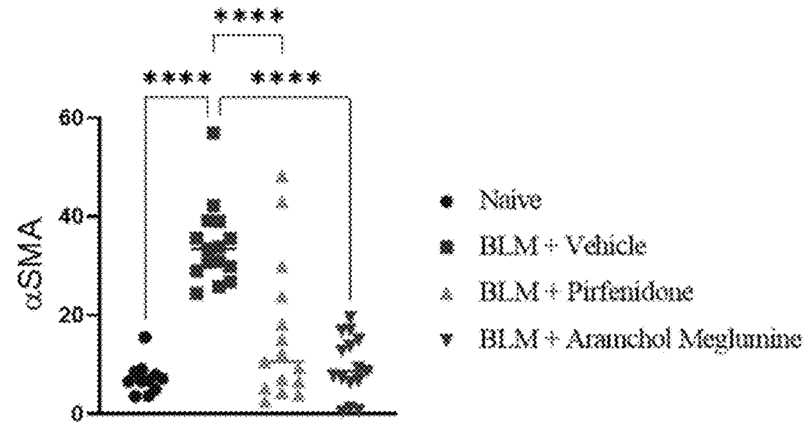
Figure 28E:
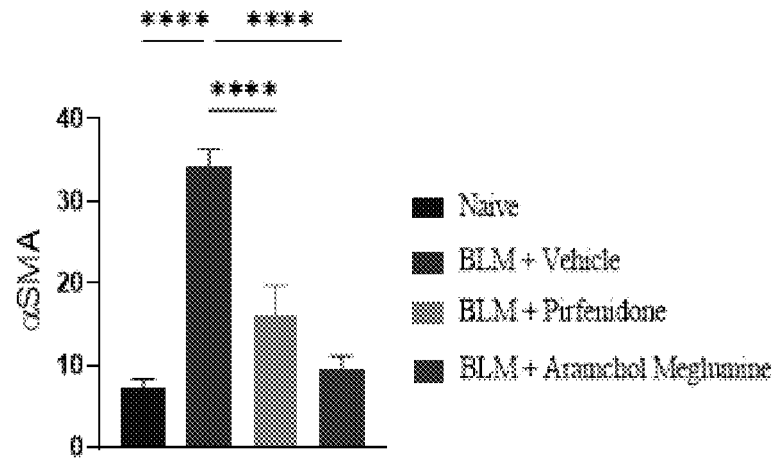

Further, histopathology of the lungs of mice having pulmonary fibrosis induced by bleomycin and treated with aramchol is shown in FIG. 27.

The pictograms within FIG. 27 show that in "BLM+vehicle" (BLM=bleomycin), where pulmonary fibrosis was found—tissues were much more dense and dark-colored. In the pirfenidone case the picture is much more similar to the one without the fibrosis (i.e. it's similar to "naïve" case). Evidently with aramchol treatment—the picture is very similar to the one of pirfenidone, one of the two drugs approved to date for retarding idiopathic pulmonary fibrosis (IPF), a serious, rare and fatal lung disease, with a life expectancy of 3-5 years. The pulmonary fibrosis was thus treated with aramchol.

Additionally, the graphs of FIGS. 28A-28E are based on, and quantitatively analyze the visual results of the histopathological results of FIG. 27. As can be seen, said graphs also confirm that aramchol treats pulmonary fibrosis. Further, when compared to pirfenidone, also known as Pirespa®, Esbriet® or Pirfenex® for the treatment of IPF, aramchol treats the fibrosis in better (higher) extent and has more significant effect.

The invention claimed is:

1. A method for treating fibrosis selected from the group consisting of: pulmonary fibrosis and heart fibrosis, in a human subject afflicted with said condition comprising administering to the subject 3β-arachidylamido-7α, 12α-dihydroxy-5β-cholan-24-oic acid (Aramchol), or a pharmaceutically acceptable salt thereof, thereby treating said condition in said subject, wherein said Aramchol or a pharmaceutically acceptable salt thereof is the sole active ingredient administered.

2. The method of claim 1, wherein 400 mg, 600 mg, 800 mg; or greater than 300 mg of Aramchol or a pharmaceutically acceptable salt thereof is administered to the subject per day.

3. The method of claim 1, wherein the Aramchol or a pharmaceutically acceptable salt thereof is administered with water, or at the same time as, or within 30 minutes of a meal; wherein the meal is breakfast, lunch, or dinner, or wherein the meal is a high fat meal or a high calorie meal.

4. The method of claim 1, wherein the Aramchol or a pharmaceutically acceptable salt thereof is administered over the course of at least 40 weeks, at least 52 weeks, at least 72 weeks, at least 96 weeks, at least 2 years, at least 3 years, or at least 4 years.

5. The method of claim 1, wherein the human subject has a diet that is high fat and high calorie; and/or is resistant to lifestyle intervention or is resistant to diet intervention.

6. A method for treating pulmonary fibrosis, in a human subject afflicted with said condition comprising administering to the subject 3β-arachidylamido-7α, 12α-dihydroxy-5β-cholan-24-oic acid (Aramchol), or a pharmaceutically acceptable salt thereof, thereby treating said condition in said subject, wherein said Aramchol or a pharmaceutically acceptable salt thereof is the sole active ingredient administered.

* * * * *